(12) United States Patent
Edgar et al.

(10) Patent No.: US 7,189,757 B2
(45) Date of Patent: Mar. 13, 2007

(54) TREATMENT OF SLEEP DISORDERS USING CNS TARGET MODULATORS

(75) Inventors: Dale M. Edgar, Wayland, MA (US); David G. Hangauer, East Amherst, NY (US); Harry Jefferson Leighton, Brookline, MA (US); Emmanuel J. M. Mignot, Palo Alto, CA (US)

(73) Assignee: Hypnion, Inc., Lexington, MA (US)

( * ) Notice: Subject to any disclaimer, the term of this patent is extended or adjusted under 35 U.S.C. 154(b) by 468 days.

(21) Appl. No.: 10/272,510

(22) Filed: Oct. 16, 2002

(65) Prior Publication Data

US 2003/0187021 A1 Oct. 2, 2003

Related U.S. Application Data

(60) Provisional application No. 60/329,701, filed on Oct. 16, 2001, provisional application No. 60/381,507, filed on May 17, 2002, provisional application No. 60/414,243, filed on Sep. 27, 2002, provisional application No. 60/418,821, filed on Oct. 16, 2002.

(51) Int. Cl.
*A61K 31/35* (2006.01)
*A61K 31/335* (2006.01)
*A61K 31/535* (2006.01)

(52) U.S. Cl. ............... 514/454; 514/450; 514/320; 514/324; 514/325

(58) Field of Classification Search ........... 514/255, 514/316, 320, 324, 325, 454, 450
See application file for complete search history.

(56) References Cited

U.S. PATENT DOCUMENTS

| | | | | |
|---|---|---|---|---|
| 3,928,356 A * | 12/1975 | Umio et al. | ............... | 544/378 |
| 4,072,756 A * | 2/1978 | Ebnother et al. | ........... | 514/321 |
| 4,383,999 A | 5/1983 | Bondinell et al. | ........... | 424/266 |
| 4,514,414 A | 4/1985 | Bondinell et al. | ........... | 514/422 |
| 4,610,995 A | 9/1986 | Coker et al. | ............... | 514/343 |
| 4,929,618 A | 5/1990 | Koda et al. | | |
| 4,931,450 A | 6/1990 | Sonnewald | ................ | 514/326 |
| 5,095,022 A * | 3/1992 | Ito et al. | ...................... | 514/320 |
| 5,153,207 A | 10/1992 | Ito et al. | | |
| 5,225,559 A | 7/1993 | Kita et al. | ................... | 546/194 |
| 5,231,105 A | 7/1993 | Shoji et al. | .................. | 514/325 |
| 5,502,047 A * | 3/1996 | Kavey | ......................... | 514/183 |
| 5,643,897 A | 7/1997 | Kavey | ......................... | 514/183 |
| 5,714,501 A * | 2/1998 | Timmerman et al. | ........ | 514/325 |
| 5,776,969 A * | 7/1998 | James | ......................... | 514/418 |
| 5,801,175 A | 9/1998 | Afonso et al. | .............. | 514/254 |
| 6,054,458 A | 4/2000 | Jørgensen et al. | ........... | 514/255 |
| 6,174,880 B1 * | 1/2001 | Bernstein | ................. | 514/217 |
| 6,174,898 B1 | 1/2001 | Weis et al. | ................. | 514/315 |
| 6,191,165 B1 | 2/2001 | Ognyanov et al. | ........... | 514/523 |
| 6,214,827 B1 | 4/2001 | Afonson et al. | ........ | 514/252.13 |
| 6,288,083 B1 | 9/2001 | Luly et al. | ................... | 514/318 |
| 6,288,084 B1 | 9/2001 | Luly et al. | ................... | 514/318 |
| 6,307,052 B1 | 10/2001 | Kita et al. | ................... | 546/194 |
| 6,358,944 B1 | 3/2002 | Lederman et al. | | |
| 6,387,930 B1 | 5/2002 | Baroudy et al. | | |
| 6,391,890 B1 * | 5/2002 | J.o slashed.rgensen et al. | ......................... | 514/316 |
| 6,503,926 B2 | 1/2003 | Luly et al. | ................... | 514/318 |

FOREIGN PATENT DOCUMENTS

| | | |
|---|---|---|
| EP | 0 335 586 A1 | 10/1989 |
| EP | 0 399 414 A1 | 11/1990 |
| EP | 451772 A1 * | 10/1991 |
| EP | 0 949 260 B1 | 10/1999 |
| JP | 03133956 | 6/1991 |
| JP | 05-17442 A | 1/1993 |
| JP | 05-17443 A2 | 1/1993 |
| JP | 05-294929 A | 11/1993 |
| JP | 2001-261553 A | 9/2001 |
| JP | 2004-051600 A2 | 2/2004 |
| WO | WO 88/09656 | 12/1988 |
| WO | WO 95/01350 | 1/1995 |
| WO | WO 96/31478 | 10/1996 |
| WO | WO 97/45115 | 12/1997 |
| WO | WO 00/14064 | 3/2000 |
| WO | WO 03/033489 A1 | 4/2003 |

OTHER PUBLICATIONS

Andersen et al. *J. Med. Chem.*, 36(12):1716-1725 (1993).
Andersen et al. *J. Med. Chem.*, 42:4281-4291 (1999).
Dhar et al. *Bioorg. Med. Chem. Lett.*, 6(13):1535-1540 (1996).
Falch et al. *Eur. J. Med. Chem.*, 26:69-78 (1991).
Iwasaki et al. *Chem. Pharm. Bull.*, 42(11):2276-2284 (1994).
Iwasaki et al. *Chem. Pharm. Bull.*, 42(11):2285-2290 (1994).
Muramatsu et al. *Chem. Pharm. Bull.*, 41(11)1987-1993 (1993).
N'Goka et al. *J. Med. Chem.*, 34(8):2547-2557 (1991).
Ohshima et al. *J. Med. Chem.*, 35(11):2074-2084 (1992).
Patani et al. *Chem. Rev.*, 96(8):3147-3176 (1996).
Yunger et al. *J. Pharmacol. Exp. Ther.*, 228(1):109-115 (1984).

* cited by examiner

*Primary Examiner*—Brian Kwon
(74) *Attorney, Agent, or Firm*—Ivor R. Elrifi; Heidi A. Erlacher; Mintz, Levin, Cohn, Ferris, Glovsky and Popeo, P.C.

(57) ABSTRACT

The invention is directed to compositions used for treating Central Nervous System (CNS) disorders. In addition, the invention provides convenient methods of treatment of a CNS disorder. Furthermore, the invention provides methods of treating sleep disorders using compositions that remain active for a discrete period of time to reduce side effects. More specifically, the invention is directed to the compositions and use of derivatized, e.g., ester or carboxylic acid derivatized, antihistamine antagonists for the treatment of sleep disorders.

6 Claims, 6 Drawing Sheets

TREATMENT OF SLEEP DISORDERS USING CNS TARGET MODULATORS

REFERENCE TO RELATED APPLICATIONS

This application claims the benefit of U.S. Provisional Patent Application Ser. No. 60/329,701, filed on Oct. 16, 2001, entitled "Treatment of CNS Disorders Using CNS Target Modulators"; U.S. Provisional Patent Application Ser. No. 60/381,507, filed on May 17, 2002, entitled "Treatment of CNS Disorders Using CNS Target Modulators"; and U.S. Provisional Patent Application Ser. No. 60/414,243, filed on Sep. 27, 2002, entitled "Treatment of CNS Disorders Using CNS Target Modulators". This application is also related to U.S. Provisional Patent Application Ser. No. 60/418,821, filed on even date herewith, entitled "Treatment of CNS Disorders Using CNS Target Modulators". The entire content of each of the above-identified applications is hereby incorporated herein by reference.

BACKGROUND OF THE INVENTION

Difficulties in falling asleep, remaining asleep, sleeping for adequate lengths of time, or abnormal sleep behavior are common symptoms for those suffering with a sleep disorder. A number of sleep disorders, e.g., insomnia or sleep apnea, are described in the online Merck Manual of Medicinal Information.

Current treatment of many sleep disorders include the use of prescription hypnotics, e.g., benzodiazapines, that may be habit-forming, lose their effectiveness after extended use, and metabolize more slowly for certain designated groups, e.g., elderly persons, resulting in persisting medicative effects.

Other, more mild manners of treatment include over-the-counter antihistamines, e.g., diphenhydramine or dimenhydrinate, which are not designed to be strictly sedative in their activity. This method of treatment is also associated with a number of adverse side effects, e.g., persistence of the sedating medication after the prescribed time of treatment, or the so-called "hangover effect". Many of these side effects result from nonspecific activity in both the periphery as well as the Central Nervous System (CNS) during this period of extended medication.

SUMMARY OF THE INVENTION

A need exists for the development of new compositions used for the improved treatment of sleep disorders that remain active for a discrete period of time to reduce side effects, such as the "hangover effect." The strategy of treatment is applicable to a broader array of CNS targets.

Therefore, the invention is directed to compositions used for treating Central Nervous System (CNS) disorders. In addition, the invention provides convenient methods of treatment of a CNS disorder. Furthermore, the invention provides methods of treating sleep disorders using compositions that remain active for a discrete period of time to reduce side effects. More specifically, the invention is directed to the compositions and use of derivatized, e.g., ester or carboxylic acid derivatized, antihistamine antagonists for the treatment of sleep disorders.

Thus, in one aspect of the invention, the invention is a method of treating a sleep disorder. The method comprises administering an effective amount of an antihistamine compound, such that the sleep disorder is treated, wherein the antihistamine compound has a favorable biological property (FBP).

An additional aspect of the invention is a method of treating a Central Nervous System (CNS) disorder. The method comprises administering an effective amount of a therapeutic compound to a subject, such that the therapeutic compound penetrates into the CNS and modulates the CNS target to treat the CNS disorder. Accordingly, the therapeutic compound can have the formula:

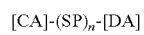

[CA]-(SP)$_n$-[DA]

wherein CA is a moiety that modulates an active CNS target receptor or a collection of active CNS target receptors, DA is a drug activity modulating moiety that provides the ability to modulate the activity of the therapeutic compound, e.g., ester or carboxylic acid, SP is a spacer molecule, and n is 0 or 1.

Another aspect of the invention is a method of treating a Central Nervous System (CNS) disorder. The method comprises administering an effective amount of a therapeutic compound to a subject, such that the therapeutic compound penetrates into the CNS and modulates the CNS target to treat the CNS disorder. Accordingly, the therapeutic compound can have the formula:

[CA]-(SP)$_n$-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

In a more specific aspect of the invention, the invention is directed to a method of treating a sleep disorder. The method comprises administering an effective amount of a therapeutic compound to a subject, such that the sleep disorder is treated. Accordingly, the therapeutic compound can have the formula:

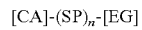

[CA]-(SP)$_n$-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

In an additional aspect, the invention is directed to a method of treating a sleep disorder target. The method comprises administering an effective amount of a therapeutic compound to a subject, such that the sleep disorder is treated. Accordingly, the therapeutic compound can have the formula:

[AD]-(SP)$_n$-[EG]

wherein AD is a moiety that agonizes an adenosine receptor or a collection of adenosine receptors, EG is an ester group that modifies the half-life of the therapeutic compound, SP is a spacer molecule, and n is 0 or 1.

Another aspect of the invention is directed to a method of treating a sleep disorder target. The method comprises administering an effective amount of a therapeutic compound to a subject, such that the sleep disorder is treated. Accordingly, the therapeutic compound can have the formula:

[AH]-(SP)$_n$-[DA]

wherein AH is a moiety that antagonizes a histamine receptor or a collection of histamine receptors, DA is a drug activity modulating moiety that provides the ability to modulate the activity of the therapeutic compound, SP is a spacer molecule, and n is 0 or 1.

In another aspect, the invention is directed to a method of treating a sleep disorder. The method comprises administering an effective amount of a therapeutic compound to a subject, such that the sleep disorder is treated. Accordingly, the therapeutic compound can have the formula:

[AH]-(SP)$_n$-[EG]

wherein AH is a moiety that antagonizes a histamine receptor or a collection of histamine receptors, EG is an ester group that modifies the half-life of the therapeutic compound, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[CA]-(SP)n-[DA]

wherein CA is a moiety that modulates an active CNS target receptor or a collection of active CNS target receptors, DA is a drug activity modulating moiety that provides the ability to modulate the activity of the therapeutic compound, e.g., ester or carboxylic acid, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[CA]-(SP)n-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[AD]-(SP)n-[EG]

wherein AD is a moiety that agonizes an adenosine receptor or a collection of adenosine receptors, EG is an ester group that modifies the half-life of the therapeutic compound, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[AH]-(SP)n-[DA]

wherein AH is a moiety that antagonizes a histamine receptor or a collection of histamine receptors, DA is a drug activity modulating moiety that provides the ability to modulate the activity of the therapeutic compound, e.g., ester or carboxylic acid, SP is a spacer molecule, and n is 0 or 1.

Another aspect of the invention is a method of modulating a sleep disorder target. The method comprises administering an effective amount of a therapeutic compound to a subject, such that the sleep disorder target is modulated, wherein the therapeutic compound comprises the formula:

[AH]-(SP)n-[EG]

wherein AH is a moiety that antagonizes a histamine receptor or a collection of histamine receptors, EG is an ester group that modifies the half-life of the therapeutic compound, SP is a spacer molecule, and n is 0 or 1.

One aspect of the invention is a Central Nervous System (CNS) disorder target modulator comprising the formula:

[CA]-(SP)n-[DA]

wherein CA is a moiety that modulates an active CNS target receptor or a collection of active CNS target receptors, DA is a drug activity modulating moiety that provides the ability to modulate the activity of the therapeutic compound, e.g., ester or carboxylic acid, SP is a spacer molecule, and n is 0 or 1.

Another aspect of the invention is a CNS disorder target modulator comprising the formula:

[CA]-(SP)n-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

Another aspect of the invention is a sleep disorder target modulator comprising the formula:

[CA]-(SP)n-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

In a another aspect of the invention a sleep disorder target modulator comprises the formula:

[AH]-(SP)n-[DA]

wherein AH is a moiety that antagonizes a histamine receptor, DA is a drug activity modulating moiety that provides the ability to modulate the activity of the therapeutic compound, e.g., ester or carboxylic acid, SP is a spacer molecule, and n is 0 or 1.

In a particular aspect of the invention a sleep disorder target modulator comprises the formula:

[AH]-(SP)n-[EG]

wherein AH is a moiety that antagonizes a histamine receptor, EG is an ester group that modifies the half-life of the therapeutic compound, SP is a spacer molecule, and n is 0 or 1.

Another aspect of the invention is a pharmaceutical composition comprising a therapeutic compound as prepared according to the methodology of this invention, and a pharmaceutically acceptable carrier.

DETAILED DESCRIPTION OF THE INVENTION

Figure 1A:
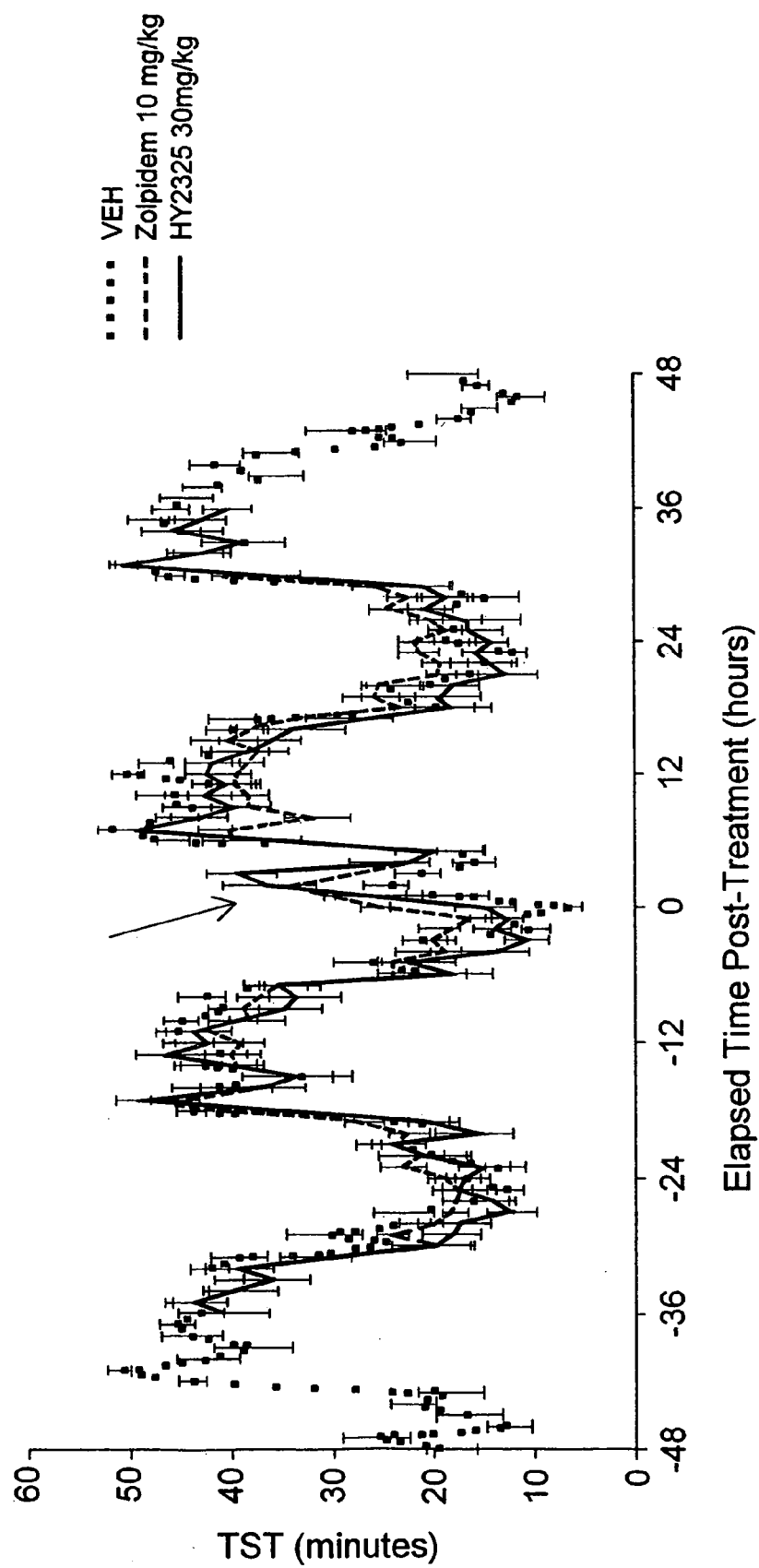
FIGS. 1A–C are graphs depicting the effect of a compound of the invention on parameters pertinent to sleep disorders.

The invention is directed to compositions used for treating Central Nervous System (CNS) disorders. In addition, the invention provides convenient methods of treatment of a CNS disorder. Furthermore, the invention provides methods of treating sleep disorders using compositions that remain active for a discrete period of time to reduce side effects. More specifically, the invention is directed to the compositions and use of derivatized, e.g., ester or carboxylic acid derivatized, antihistamine antagonists for the treatment of sleep disorders.

Methods of the Invention

One embodiment of the invention is a method of treating a Central Nervous System (CNS) disorder. The method of treating comprises the treatment of a Central Nervous System (CNS) disorder, comprising administering to a subject an effective amount of a therapeutic compound, such that the therapeutic compound penetrates into the CNS and modulates the CNS target, thereby treating the CNS disorder.

The language "Central Nervous System (CNS) disorder,' includes disorders or states of the central nervous system and that are treatable by the compounds described herein. Examples include, but are not limited to depression; anxiety; addictions; obsessive compulsive disorder; affective neurosis/disorder; depressive neurosis/disorder; anxiety neurosis; dysthymic disorder; behavior disorder; mood disorder; sexual dysfunction; psychosexual dysfunction; sex disorder; sexual disorder; schizophrenia; manic depression; delirium; dementia; severe mental retardation and dyskinesias such as Huntington" disease and Gilles de la Tourett's syndrome; disturbed biological and circadian rhythms; feeding disorders, such as anorexia, bulimia, cachexia, and obesity; diabetes; appetite/taste disorders; vomiting/nausea; asthma; cancer; Parkinson's disease; Cushing's syndrome/disease; basophil adenoma; prolactinoma; hyperprolactinemia; hypopituitarism; hypophysis tumor/adenoma; hypothalamic diseases; Froehlich's syndrome; adrenohypophysis disease; hypophysis tumor/adenoma; pituitary growth hormone; adrenohypophysis hypofunction; adrenohypophysis hyperfunction; hypothalamic hypogonadism; Kallman's syndrome (anosmia, hyposmia); functional or psychogenic amenorrhea; hypopituitarism; hypothalamic hypothyroidism; hypothalamic-adrenal dysfunction; idiopathic hyperprolactinemia; hypothalamic disorders of growth hormone deficiency; idiopathic growth hormone deficiency; dwarfism; gigantism; acromegaly; disturbed biological and circadian rhythms; and sleep disturbances associated with such diseases as neurological disorders, neuropathic pain and restless leg syndrome, heart and lung diseases; acute and congestive heart failure; hypotension; hypertension; urinary retention; osteoporosis; angina pectoris; myocardial infarction; ischaemic or haemorrhagic stroke; subarachnoid haemorrhage; head injury such as subarachnoid haemorrhage associated with traumatic head injury; ulcers; allergies; benign prostatic hypertrophy; chronic renal failure; renal disease; impaired glucose tolerance; migraine; hyperalgesia; pain; enhanced or exaggerated sensitivity to pain, such as hyperalgesia, causalgia and allodynia; acute pain; burn pain; atypical facial pain; neuropathic pain; back pain; complex regional pain syndromes I and II; arthritic pain; sports injury pain; pain related to infection, e.g., HIV, post-polio syndrome, and post-herpetic neuralgia; phantom limb pain; labor pain; cancer pain; post-chemotherapy pain; post-stroke pain; post-operative pain; neuralgia; conditions associated with visceral pain including irritable bowel syndrome, migraine and angina; urinary bladder incontinence e.g. urge incontinence; tolerance to narcotics or withdrawal from narcotics; sleep disorders, sleep apnea; narcolepsy, insomnia; parasomnia; jet-lag syndrome; and neurodegenerative disorders, which include nosological entities such as disinhibition-dementia-parkinsonism-amyotrophy complex; pallido-ponto-nigral degeneration, epilepsy and seizure disorders, attention-deficit hyperactivity disorder (ADHD)/cognition, Alzheimer's, drug abuse, stroke, multiple sclerosis (MS), and Amyotrophic Lateral Sclerosis (ALS).

The terms "treating" or "treatment" include administering a therapeutically effective amount of a compound sufficient to reduce or eliminate at least one symptom of the state, disease or disorder, e.g, a sleep disorder.

The language "administering" includes delivery to a subject by any means that does not affect the ability of the therapeutic compound to perform its intended function. The therapeutic compound may be administered by any means that sufficiently treats the disorder target. Administration includes, but is not limited to parenteral, enteral, and topical administration. While it is possible for a compound of the present invention to be administered alone, it is preferable to administer the compound as a pharmaceutical composition, which includes compositions that comprise the compounds of the present invention and a pharmaceutically acceptable carrier. In a specific embodiment, the therapeutic compound is administered orally.

Administration also includes the use of an additional modulating factor (AMF) in "combination therapy." The language "additional modulating factor (AMF)" includes additional factors, such as additional therapeutics or subject abnormalities, e.g., a chemical imbalance. It should be understood that the additional modulating factor may be directed to the same or a different disorder target as that being modulated by the compounds of the present invention. The language "combination therapy" includes the co-administration of the modulating compound of the present invention in the presence of an additional modulating factor, e.g., an additional therapeutic agent. Administration of the modulating compound may be first, followed by the other therapeutic agent; or administration of the other therapeutic agent may be first, followed by the modulating, e.g., inhibiting, compound. The other therapeutic agent may be any agent which is known in the art to treat, prevent, or reduce the symptoms of the targeted disorder, e.g., a sleep disorder. In addition, the compounds of the present invention can also be administered in combination with other known therapies for the target disorder. Furthermore, the other therapeutic agent may be any agent of benefit to the patient when administered in combination with the administration of a modulating, e.g., inhibiting, compound. The other therapeutic agent may also be a modulating compound. For example, a therapeutic compound of the invention may be administered in conjunction with a variety of commercially-available drugs, including, but not limited to, antimicrobial agents, such as pentamidine, lomefloxacin, metronidazole, fungistatic agents, germicidal agents, hormones, antipyretic agents, antidiabetic agents, bronchodilators, such as aminophylline, antidiarrheal agents, such as diphenoxylate hydrochloride with atropine sulfate, antiarrhythmic agents, such as disopyramide phosphate and bidisomide, coronary dilation agents, glycosides, spasmolytics, antihypertensive agents, such as verapamil and verapamil hydrochloride and their enantiomers, and betaxolol, antidepressants, antianxiety agents, other psychotherapeutic agents, such as zolpidem, cycloserine and milacemide, corticosteroids, analgesics, such as misoprostol with diclofenac, contraceptives, such as ethynodiol diacetate with ethinyl estradiol, and norethynodrel with mestranol, nonsteroidal anti-inflammatory drugs, such as oxaprozen, blood glucose lowering agents, cholesterol lowering agents, anticonvulsant agents, other antiepileptic agents, immunomodulators, antioholinergics, sympatholytics, sympathomimetics, vasodilatory agents, anticoagulants, antiarrhythmics, such as disopyramide or disobutamide, prostaglandins having various pharmacologic activities, such as misoprostol and enisoprost, diuretics, such as spironolactone and spironolactone with hydrochlorothiazide, sleep aids, such as zolpidem tartrate, antihistaminic agents, antineoplastic agents, oncolytic agents, antiandrogens, antimalarial agents, antileprosy agents, and various other types of drugs. See Goodman and Gilman's The Basis of Therapeutics (Eighth Edition, Pergamon Press, Inc., USA, 1990) and The Merck Index (Eleventh Edition, Merck & Co., Inc., USA, 1989), each of which is incorporated herein by reference In addition, a compound of the invention also may be administered in conjunction with any one or combination of the commercially-available, over-the-counter or prescription medications, including, but not limited to Avobenzene/padimate-O, ACCUPRIL® tablets (quinapril hydrochloride), Accutane capsules (isotretinoin), Achromycin V capsules (the monohydrochloride of (4S-(4.alpha., 4a.alpha., 5a.alpha.,6.beta., 12a.alpha.,))-4-(dimethylamino)-1,4,4a,5, 5a,6,11,12a-octBPydro-3,6,10,12,12a-pentBPydroxy-6-methyl-1,11-dioxo-2-naphthacenecarboxamide), Actifed cough syrup (codeine phosphate, triprolidine hydrochloride and pseudoephedrine hydrochloride), Aldactazide tablets (spironolactone and hydrochlorothiazide), ALDOCLOR®) tablets (methyldopa and chlorothiazide), Aldoril tablets (methyldopa-hydrochlorothiazide), Alferon® N injection (interferon .alpha.-n3 (human leukocyte derived)), ALTAC™ capsules (ramipril), AMBIEN® tablets (zolpidem tartrate), Anafranil capsules (clomipramine hydrochloride), ANAPROX® tablets (naproxen sodium), Ancobon capsules (flucytosine), Ansaid tablets (flurbiprofen), Apresazide capsules (hydralazine hydrochloride and hydrochlorothiazide), Asendin tablets (2-chloro-11-(1-piperazinyl)dibenz(b,f)(1, 4)-oxazepine), Atretol™ tablets (carbamazepine), Aureomycin ophthalmic ointment (chlortetracycline hydrochloride), Azo Gantanol® tablets (sulfamethoxazole and phenazopyridine hydrochloride), Azo Gantrisin tablets (sulfisoxazole and phenazopyridine hydrochloride), Azulfidine® tablets and EN-tabs (5-((p-(2-pyridylsulfamoyl)phenyl)-azo)salicylic acid), Bactrim tablets (trimethoprim and sulfamethoxazole), Bactrim I.V. infusion (trimethoprim and sulfamethoxazole), Bactrim pediatric suspension (trimethoprim and sulfamethoxazole), Bactrim suspension (trimethoprim and sulfamethoxazole), Bactrim tablets (trimethoprim and sulfamethoxazole), Benadryl® capsules (diphenhydramine hydrochloride USP), Benadryl® kapseals (diphenhydramine hydrochloride USP), Benadryl® tablets (diphenhydramine hydrochloride USP), Benadry® parenteral (diphenhydramine hydrochloride USP), Benadry® steri-vials, ampoules, and steridose syringe (diphenhydramine hydrochloride USP), Capoten tablets (captopril), Capozide tablets (captopril-hydrochlorothiazide), Cardizem® CD capsules (diltiazem hydrochloride), Cardizem® SR capsules (diltiazem hydrochloride), Cardizem® tablets (diltiazem hydrochloride), Chibroxin sterile ophthalmic solution (with oral form) (norfloxacin), Children's Advil® suspension (ibuprofen), Cipro® I.V. (ciprofloxacin), Cipro) tablets (ciprofloxacin), Claritin tablets (loratadine), Clinoril tablets (sulindac), Combipres® tablets (clonidine hydrochloride and chlorthalidone), Compazine® injection (prochlorperazine maleate), Compazine® multi-dose vials (prochlorperazine maleate), Compazine® syringes (prochlorperazine maleate), Compazine® spansule capsules (prochlorperazine maleate), Compazine® suppositories (prochlorperazine maleate), Compazine®) syrup (prochlorperazine maleate), Compazine® tablets (prochlorperazine maleate), Cordarone tablets (amiodarone hydrochloride), Corzide tablets (nadolol and bendroflumethiazide), Dantrium capsules (dantrolene sodium), Dapsone tablets (4-4' diaminodiphenylsulfone), DAYPRO® caplets (oxaproxin), Declomycin tablets (demeclacycline or (4S-(4.alpha., 4a.alpha.,5a.alpha.,6.beta., 12a.alpha.))-7-Chloro-4-dimethyl amino)-1,4,4a,5,5a,6,11, 12a-octBPydro-3,6,10,12,12a-pentBPydroxy-1,11-dioxo-2-naphthacenecarboxamide monohydrochloride), DECONAMINE® capsules (chlorpheniramine maleate and d-psuedoephedrine hydrochloride), DECONAMINE® syrup (chlorpheniramine maleate and d-psudoephedrine hydrochloride), DECONAMINE® tablets (chlorpheniramine maleate and d-psudoephedrine hydrochloride), Depakene capsules (valproic acid), Depakene syrup (valproic acid), Depakote sprinkle capsules (divalproex sodium), Depakote tablets (divalproex sodium), DiaBeta® tablets (glyburide), Diabinese tablets (chlorpropamide), Diamox parenteral (acetazolamide), Diamox sequels (acetazolamide), Diamox tablets (acetazolamide), Dimetane-DC cough syrup (brompheniramine maleate, phenylpropanolamine hydrochloride and codeine phosphate), Dimetane-DX cough syrup (brompheniramine maleate, phenylpropanolamine hydrochloride and codeine phosphate), Dipentum® capsules (olsalazine sodium), Diucardin tablets (hydroflumethiazide), Diupres tablets (reserpine and chlorothiazide), Diuril oral suspension (chlorothiazide), Diuril sodium intravenous (chlorothiazide), Diuril tablets (chlorothiazide), Dolobid tablets (diflunisal), DORYX® capsules (doxycycline hyclate), Dyazide capsules (hydrochlorothiazide and triamterene), Dyrenium capsules (triamterene), Efudex cream (5-fluorouracil), Efudex solutions (5-fluorouracil), Elavil injection (amitriptyline HCl), Elavil tablets (amitriptyline HCl), Eldepryl tablets (selegiline hydrochloride), Endep tablets (amitriptyline HCl), Enduron tablets (methyclothiazide), Enduronyl Forte tablets (methyclothiazide and deserpidine), Enduronyl tablets (methyclothiazide and deserpidine), Ergamisol tablets (levamisole hydrochloride), Esidrix tablets (hydrochlorothiazide USP), Esimil tablets (guanethidine monosulfate USP and hydrochlorothiazide USP), Etrafon Forte tablets (perphenazine, USP and amitriptyline hydrochloride, USP), Etrafon 2-10 tablets (perphenazine, USP and amitriptyline hydrochloride, USP), Etrafon tablets (perphenazine, USP and amitriptyline hydrochloride, USP), Etrafon-A tablets (perphenazine, USP and amitriptyline hydrochloride, USP), Eulexin capsules (flutamide), Exna tablets (benzthiazide), FUDR injection (floxuridine), Fansidar tablets (N1-(5,6-dimethoxy-4-pyrimidinyl) sulfanilamide (sulfadoxine) and 2,4-diamino-5-(p-chlorophenyl)-6-ethylpyrimidine (pyrimethamine), Feldene capsules (piroxicam), Flexeril tablets (cyclobenzaprine hydrochloride), FLOXIN® I.V. (ofloxacin injection), FLOXINS® tablets (ofloxacin), Fluorouracil injection (5-fluoro-2,4 (1H, 3H)-pyrimidinedione), Fulvicin tablets (griseofulvin), Gantanol(t suspension (sulfamethoxazole), Gantanol® tablets (sulfamethoxazole), Gantrisin ophthalmic ointment/solution (sulfisoxazole), Gantrisin pediatric suspension (sulfisoxazole), Gantrisin syrup (sulfisoxazole), Gantrisin tablets (sulfisoxazole), Glucotrol tablets (glipizide), Glynase PresTab tablets (glyburide), Grifulvin V tablets (griseofulvin), Grifulvin oral suspension (griseofulvin), Gristactin capsules (griseofulvin), Grisactin tablets (griseofulvin), Gris-PEG tablets (griseofulvin), Grivate tablets (griseofulvin), Grivate suspension (griseofulvin), Haldol Decanoate 50 injection (haloperidol decanoate), Haldol Decanoate 100 injection (haloperidol decanoate), Haldol tablets (haloperidol decanoate), Hibistat germicidal hand rinse (chlorhexidine gluconate), HISMANAL® tablets (astemizole), HydroDIURIL tablets (hydrochlorothiazide), Hydromox tablets (quinethazone), Hydropres tablets (reserpine and hydrochlorothiazide), Inderide® tablets (propranolol hydrochloride and hydrochlorothiazide), Inderides capsulet® (propranolol hydrochloride and hydrochlorothiazide), Intal inhaler (cromolyn sodium), Intron A injection (recombinant interferon .alpha.-2b), Lamprene capsules (clofazimine), Lasix oral solution (furosemide), Lasix tablets (furosemide), Lasix injection (furosemide), Limbitrol tablets (chlordiazepoxide and amitriptyline hydrochloride), Lodine capsules (etodolac), Lopressor HCT tablets (metoprolol tartrate USP and hydrochlorothiazide USP), Lotensin tablets (benazepril hydrochloride), LOZOL® tablets (indapamide), Ludiomil tablets (maprotiline hydrochloride USP), Marplan tablets (isocarboxazid), MAXAQUIN® tablets (lomefloxacin HCl), Maxzide tablets (triamterene USP and hydrochlorothiazide USP), Mellaril® concentrate (thioridazine), Mellaril® tablets (thioridazine), Mellaril-S suspension (thioridazine), Mepergan injection (meperidine hydrochloride and promethazine hydrochloride), Methotrexate tablets (methotrexate), Mevacor tablets (lovastatin), Micronase tablets (glyburide), Minizide capsules (prazosin hydrochloride and polythiazide), Minocin intravenous ((4S-(4.alpha.,4a.alpha.,5a.alpha., 12a.alpha.))-4,7-bis(dimethylamino)- 1,4,4a,5,5a,6,11,12a-octBPydro-3,10,12,12a-tetrBPydroxy-1,11-dioxo-2-naphthace necarboxamide monohydrochloride), Minocin oral suspension ((4S-(4.alpha., 4a.alpha.,5a.alpha.,12a.alpha.))-4,7-bis(dimethylamino)-1,4,4a,5,5a,6,11,12a-octB-Pydro-3,10,12,12a-tetrBPydroxy-1,11-dioxo-2-naphthacenecarboxamide monohydrochloride), Minocin capsules ((4S-(4.alpha.,4a.alpha.,5a.alpha.,12a,alpha.))-4,7-bis (dimethylamino)-1,4,4a,5a,6,11,12a -octBPydro-3,10,12,12a-tetrBPydroxy-1,11-dioxo-2-nalpthace necarboxamide monohydrochloride), Moduretic tablets (amiloride HCl-hydrochlorothiazide), Monodox® capsules (doxycycline monohydrate), Monopril tablets (fosinopril sodium), Children's Motrin liquid suspension (ibuprofen), Motrin tablets (ibuprofen), Mykrox tablets (metolazone), NAPROSYN® suspension (naproxen), NAPROSYN® tablets (naproxen), Navane capsules (thiothixene), Navane intramuscular (thiothixene), NegGram caplets (nalidixic acid), NegGram suspension (nalidixic acid), Neptazane tablets (methazolamide), Nipent injection (pentostatin), Normodyne tablets (labetalol HCl), NOROXIN tablets (norfioxacin), Norpramin tablets (desipramine hydrochloride USP), oretic tablets (hydrochlorothiazide), Oreticyl Forte tablets (hydrochlorothiazide and deserpidine), Orinase tablets (tolbutamide), Ornade capsules (phenylpropanolamine hydrochloride and chlorpheniramine maleate), Orudis capsules (ketoprofen), Oxsoralen lotion (methoxypsoralen), PBZ tablets (tripelennamine hydrochloride USP), PBZ-SR tablets (tripelennamine hydrochloride USP), pHisoHex topical emulsion (hexachlorophene), P & S PLUS® topical tar gel (crude coal tar), Pamelor® capsules (nortriptyline HCl), Pamelor® solution (nortriptyline HCl), Paxil tablets (paroxetine hydrochloride), Pediazole oral suspension (erythromycin ethylsuccinate, USP and sulfisoxazole acetyl, USP), Penetrex.TM. tablets (enoxacin), Pentasa capsules (mesalamine), Periactin syrup (cyproheptadine HCl), Periactin tablets (cyproheptadine HCl), Phenergan tablets (promethazine hydrochloride), Phenergan injection (promethazine hydrochloride), Phenergan suppositories (promethazine hydrochloride), Phenergan syrup (promethazine hydrochloride), Polytrim® ophthalmic solution (trimethoprim sulfate and polymyxin B sulfate), Pravachol (pravastatin sodium), Prinivil® tablets (lisinopril, MSD), Prinzide tablets (lisinopril-hydrochlorothiazide), Prolixin elixir (fluphenazine hydrochloride), Prolixin enanthate (fluphenazine hydrochloride), Prolixin injection (fluphenazine hydrochloride), Prolixin oral concentrate (fluphenazine hydrochloride), Prolixin tablets (fluphenazine hydrochloride), ProSom tablets (estazolam), Prozac® oral solution (fluoxetine hydrochloride), Prozac® oral Pulvules® (fluoxetine hydrochloride), Pyrazinamide tablets (pyrazinamide), QUINAGLUTE® tablets (quinidine gluconate), Quinidex tablets (quinidine sulfate), Relafen tablets (nabumetone), Ru-Tuss II capsules (chlorpheniramine maleate and phenylpropanolamine hydrochloride), Seldane tablets (terfenadine), Septra tablets (trimethoprim and sulfamethoxazole), Septra suspension (trimethoprim and sulfamethoxazole), Septra I.V. infusion (trimethoprim and sulfamethoxazole), Septra tablets (trimethoprim and sulfamethoxazole), Ser-Ap-Es tablets (reserpine USP, hydralazine hydrochloride USP and hydrochlorothiazide USP), Sinequan capsules (doxepin HCl), Solganal injection (aurothioglucose, USP), Stelazine concentrate (trifluoperazine hydrochloride), Stelazine injection (trifluoperazine hydrochloride), Stelazine tablets (trifluoperazine hydrochloride), Surmontil capsules (trimipramine maleate), SYMMETREL capsules and syrup (amantadine hydrochloride), Taractan concentrate (chlorprothixene), Taractan injectable (chlorprothixene), Taractan tablets (chlorprothixene), TAVIST® syrup (clemastine fumarate, USP), TAVIST® tablets (clemastine fumarate, USP), TAVIST®-1 12 hour relief medicine (clemastine fumarate, USP), TAVIST®-D 12 hour relief medicine (clemastine fumarate, USP), Tegretol Tablets (carbamazepine USP), Tegretol suspension (carbamazepine USP), Temaril tablets (trimeprazine tartrate), Temaril syrup (trimeprazine tartrate), Temaril capsules (trimeprazine tartrate), TENORETIC® tablets (atenolol and chlorthalidone), Terramycin intramuscular solution (oxytetracycline), Thiosulfil Forte tablets (sulfamethizole), Thorazine ampuls (chlorpromazine hydrochloride), Thorazine concentrate (chlorpromazine hydrochloride), Thorazine multi-dose vials (chlorpromazine hydrochloride), Thorazine capsules (chlorpromazine hydrochloride), Thorazine suppositories (chlorpromazine hydrochloride), Thorazine syrup (chlorpromazine hydrochloride), Thorazine tablets (chlorpromazine hydrochloride), Timolide tablets (timolol maleate-hydrochlorothiazide), Tofranil ampuls (imipramine hydrochloride USP), Tofranil tablets (imipramine hydrochloride USP), Tofranil capsules (imipramine hydrochloride USP), Tolinase tablets (tolazamide), Triaminic Expectorant DH (phenylpropanolamine hydrochloride and guaifenesin), Triaminic oral infant drops (phenylpropanolamine hydrochloride, pheniramine maleate and pyrilamine maleate), Triavil tablets (perphenazine-amitriptyline HCl), Trilafon concentrate (perphenazine USP), Trilafon injection (perphenazine USP), Trilafon tablets (perphenazine, USP), Trinalin tablets (azatadine maleate, USP, and pseudoephedrine sulfate, USP), Vaseretic tablets (enalapril maleate-hydrochlorothiazide), Vasosulf opthalmic solution (sulfacetamide sodium-phenylephrine hydrochloride), Vasotec I.V. (enalapril maleate), Vasotec tablets (enalapril maleate), Velban® vials (vinblastine sulfate, USP), Vibramycin capsules (doxycycline monohydrate), Vibramycin intravenous (doxycycline monohydrate), Vibramycin oral suspension (doxycycline monohydrate), Vibra-Tabs tablets (oxytetracycline), Vivactil tablets (protriptyline HCl), Voltaren tablets (diclofenac sodium), X-SEB T® shampoo (crude coal tar), Zaroxolyn tablets (metolazone), ZESTORETIC® oral (lisinopril and hydrochlorothiazide), ZESTRIL® tablets (lisinopril), ZITHROM™ capsules (azithromycin), Zocor tablets (simvastatin), ZOLOFT® tablets (sertraline hydrochloride) and others.

A compound of the invention may also be administered in conjunction with the use of physical methods such as with light therapy or electrical stimulation.

The term "pharmaceutically acceptable carrier" include a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof, and coloring agents. ,In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include/pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents that delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Oral administration is preferred.

The terms "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The terms "systemic administration," "administered systematically," "peripheral administration" and "administered peripherally" as used herein mean the administration of a compound, drug or other material other than directly into the central nervous system, for example, subcutaneous administration, such that it enters the patient's system and thus, is possibly subject to metabolism and other like processes.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

The regimen of administration can affect what constitutes an effective amount. The disorder target modulators, e.g., CNS disorder target modulators, can be administered to the subject either prior to or after the onset of a CNS disorder associated state. Further, several divided dosages, as well as staggered dosages, can be administered daily or sequentially, or the dose can be continuously infused, or can be a bolus injection. Further, the dosages of the disorder target modulators, e.g., CNS disorder target modulators, compound(s) can be proportionally increased or decreased as indicated by the exigencies of the therapeutic or prophylactic situation.

The language "subject" includes animals (e.g., mammals, e.g., cats, dogs, horses, pigs, cows, sheep, rodents, rabbits, squirrels, bears, primates (e.g., chimpanzees, gorillas, and humans) which are capable of suffering from a CNS associated disorder, e.g., a sleep disorder.

The language "therapeutically effective amount" of the compound is that amount necessary or sufficient to treat or prevent a state associated with a disorder, e.g., CNS disorder. The effective amount can vary depending on such factors as the size and weight of the subject, the type of illness, or the particular compound. For example, the choice of the therapeutic compound can affect what constitutes an "effective amount". One of ordinary skill in the art would be able to study the aforementioned factors and make the determination regarding the effective amount of the therapeutic compound without undue experimentation.

The language "penetrates into the CNS" includes the favorable biological property of a compound of the current invention to pass though, or penetrate, the blood brain barrier (BBB) and enter into the CNS.

The language "therapeutic compound" includes compounds of the invention capable of performing their intended function, e.g., treating CNS disorders and/or modulating CNS targets. The therapeutic compounds of the invention are described in detail herein.

Accordingly, the therapeutic compound can have the formula:

$$[CA]\text{-}(SP)_n\text{-}[DA]$$

wherein CA includes moieties that modulate an active CNS target receptor or a collection of active CNS target receptors.

The language "drug activity modulating moiety", or "DA" is a moiety that provides the ability to modulate the activity of the therapeutic compound. Examples include functional moieties, e.g., ester, carboxylic acid or alcohol groups, selected and positioned within the therapeutic drug to provide the ability to modulate the activity of the drug, e.g., modulate, e.g., increase, the half-life of the drug, the ability of the drug to cross the blood brain barrier, or the ability of the drug to bind selectively to the desired receptor. In certain embodiments of the invention, the drug activity modulating moiety is an ester group, EG. In particular embodiments, the activity of the drug, e.g., half-life, of the therapeutic drug is modulated by controlling the rate of hydrolysis of the ester group by selection and positioning of steric bulk near the ester carbonyl of the ester group. In certain embodiments, the steric bulk is provided by the selection of a bulky ester group. In alternative embodiments the steric bulk is provided by substitution selected and positioned on the CA moiety, e.g., an AH moiety, near the carbonyl of the ester group.

In a specific embodiment, the drug activity modulating moiety is a carboxylic acid. In certain embodiments of the invention, the presence of the carboxylic acid results in increased concentration of the therapeutic compound within the CNS for a discrete period of time as a result of the existence of an ionic bond that includes the carboxylate ion of the corresponding carboxylic acid, e.g., zwitterion species formation with a nitrogen atom within the compound or salt bridge formation. In one embodiment, penetration through the blood brain barrier into the CNS results from the lipophilicity of substituents or conformational lipophilicity, i.e., lipophilicity as a result of a particular conformation, such as internal salt formation between a carboxylate anion and a protonated amine. In another embodiment, the presence of the carboxylic acid improves the ability of the compound to bind selectively to the desired receptor.

The language "ester group" includes an organic ester functionality that is selected and positioned within the compound providing the ability to modulate the activity or modify the properties of the corresponding therapeutic compound. The organic ester group may be terminal, e.g., a substituent, or internal. The carboxylate of the ester may be oriented from left to right or from right to left, e.g., a reverse ester. Examples of esters of the current invention include, but are not limited to hydrocarbons and perfluorocarbons. In a preferred embodiment, the hydrocarbons posses 1 to 20 carbons. In certain embodiments, the hydrocarbons can be linear, branched, cyclic, aromatic, and a combination of aliphatic and aromatic, which are optionally substituted with O, N, S, and/or halogens and may additionally include a center of chirality. In particular embodiments, the ester can be an n-propyl, an isopropyl, a t-butyl, a cyclopentyl, a cyclohexyl, a cycloheptyl, and a benzyl group.

The language "bulky ester" is intended to include an ester that has sufficient steric properties such that the rate of hydrolysis of the therapeutic compound is modulated, e.g., reduced, such that the activity of the therapeutic compound is modified, e.g., the length of activity is increased (i.e., the half-life of the therapeutic compound is increased). Examples of bulky ester groups are depicted in Table 1.

TABLE 1

Bulky Groups For H1 Antagonist Esters

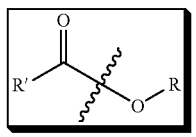

R' = Parent Drug Core Structure
R = Ester from Alcohols below

TYPE A:

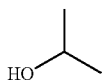 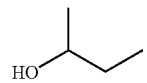 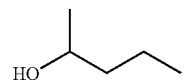

TYPE B:

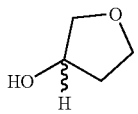 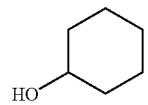 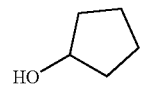

Aldrich as R,S mixture
and pure R or S enantiomers.
Prepare esters with R,S mixture first.

Aldrich

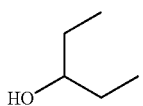 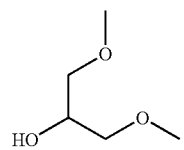 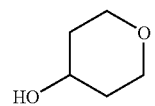

Aldrich 1,3-dimethoxy-2-propanol
Tyger Scientific Inc.
Ewing, NJ

Aldrich

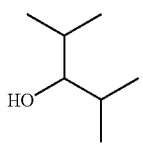 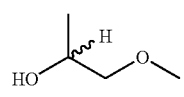 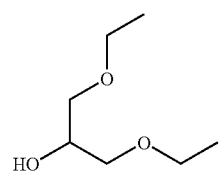

Aldrich

Aldrich as R,S mixture
Acros as pure R or S enantiomers.
Prepare esters with R,S mixture first.

Lancaster or TCI

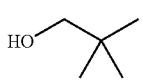

Aldrich

In certain embodiments, the ester is not methyl, ethyl, or n-propyl. In certain embodiments of the invention, the bulky ester is not an n-propyl, isopropyl, n-butyl, isobutyl, or tert-butyl ester. In certain embodiments of the invention, the ester is not a C-1 to C-4 ester. In certain embodiments of the invention wherein the therapeutic compound is a diphenhydramine-like, triprolidine-like, and doxepin-like compound, the ester is not a C-1 to C-4 ester and/or a C-3 to C-4 bulky ester.

The language "hydrocarbon" as used herein, includes substituted or unsubstituted alkyl, alkenyl, alkynyl, and aromatic or aryl moieties. The term "alkyl" includes saturated aliphatic groups, including straight-chain alkyl groups (e.g., methyl, ethyl, propyl, butyl, pentyl, hexyl, heptyl, octyl, nonyl, decyl, etc.), branched-chain alkyl groups (isopropyl, tert-butyl, isobutyl, etc.), cycloalkyl (alicyclic) groups (cyclopropyl, cyclopentyl, cyclohexyl, cycloheptyl, cyclooctyl), alkyl substituted cycloalkyl groups, and cycloalkyl substituted alkyl groups. The term alkyl further includes alkyl groups, which can further include oxygen, nitrogen, sulfur or phosphorous atoms replacing one or more carbons of the hydrocarbon backbone. In certain embodiments, a straight chain or branched chain alkyl has 6 or fewer carbon atoms in its backbone (e.g., $C_1$–$C_6$ for straight chain, $C_3$–$C_6$ for branched chain), and more preferably 4 or fewer. Likewise, preferred cycloalkyls have from 3–8 carbon atoms in their ring structure, and more preferably have 5 or 6 carbons in the ring structure. The term $C_1$–$C_6$ includes alkyl groups containing 1 to 6 carbon atoms.

Moreover, the term alkyl includes both "unsubstituted alkyls" and "substituted alkyls". the latter of which refers to alkyl moieties having substituents replacing a hydrogen on one or more carbons of the hydrocarbon backbone. Such substituents can include, for example, alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Cycloalkyls can be further substituted, e.g., with the substituents described above. An "alkylaryl" or an "aralkyl" moiety is an alkyl substituted with an aryl (e.g., phenylmethyl (benzyl)). The term "alkyl" also includes the side chains of natural and unnatural amino acids.

The term "aryl" includes groups, including 5- and 6-membered single-ring aromatic groups that may include from zero to four heteroatoms, for example, benzene, phenyl, pyrrole, furan, thiophene, thiazole, isothiaozole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminoacarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkyl amino, dialkylamino, arylamino,-diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings which are not aromatic so as to form a polycycle (e.g., tetralin).

The term "alkenyl" includes unsaturated aliphatic groups analogous in length and possible substitution to the alkyls described above, but that contain at least one double bond.

For example, the term "alkenyl" includes straight-chain alkenyl groups (e.g., ethenyl, propenyl, butenyl, pentenyl, hexenyl, heptenyl, octenyl, nonenyl, decenyl, etc.), branched-chain alkenyl groups, cycloalkenyl (alicyclic) groups (cyclopropenyl, cyclopentenyl, cyclohexenyl, cycloheptenyl, cyclooctenyl), alkyl or alkenyl substituted cycloalkenyl groups, and cycloalkyl or cycloalkenyl substituted alkenyl groups. The term alkenyl further includes alkenyl groups which include oxygen, nitrogen, sulfur or phosphorous atoms replacing one or more carbons of the hydrocarbon backbone. In certain embodiments, a straight chain or branched chain alkenyl group has 6 or fewer carbon atoms in its backbone (e.g., $C_2$–$C_6$ for straight chain, $C_3$–$C_6$ for branched chain). Likewise, cycloalkenyl groups may have from 3–8 carbon atoms in their ring structure, and more preferably have 5 or 6 carbons in the ring structure. The term $C_2$–$C_6$ includes alkenyl groups containing 2 to 6 carbon atoms.

Moreover, the term alkenyl includes both "unsubstituted alkenyls" and "substituted alkenyls", the latter of which refers to alkenyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "alkynyl" includes unsaturated aliphatic groups analogous in length and possible substitution to the alkyls described above, but which contain at least one triple bond.

For example, the term "alkynyl" includes straight-chain alkynyl groups (e.g., ethynyl, propynyl, butynyl, pentynyl, hexynyl, heptynyl, octynyl, nonynyl, decynyl, etc.), branched-chain alkynyl groups, and cycloalkyl or cycloalkenyl substituted alkynyl groups. The term alkynyl further includes alkynyl groups which include oxygen, nitrogen, sulfur or phosphorous atoms replacing one or more carbons of the hydrocarbon backbone. In certain embodiments, a straight chain or branched chain alkynyl group has 6 or fewer carbon atoms in its backbone (e.g., $C_2$–$C_6$ for straight chain, $C_3$–$C_6$ for branched chain). The term $C_2$–$C_6$ includes alkynyl groups containing 2 to 6 carbon atoms.

Moreover, the term alkynyl includes both "unsubstituted alkynyls" and "substituted alkynyls", the latter of which refers to alkynyl moieties having substituents replacing a hydrogen on one or more carbons of the hydrocarbon backbone. Such substituents can include, for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

Unless the number of carbons is otherwise specified, "lower alkyl" as used herein means an alkyl group, as defined above, but having from one to five carbon atoms in its backbone structure. "Lower alkenyl" and "lower alkynyl" have chain lengths of, for example, 2–5 carbon atoms.

The term "acyl" includes compounds and moieties that contain the acyl radical ($CH_3CO$—) or a carbonyl group. The term "substituted acyl" includes acyl groups where one or more of the hydrogen atoms are replaced by for example, alkyl groups, alkynyl groups, halogens, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety.

The term "acylamino" includes moieties wherein an acyl moiety is bonded to an amino group. For example, the term includes alkylcarbonylamino, arylcarbonylamino, carbamoyl and ureido groups.

The term "aroyl" includes compounds and moieties with an aryl or heteroaromatic moiety bound to a carbonyl group. Examples of aroyl groups include phenylcarboxy, naphthyl carboxy, etc.

The terms "alkoxyalkyl", "alkylaminoalkyl" and "thioalkoxyalkyl" include alkyl groups, as described above, which further include oxygen, nitrogen or sulfur atoms replacing one or more carbons of the hydrocarbon backbone, e.g., oxygen, nitrogen or sulfur atoms.

The term "alkoxy" includes substituted and unsubstituted alkyl, alkenyl, and alkynyl groups covalently linked to an oxygen atom. Examples of alkoxy groups include methoxy, ethoxy, isopropyloxy, propoxy, butoxy, and pentoxy groups. Examples of substituted alkoxy groups include halogenated alkoxy groups. The alkoxy groups can be substituted with groups such as alkenyl, alkynyl, halogen, hydroxyl, alkylcarbonyloxy, arylcarbonyloxy, alkoxycarbonyloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moieties. Examples of halogen substituted alkoxy groups include, but are not limited to, fluoromethoxy, difluoromethoxy, trifluoromethoxy, chloromethoxy, dichloromethoxy, trichloromethoxy, etc.

The term "amine" or "amino" includes compounds where a nitrogen atom is covalently bonded to at least one carbon or heteroatom. The term "alkyl amino" includes groups and compounds wherein the nitrogen is bound to at least one additional alkyl group. The term "dialkyl amino" includes groups wherein the nitrogen atom is bound to at least two additional alkyl groups. The term "arylamino" and "diarylamino" include groups wherein the nitrogen is bound to at least one or two aryl groups, respectively. The term "alkylarylamino," "alkylaminoaryl" or "arylaminoalkyl" refers to an amino group that is bound to at least one alkyl group and at least one aryl group. The term "alkaminoalkyl" refers to an alkyl, alkenyl, or alkynyl group bound to a nitrogen atom that is also bound to an alkyl group.

The term "amide" or "aminocarboxy" includes compounds or moieties that contain a nitrogen atom that is bound to the carbon of a carbonyl or a thiocarbonyl group. The term includes "alkaminocarboxy" groups that include alkyl, alkenyl, or alkynyl groups bound to an amino group bound to a carboxy group. It includes arylaminocarboxy groups that include aryl or heteroaryl moieties bound to an amino group that is bound to the carbon of a carbonyl or thiocarbonyl group. The terms "alkylaminocarboxy," "alkenylaminocarboxy," "alkynylaminocarboxy," and "arylaminocarboxy" include moieties wherein alkyl, alkenyl, alkynyl and aryl moieties, respectively, are bound to a nitrogen atom which is in turn bound to the carbon of a carbonyl group.

The term "carbonyl" or "carboxy" includes compounds and moieties that contain a carbon connected with a double bond to an oxygen atom. Examples of moieties that contain a carbonyl include aldehydes, ketones, carboxylic acids, amides, esters, anhydrides, etc.

The term "thiocarbonyl" or "thiocarboxy" includes compounds and moieties that contain a carbon connected with a double bond to a sulfur atom.

The term "ether" includes compounds or moieties that contain an oxygen bonded to two different carbon atoms or heteroatoms. For example, the term includes "alkoxyalkyl" which refers to an alkyl, alkenyl, or alkynyl group covalently bonded to an oxygen atom which is covalently bonded to another alkyl group.

The term "thioether" includes compounds and moieties that contain a sulfur atom bonded to two different carbon or hetero atoms. Examples of thioethers include, but are not limited to alkthioalkyls, alkthioalkenyls, and alkthioalkynyls. The term "alkthioalkyls" include compounds with an alkyl, alkenyl, or alkynyl group bonded to a sulfur atom that is bonded to an alkyl group. Similarly, the term "alkthioalkenyls" and alkthioalkynyls" refer to compounds or moieties wherein an alkyl, alkenyl, or alkynyl group is bonded to a sulfur atom that is covalently bonded to an alkynyl group.

The term "hydroxy" or "hydroxyl" includes groups with an —OH or —O$^-$.

The term "halogen" includes fluorine, bromine, chlorine, iodine, etc. The term "perhalogenated," e.g., perfluorinated, generally refers to a moiety, e.g., perfluorocarbons, wherein all hydrogens are replaced by halogen atoms, e.g., fluorine.

The terms "polycyclyl" or "polycyclic radical" refer to two or more cyclic rings (e.g., cycloalkyls, cycloalkenyls, cycloalkynyls, aryls and/or heterocyclyls) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, alkylaminoacarbonyl, aralkylaminocarbonyl, alkenylaminocarbonyl, alkylcarbonyl, arylcarbonyl, aralkylcarbonyl, alkenylcarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkyl, alkylaryl, or an aromatic or heteroaromatic moiety.

The term "heteroatom" includes atoms of any element other than carbon or hydrogen. Preferred heteroatoms are nitrogen, oxygen, sulfur and phosphorus.

In certain embodiments, the ester group does not substantially effect the biological activity of the therapeutic compound. Alternatively, in certain other embodiments the ester group significantly effects the biological activity of the therapeutic compound. In one embodiment of the invention, the ester group improves the biological activity of the therapeutic compound.

When the ester is a methyl or an ethyl ester, the formulation of the therapeutic compound is formulated to sufficiently treat the target disorder. In addition, formulations of the therapeutic compound can be used to provide controlled in vivo adsorption of the therapeutic compound over a discrete period of time.

In certain embodiments of the invention, the compound containing the drug activity modulating group, e.g., an ester, carboxylic acid, or alcohol group, possesses an improved selectivity of the drug for a desired receptor versus an undesired receptors over the corresponding compound without this group. In certain embodiments of the invention, the compound containing the drug activity modulating group, e.g., an ester, carboxylic acid, or alcohol group, is more active as a therapeutic agent for treating disorders than the corresponding compound without this group. In specific embodiments, the ester is more active as a therapeutic agent for treating disorders than the corresponding acid of the ester. In particular embodiments, the corresponding acid of the ester is not a therapeutically active agent for treating disorders. In alternative embodiments, the corresponding acid of an ester is more active as a therapeutic agent for treating disorders than the corresponding ester of the acid. In a particular embodiment, the carboxylic acid drug activity modulating group provides an internal salt with an amine and facilitates crossing the blood brain barrier.

One skilled in the art would recognize that the ester groups, as described above, could be extended to thioesters. Labile amides may also be used in replacement of the ester group, wherein the in vivo hydrolysis would be performed by peptidases in the CNS.

The language "biological activity" includes activity associated with the intended biological function of the compounds of the present invention, e.g., treating a CNS disorder.

The language "modulate a target" or "modulation of a target" includes the act of agonizing or antagonizing a receptor or group of receptors of a target disorder. Thus, a compound that agonizes or antagonizes a receptor or group of receptors is referred to herein as a target modulator, e.g., CNS disorder target modulator. The language "target modulator" includes compounds or compositions, e.g., pharmaceutical compositions, which are used to modulate a target, e.g., a CNS disorder target, e.g., a sleep disorder target The terms "modification" or "modifies" include controlling or adjusting physical or chemical parameters, e.g., the half-life, of the therapeutic compound in vivo by changing one or more factors, e.g., the lipophilicity, electronic properties and/or steric size of the drug activity modulating moiety, e.g., ester group.

The language "spacer molecule" or "SP" includes molecules or moieties that are positioned within the compound to allow the compound to perform its intended function. In certain embodiments, the spacer molecule may be present. Alternatively, in certain other embodiments, the spacer molecule may not be present. In certain embodiments, the spacer molecule may be $(CH_2)_m$, where m is an integer number selected from 1 to 20. In addition, the spacer molecule, e.g., the $(CH_2)_m$ linker to an ester or a carboxylic acid group, can be substituted with one or more substituents. In one embodiment, the spacer molecule is mono-substituted. In another embodiment of the invention, the spacer molecule is disubstituted. In particular embodiments, the linkers of the invention may be geminally-dialkylated, e.g., gem-dimethylated, singly substituted with a substituent other than a noncyclic alkyl group, e.g., a heteroatom, or a cyclic substituent wherein one or more of the carbons of the spacer molecule is contained in the ring, e.g., heterocycle (e.g. tetrahydropyran or tetrahydrofuran), or cyclic alkyl, e.g., cyclopropyl. However, the substitution of the spacer molecule is independent of the substitution elsewhere in the molecule.

The term "target" includes a receptor or group of receptors that have been identified as useful point of action for a therapeutic compound, e.g., CNS target, e.g., sleep disorder target, e.g., histamine receptor.

The language "receptor" includes specific sites of binding or action within a subject, associated or responsible for the activity of the target disorder, e.g., a histamine or adenosine receptor.

The language "group of receptors" includes two or more receptors that may comprise the same receptor type or may comprise two or more receptor types.

In particular, the therapeutic compound of the invention may comprise the formula:

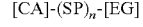
[CA]-(SP)$_n$-[EG]

wherein CA is a compound that modulates an active CNS target receptor or a collection of active CNS target receptors, EG is an ester group that modifies the half-life of the therapeutic compound, SP is a spacer molecule, and n is 0 or 1.

In certain embodiments, the CNS disorder is a sleep disorder. In particular embodiments of the current invention wherein the CNS disorder is a sleep disorder, the therapeutic compound of the invention may comprise one of the formulae:

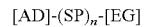
[AD]-(SP)$_n$-[EG]

[AH]-(SP)$_n$-[DA], or

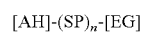
[AH]-(SP)$_n$-[EG]

wherein AH is a compound that antagonizes a histamine receptor or a collection of histamine receptors, AD is a compound that agonizes an adenosine receptor or a collection of adenosine receptors, DA is a drug activity modulating moiety that provides the ability to modulate the activity of the therapeutic compound, EG is an ester group that modifies the half-life of the therapeutic compound, SP is a spacer molecule, and n is 0 or 1.

The language "compounds that agonize" a receptor, e.g., agonizes an adenosine receptor, are intended to include compounds that induce the activity of the receptor and agents that up-regulate (i.e., induce) the synthesis or production of the receptor.

The language "compounds that antagonize" a receptor, e.g., a histamine receptor, are intended to include compounds that inhibit the activity of the receptor and agents that down-regulate (i.e., inhibit) the synthesis or production of the receptor.

The language "adenosine receptor agonist" is intended to include art recognized allosteric and nonallosteric adenosine receptor agonists, including, but not limited to cyclohexyladenosine, pentostatin, conformycin, and purine and adenyl derivatives that useful as adenosine precursors for the enhancement of adenosine synthesis. Adenosine has been reported to have cardioprotective and neuroprotective properties. It is reportedly released from cells in response to alterations in the supply of or demand for oxygen, is said to be a potent vasodilator, and is believed to be involved in the metabolic regulation of blood flow. However, adenosine has a short half-life (<1 sec) in human blood, and therefore high doses of adenosine would need to be administered continuously to achieve effective levels. However, high doses of adenosine have been reported to be toxic, and thus limit its therapeutic potential. It is also believed that by increasing adenosine concentration locally, i.e., at the target site within the target tissue, the beneficial effects of adenosine can be provided and the toxic systemic effects minimized. In certain embodiments of the invention, the therapeutic compounds of formula [AD]-(SP)$_n$-[EG], described above, may be used in the methods of the current invention to increase the local adenosine concentration.

The language "histamine antagonist," "antihistamine" and "[AH]" are used interchangeably and are intended to include any compound that antagonizes a histamine or group of histamine receptors. In certain embodiments, the compound of the invention will bind to a histamine receptor with an affinity of less than about 100 μM, e.g., less than about 10 μM. In one embodiment, antihistamines of the present invention contain at least two aryl rings that are separated by about 2–5 atoms from a basic nitrogen atom. In specific embodiments, the two aryl rings are connected to the same atom. The language "histamine antagonist" is intended to include art-recognized antihistamines, including both first and second generation antihistamines. For example, the antihistamines of the invention include, but are not limited to, antihistamines such as ethylenediamines, ethanolamines, alkylamines, phenothiazines, piperazines, piperdines, ketotifen, ebastine, terfenadine, acrivastine, triprolidine, doxepin, amitriptyline, trimipramine, protriptyline, nortriptyline, desipramine, pheniramine, diphenhydramine, mequitazine, cyproheptadine, clemastine, diphenylpyraline, promethazine, homochlorocyclizine, alimemazine, mepyramine, methapyraline, peroxatine, trazodone, nefazodone, hydroxyzine, meclizine loratidine, azelastine, levocabastine, cetirizine, fexofenadine, mizolastine, mirtazapine, and astemizole.

Classes of antihistamines of the instant invention also include pheniramine-like compounds, doxepin-like compounds, diphenhydramine-like compounds, triprolidine-like compounds, pheniramine analogs, and acrivastine analogs (see for example, Tables 2 and 3). It should be understood that the classes of antihistamines can be substituted or unsubstituted. In addition, the substituent(s) is selected and positioned within the molecule such that the compound is able to perform its intended function. Specific examples and locations of the substituents are discussed below.

The language "pheniramine-like compounds" is intended to include antihistamines that include two aryl groups linked to the same atom, not linked through a tricyclic ring system. In addition, pheniramine-like compounds are distinguished from diphenhydramine-like compounds by the lack of an oxygen atom linking the carbon atom, which is attached to the aryl groups, to a piperidine ring. In certain embodiments, the pheniramine-like compounds are represented by Formula (I) and Formula (II):

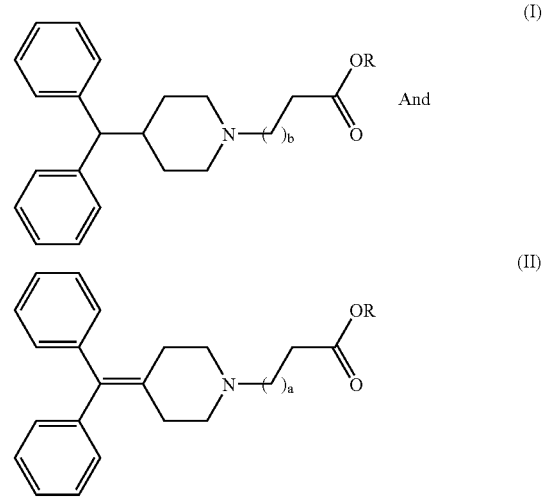

wherein a=0 through 5, b=0 through 5, and R is H or any group which imparts properties to the therapeutic compound to promote penetration into the CNS and to modify the half-life of the compound.

The language "diphenhydramine-like compounds" is intended to include antihistamines that include two aryl groups linked to the same atom, not linked through a tricyclic ring system, and are distinguished by the presence of an oxygen atom linking the carbon atom, which is attached to the aryl groups, to a piperidine ring. In certain embodiments, the diphenhydramine-like compounds are represented by Formula (III):

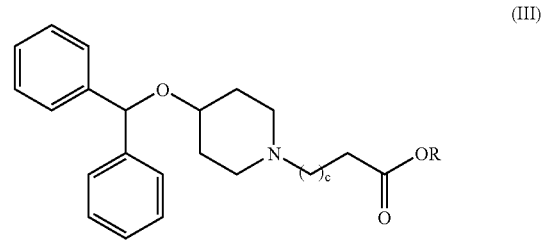

wherein c=0 through 5, and R is H or any group which imparts properties to the therapeutic compound to promote penetration into the CNS and to modify the half-life of the compound.

The language "doxepin-like compounds" is intended to include analogs of doxepine or antihistamines that include two aryl groups linked to the same atom that are linked through a tricyclic ring system, e.g. a seven membered ring (i.e., similar to that of doxepine). In addition, doxepin-like compounds may posses a piperidine ring or the ring can be replaced by a linear structure, e.g., an alkylene group (i.e., similar to that of doxepine). In certain embodiments, the doxepin-like compounds are represented by Formula (VI):

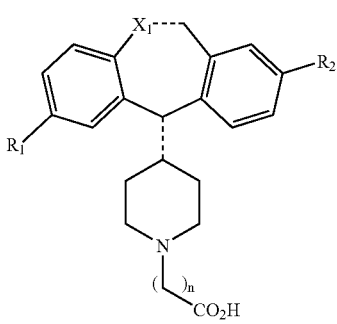

wherein the dashed line represents a single or double bond; $R_1$ and $R_2$ are substituents that are selected such that the compound can perform its intended function, e.g., substituents that are described for antihistamines; $X_1$ is O, S, or $CH_2$ and n 1 to 6. In one embodiment, n is 1 to 4. In a specific embodiment, n is 1, 2, or 3.

The language "triprolidine-like compounds" is intended to include antihistamines that include two aryl groups linked to the same atom, not linked through a tricyclic ring system, and are distinguished by the presence of a pyrrolidine ring. In certain embodiments, the triprolidine-like compounds are represented by Formula (IV):

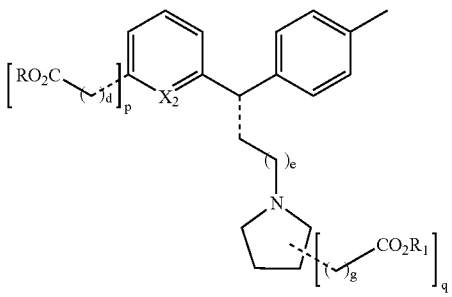

wherein d=0 through 5, e=0 through 4, g=0 through 5, the dashed line represents a single or double bond, R and $R_1$ are independently H or any group which imparts properties to the therapeutic compound to promote penetration into the CNS and to modify the half-life of the compound, and p and q are 0 or 1. In certain embodiments, p and q are not both 1. The $(CH_2)_m$ linker to the ester or carboxylic acid group, can be substituted with one or more substituents.

The language "acrivastine analogs" is intended to include the particular embodiment of Formula (IV), wherein the side chain that contains the $CO_2R$ is an acrylate, e.g., acrylic acid (as depicted in Scheme 1).

The language "pheniramine analogs" is intended to include antihistamines that include two aryl groups linked to the same atom, not linked through a tricyclic ring system. In addition, pheniramine analogs are distinguished by the presence of a dimethylamine moiety. In certain embodiments, the pheniramine analogs are represented by Formula (V):

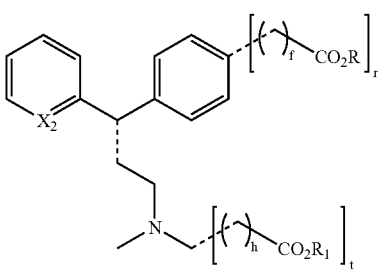

wherein f=0 through 5, h=0 through 5, the dashed line represents a single or double bond, R and $R_1$ are independently H or any group which imparts properties to the therapeutic compound to promote penetration into the CNS and to modify the half-life of the compound, $X_2$ is CH or N, and r and t are 0 or 1. In certain embodiments, r and t are not both 1. The $(CH_2)_m$ linker to the ester or carboxylic acid group, can be substituted with one or more substituents.

An antihistamine of the instant invention may be substituted by one or more substituents, which are selected and positioned within the molecule such that the compound is able to perform its intended function. For example, the substituent(s) can be located on any available position, such as, the aryl rings, the spacer molecule, the drug activity modulating moiety, any branching moieties, or on other substituents. Exemplary substituents include substituted or unsubstituted alkyl, alkenyl, alkynyl, and aromatic or aryl moieties as defined herein. In particular, the antihistamines of the invention may be substituted by substituents including, but not limited to, hydrogen; halogen, e.g. bromide, chloride, or fluoride; dimethylaminocarbonyl; fluoroalkyl, e.g., trifluoromethyl; hydroxy; alkyl, e.g., $C_{1-6}$ alkyl, e.g., methyl or ethyl; alkoxy, e.g., $C_{1-6}$ alkoxy, e.g., methoxy or propoxy; carboxylic acid; methylhydroxy; methylcarbonyl; cyano; aminomethyl; (aminoalkyl); ethoxycarbonylmethoxy; cyanomethyloxy; (acetoxyethyl)oxy; (hydroxyoxyethyl)oxy; morphilinoethyloxy; (tetrazol-5-yl)methyloxy; carboxymethyloxy; dimethylaminocarbonylmethyloxy; morphilinocarbonylmethyloxy; (1-ethoxycarbonyl-1-methylethyl)oxy; (1-carboxy-1methylethyl)oxy; (2-methoxyethyl)oxy; (1-dimethylaminocarbonyl-1-methylethyl)oxy; (1-ethoxycarbonyl) cyclobutoxy; (1-carboxy)cyclobutoxy; (1;1-dimethyl-2-hydroxyethyl)oxy; (2;2-dimethyl-2-hydroxyethyl)oxy; acyloxy; cycloalkyl; arylalkyl; alkoxycarbonyl; and substituted or unsubstituted amines.

In certain embodiments, the aryl rings may be substituted with one or more substituents, each of which may be different or the same, and include, for example, hydrogen, halogens, alkyl, fluoroalkyl, e.g., trifluoromethyl, hydroxy, alkoxy, and other substituents, such as, $-(O)_u-(CH_2)_t-C(O)OR_4$, $-(O)_u-(CH_2)_t-OC(O)R_4$, $-(O)_u-(CH_2)_t-C(O)-NR_5$ $R_6$ or $-(O)_u-(CH_2)_t-NHC(O)O-R_4$ wherein: t is an integer, such as an integer from zero to about three, and the methylene group $-(CH_2)_t-$ can be substituted or unsubstituted; and $R_4$, $R_5$ or $R_6$ are independently hydrogen, an aliphatic group, a substituted aliphatic group, an aromatic group, a substituted aromatic group or a non-aromatic heterocyclic group. Alternatively, $R_5$ and $R_6$, taken together with the nitrogen atom to which they are bonded, can form a non-aromatic heterocyclic ring.

Suitable substituents on an aliphatic group, aromatic group (carbocyclic and heteroaryl), non-aromatic heterocyclic ring or benzyl group include, for example, an electron withdrawing group, a halogen, azido, cyano, fluoroalkyl, e.g., trifluoromethyl, carboxylic acid, hydroxy, $-CONR_8$ $R_9$, $-NR_8$ $R_9$, $-OS(O)_2$ $NR_8$ $R_9$, $-S(O)_2$ $NR_8$ $R_8$ 9, sulfonic acid, sulfonamide, guanidino, $-(O)_u-(CH_2)_t-C(O)OR_4$, $-(O)_u-(CH_2)_t-OC(O)R_4$, $-(O)_u-(CH_2)_t-C(O)-NR_5$ $R_6$, $-(O)_u-(CH_2)_t-NHC(O)O-R_4$, $-Q-H$, $-Q$-(aliphatic group), $-Q$-(substituted aliphatic group), $-Q$-(aryl), $-Q$-(aromatic group), $-Q$-(substituted aromatic group), $-Q-(CH_2)_p$-(substituted or unsubstituted aromatic group), $-Q$-(non-aromatic heterocyclic group) or $-Q-(CH_2)_p$-(non-aromatic heterocyclic group) wherein: p is an integer from 1–5; $R_4$, $R_5$ or $R_6$ are independently $-H$, an aliphatic group, a substituted aliphatic group, an aromatic group, a substituted aromatic group, a non-aromatic heterocyclic group, $-NHC(O)-O$-(aliphatic group), $-NHC(O)-O$-(aromatic group) or $-NHC(O)-O$-(non-aromatic heterocyclic group); $R_5$ and $R_6$, taken together with the nitrogen atom to which they are bonded, can form a non-aromatic heterocyclic ring; t is an integer from zero to about three; the methylene group, —(CH$_2$)$_t$—, can be substituted or unsubstituted; and Q is —O—, —S—, —S(O)—, —S(O)$_2$—, —OS(O)$_2$—, —C(O)—, —OC(O)—, —C(O)O—, —C(O)C(O)—, —O—C(O)C(O)—, —C(O)NH—, —NHC(O)—, —OC(O)NH—, —NHC(O)O—, —NH—C(O)—NH—, —S(O)$_2$ NH—, —NHS(O)$_2$—, —N(R$_7$)—, —C(NR$_7$)NHNH—, —NHNHC(NR$_7$)—, —NR$_8$C(O)—or —NR$_8$ S(O)$_2$— wherein: R$_7$ is hydrogen, an aliphatic group, a benzyl group, an aryl group or non-aromatic heterocyclic group; R$_8$ and R$_9$ are independently hydrogen, hydroxy, an aliphatic group, a substituted aliphatic group, a benzyl group, an aryl group or non-aromatic heterocyclic group; and u is zero or one.

A substituted non-aromatic heterocyclic ring, benzyl group or aromatic group can also have an aliphatic or substituted aliphatic group, as a substituent. In addition, a substituted aliphatic group can also have an oxo group, epoxy group, non-aromatic heterocyclic ring, benzyl group, substituted benzyl group, aromatic group or substituted aromatic group as a substituent. A substituted non-aromatic heterocyclic ring can also have =O, =S, =NH or =N(aliphatic, aromatic or substituted aromatic group) as a substituent. A substituted aliphatic, substituted aromatic, substituted non-aromatic heterocyclic ring or substituted benzyl group can have more than one substituent. Acyl groups include substituted and unsubstituted aliphatic carbonyl, aromatic carbonyl, aliphatic sulfonyl and aromatic sulfonyl. Suitable electron withdrawing groups include, for example, alkylimines, alkylsulfonyl, carboxamido, carboxylic alkyl esters, —CH=NH, —CN, —NO$_2$ and halogens.

In certain embodiments of the invention, the therapeutic compound has a favorable biological property. In one embodiment of the invention, the invention is a method of treating a sleep disorder. The method comprises administering an effective amount of an antihistamine compound, such that the sleep disorder is treated, wherein the antihistamine compound has a favorable biological property (FBP).

The language "favorable biological property (FBP)" includes one or more biological properties that allow the compound to perform its intended function in an enhanced manner. Examples of favorable biological properties include but are not limited to induction of a discrete sleep or hypnotic state, activity of the therapeutic compound for a discrete period of time, penetration through the blood brain barrier into the CNS, e.g., resulting from lipophilicity of substituents or conformational lipophilicity (i.e., lipophilicity as a result of a particular conformation, such as internal salt formation between a carboxylate anion and a protonated amine), modulation of the half-life of the therapeutic compound, in vivo hydrolysis of an ester by esterases that allows sequestration of the therapeutic compound in the CNS, an alteration of charge, an alteration of pharmacology-kinetics, an alteration of log P by a value of 1 or more, increased receptor selectivity, reduced peripheral half-life, the ability to increase dosage, increased peripheral elimination, decreased anti-muscarinic activity, decreased anti-cholinergic, and any combination thereof. It should be understood that the language "FPB" is intended to include a single property or a combination of two or more properties. In particular embodiments of the invention, the therapeutic compound induces a discrete sleep or hypnotic state by penetration into the CNS. In certain embodiments of the invention, the FBP includes increased concentration within the CNS for a discrete period of time as a result of a slower rate of conversion to the corresponding carboxylic acid by in vivo esterase activity within the CNS as compared with the periphery. In another embodiment of the invention, the FBP includes increased concentration within the CNS for a discrete period of time as a result of the existence of an ionic bond that includes the carboxylate ion of the corresponding carboxylic acid, e.g., zwitterion species formation with a nitrogen atom within the compound or salt bridge formation.

In certain embodiments, wherein the therapeutic compound is active for a discrete period of time, the FBP is a reduced ability of the subject to form a tolerance to the therapeutic compound. The language "tolerance" includes the natural tendency of a subject to become less affected by continued administration of a particular therapeutic compound due to repeated exposure to the compound. It should be noted that tolerance is typically increased coincident with the increased time that a compound is present in its active state within the subject. Reduced tolerance would coincide with increased therapeutic effectiveness.

The language "discrete sleep or hypnotic state" include a state of consciousness that is induced by the presence of active therapeutic compound of the invention, for a defined period of time. This is in contrast to the lingering hangover effect resulting from the existing treatments, e.g., antihistamines, used for their sedative effect that maintain active drug concentrations for extended periods of time in the periphery.

The language "discrete period of time" includes a defined period of time in which the therapeutic compound is active, and depends upon the physical and reactive properties of the ester group. In one embodiment of the invention, the half-life of the therapeutic compound is 1 to 8 hours. In a preferred embodiment, the half-life of the therapeutic compound is 6 hours.

The language "sequestration" includes having enhanced concentration in the CNS and more rapid elimination from the periphery. The product of hydrolysis can exit the brain by various carboxylate excretion mechanisms, possibly at a slower rate than from the periphery producing a CNS sequestration of the carboxylate for a defined, or discrete, period of time. In one embodiment of the invention, elimination of the hydrolyzed carboxylate-containing metabolite occurs predominately by excretion though the kidneys, due to enhanced polarity of the metabolite, either as the free carboxylate or after Phase II further metabolism. In another embodiment, elimination occurs predominately by metabolism in the liver, e.g. hydrolysis of the ester followed by glucuronidation, and excretion into the bile. In certain embodiments, the brain assists in the elimination.

Another embodiment of the current invention is a method of modulating a sleep disorder target comprising administering to a subject an effective amount of a therapeutic compound, such that the therapeutic compound penetrates into the CNS and modulates the sleep disorder target, wherein the therapeutic compound is as described above and comprises any one of the following formulae:

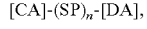

[CA]-(SP)$_n$-[DA],

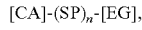

[CA]-(SP)$_n$-[EG],

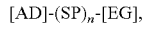

[AD]-(SP)$_n$-[EG],

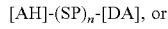

[AH]-(SP)$_n$-[DA], or

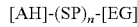

[AH]-(SP)$_n$-[EG]

wherein CA is a moiety that modulates an active CNS target receptor or a collection of active CNS target receptors, AD is a moiety that agonizes an adenosine receptor or a collection of adenosine receptors, AH is a moiety that antagonizes a histamine receptor or a collection of histamine receptors, DA is a drug activity modulating moiety that provides the ability to modulate the activity of the therapeutic compound, EG is an ester group that modifies the half-life of the therapeutic compound, SP is a spacer molecule, and n is 0 or 1.

In an additional embodiment, the invention is a CNS disorder target modulator comprising the formula:

[CA]-(SP)$_n$-[DA], or

[CA]-(SP)$_n$-[EG]

wherein CA is a moiety that modulates an active CNS target receptor or a collection of active CNS target receptors, DA is a drug activity modulating moiety that provides the ability to modulate the activity of the therapeutic compound, EG is an ester group that modifies the half-life of the therapeutic compound, SP is a spacer molecule, and n is 0 or 1.

Another embodiment of the invention is a sleep disorder target modulator comprising the formula:

[CA]-(SP)$_n$-[EG]

wherein CA is a moiety that modulates an active CNS target receptor or a collection of active CNS target receptors, EG is an ester group that modifies the half-life of the therapeutic compound, SP is a spacer molecule, and n is 0 or 1.

In a particular embodiment of the invention, a sleep disorder target modulator comprises the formula:

[AH]-(SP)$_n$-[DA] or

[AH]-(SP)$_n$-[EG]

wherein AH is a moiety that antagonizes a histamine receptor or a collection of histamine receptors, DA is a drug activity modulating moiety that provides the ability to modulate the activity of the therapeutic compound, EG is an ester group that modifies the half-life of the therapeutic compound, SP is a spacer molecule, and n is 0 or 1.

In accord with the invention, particular embodiments of the pheniramine-like therapeutic compound used for treating CNS disorders, e.g., sleep disorders, are:

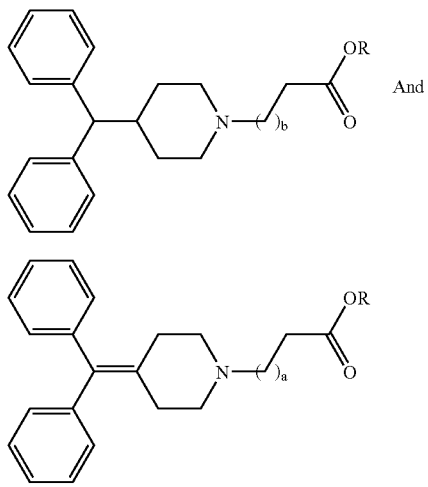

(I)

And (II)

wherein a=0 through 5, b=0 through 5, and R is H or any group which imparts properties to the therapeutic compound to promote penetration into the CNS and to modify the half-life of the compound. In another embodiment of the therapeutic compound used for the treatment of a disorder, the diphenhydramine-like therapeutic compound is:

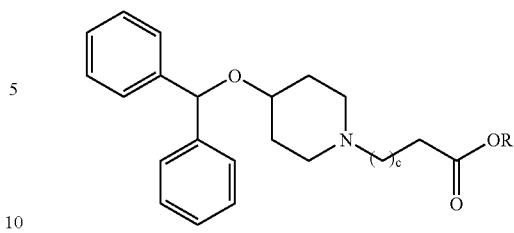

(III)

c=0 through 5, and R is H or any group which imparts properties to the therapeutic compound to promote penetration into the CNS and to modify the half-life of the compound.

In another embodiment of the therapeutic compound used for the treatment of a disorder, the triprolidine-like therapeutic compound is:

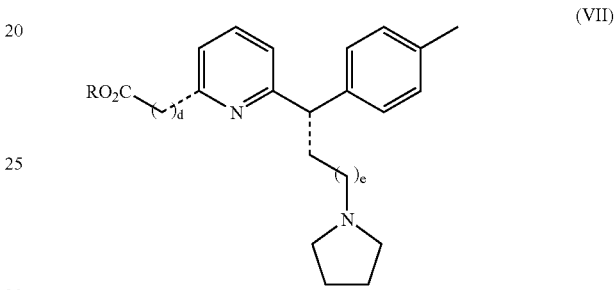

(VII)

wherein d=0 through 5, e=0 through 4, the dashed line represents a single or double bond, and R is H or any group which imparts properties to the therapeutic compound to promote penetration into the CNS and to modify the half-life of the compound.

In another embodiment of the therapeutic compound used for the treatment of a disorder, the pheniramine analog therapeutic compound is:

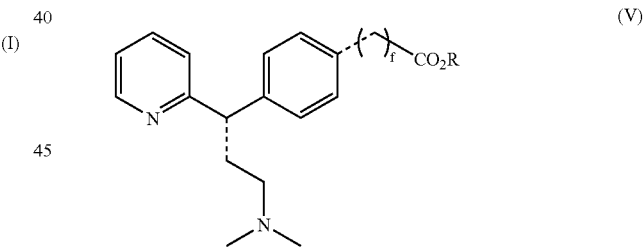

(V)

wherein f=0 through 5, the dashed line represents a single or double bond, and R is H or any group which imparts properties to the therapeutic compound to promote penetration into the CNS and to modify the half-life of the compound.

In preferred embodiments of the invention, a=0 or 1; b=0 or 1; c=0 or 1; d=1 or 2; e=1 or 2; and f=1 or 2. In particular embodiments of Formulae (I), (II), (III), (VII), and (VIII), R is a bulky ester.

In one embodiment, the compound of the invention is doxepin, pheniramine, diphenhydramine, triprolidine, or acrivastine.

An additional embodiment of the invention is the composition of several analogs of doxepin and acrivastine. The structures of several compounds, as well as their activity, are shown in Scheme 1. These compounds have demonstrated anti-H1 activity related to other antihistamine compounds of the invention.

SCHEME 1

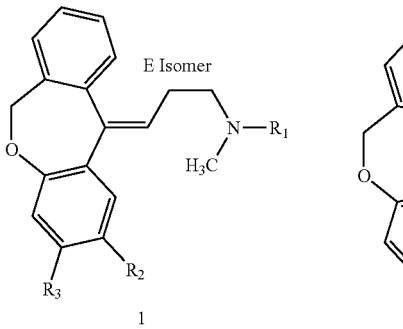

1

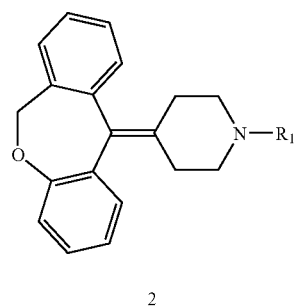

2

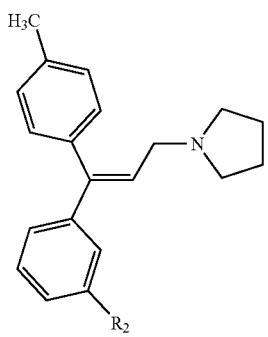

3

| Doxepine Analogs[1,2,3] | |
|---|---|
| (R = H unless shown otherwisw) | |
| Compd. | pK$_B$ |
| 1, R$_1$ = CH$_3$ | 10.11 |
| 1, R$_1$ = CH$_2$CO$_2$H | 7.81 |
| 1, R$_1$ = CH$_2$CH$_2$CO$_2$H | 8.51 |
| | K$_i$(nM) |
| 1, R$_2$ = CH$_2$ | 0.13 |
| 1, R$_2$ = CH$_2$CH$_2$OH | 0.48 |
| 1, R$_2$ = CO$_2$H | 4.2 |
| 1, R$_2$ = CH$_2$CO$_2$H | 5.2 |
| 1, R$_2$ = CH$_2$CH$_2$CO$_2$H | 4.2 |
| 1, R$_2$ = CO$_2$H (Z isomer) | 20.0 |
| 1, R$_3$ = CO$_2$H (Z isomer) | 24.0 |
| | pIC$_{50}$ |
| 2, R$_1$ = CH$_3$ | 9.5 |
| 2, R$_2$ = CH$_2$CH$_2$CO$_2$H | 6.5 |

| Acrivastine Analogs | |
|---|---|
| Compd. | pA$_2$ |
| 3, R$_2$ = H | 9.7 |
| 3, R$_2$ = CH=CHCO$_2$H | 9.2 |

References: 1) H. Muramatsu et al, Chem. Pharm. Bull. 41(11), 1987 (1993),
2) N. Iwasaki et al, Chem. Pharm. Bull. 42(11), 2285 (1994),
3) E. Ohshima, et al., J. Med. Chem. 35, 2074 (1992).

In particular embodiments of the invention, the doxepin-like therapeutic compound is represented by the following formula:

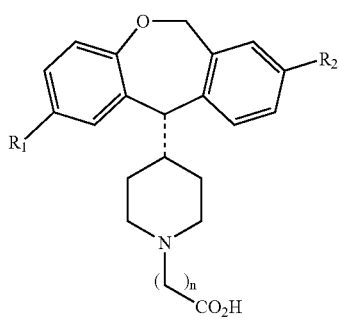

wherein
the dashed line represents a single or double bond;
R$_1$=H, OH, CH$_2$OH, CH$_2$CH$_2$OH;
R$_2$=H, CH$_3$, CF$_3$, Cl, Br; and
n is 1,2, or 3.

In certain embodiments, the R$_1$ substituents will alter the in vivo half-life of the drug. In certain embodiments, the R$_2$ substituents enhance the H1 receptor binding affinity. In addition, the spacer molecule, e.g., the (CH$_2$)$_m$ linker to the carboxylic acid group, can be substituted with one or more substituents. In one embodiment, the spacer molecule is mono-substituted. In another embodiment of the invention, the spacer molecule is disubstituted. In particular embodiments, the linkers of the invention may be geminally-dialkylated, e.g., gem-dimethylated, singly substituted with a substituent other than a noncyclic alkyl group, e.g., a heteroatom, or a cyclic substituent wherein one or more of the carbons of the spacer molecule is contained in the ring, e.g., heterocycle (e.g., tetrahydrofuran or tetrahydropyran), or cyclic alkyl, e.g., cyclopropyl. However, the substitution of the spacer molecule is independent of the substitution at the R$_1$ and R$_2$ positions.

In specific embodiments of the invention which are directed to doxepin-like compounds, such that when R$_1$ and R$_2$ are both H, the alkyl spacer molecule to the carboxylic acid is singly or doubly substituted with alkyl., including gem-dialkyl substitution, e.g., gem-dimethyl substitution. In certain embodiments, the compound of the invention is not a doxepin-like compound of Formula (V), wherein the alkylene spacer molecule is unsubstituted, and R$_1$ and R$_2$ are selected from the group consisting of H, halogen CF$_3$, OH, C$_{1-6}$ alkyl, C$_{1-6}$ alkoxy. In another embodiment, R$_1$ and R$_2$ are not both H when the alkylene spacer molecule is unsubstituted. In one embodiment, n is not 2 or 3 when the spacer molecule is unsubstituted.

Another embodiment of the invention is a pharmaceutical composition comprising a therapeutic compound as prepared according to the methodology of this invention, and a pharmaceutically acceptable carrier.

In specific embodiments of the invention, the therapeutic compounds of the invention for treating CNS disorders, e.g., sleep disorders, are selected from Table 2. In certain embodiments, the therapeutic compounds of the invention for treating CNS disorders, e.g., sleep disorders, are selected from Table 3.

TABLE 2

| Structure | Series # |
|---|---|
| (diphenylmethoxy-piperidine with N-CH2CH2CO2H, HCl) | 6a-HCl |
| (diphenylmethoxy-piperidine with N-CH2CH2CO2Et, C2H2O4) | 6c-oxalate |
| (diphenylmethoxy-piperidine with N-CH2CH2CO2iPr, C2H2O4) | 6d-oxalate |
| (diphenylmethoxy-piperidine with N-CH2CH2CO2iBu, C2H2O4) | 6e-oxalate |

TABLE 2-continued

| Structure | Series # |
|---|---|
| (diphenylmethoxy-piperidine with N-CH2CH2-CO2CycFe, C2H2O4) | 6f-oxalate |
| (4-(diphenylmethylene)piperidine with N-CH2-CO2H, HOAc) | 15a-HOAc |
| (4-(diphenylmethylene)piperidine with N-CH2-CO2Et, HCl) | 15c-HCl |
| (4-(diphenylmethylene)piperidine with N-CH2-CO2iPr, C2H2O4) | 15d-oxalate |
| (4-(diphenylmethylene)piperidine with N-CH2-CO2iBu, C2H2O4) | 15e-oxalate |
| (4-(diphenylmethylene)piperidine with N-CH2-CO2CycFe, C2H2O4) | 15f-oxalate |

TABLE 2-continued

| Structure | Series # |
|---|---|
| (diphenylmethylene-piperidine-N-CH2CH2-CO2H · HCl) | 11a-HCl |
| (diphenylmethylene-piperidine-N-CH2CH2-CO2Et · HCl) | 11c-HCl |
| (diphenylmethylene-piperidine-N-CH2CH2-CO2iPr · C2H2O4) | 11d-oxalate |
| (diphenylmethylene-piperidine-N-CH2CH2-CO2iBu · HCl) | 11e-HCl |
| (diphenylmethylene-piperidine-N-CH2CH2-CO2CycFe · C2H2O4) | 11f-oxalate |
| (diphenylmethylene-piperidine-N-CH2-CO2H · HCl) | 16a-HCl |

TABLE 2-continued

| Structure | Series # |
| --- | --- |
| [diphenylmethylene-piperidine-N-CH2CO2Et] | 16c-oxalate (C2H2O4) |
| [diphenylmethylene-piperidine-N-CH2CO2iPr] | 16d-oxalate (C2H2O4) |
| [diphenylmethylene-piperidine-N-CH2CO2iBu] | 16e-oxalate (C2H2O4) |
| [diphenylmethylene-piperidine-N-CH2CO2CycFe] | 16f-oxalate (C2H2O4) |
| [diphenylmethylene-piperidine-N-CH2CH2CO2H · HCl] | 13a-HCl |
| [diphenylmethylene-piperidine-N-CH2CH2CO2Et] | 13c-oxalate (C2H2O4) |

TABLE 2-continued
| Structure | Series # |
|---|---|
| 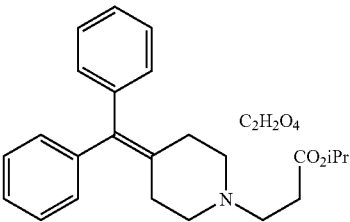 | 13d-oxalate |
| 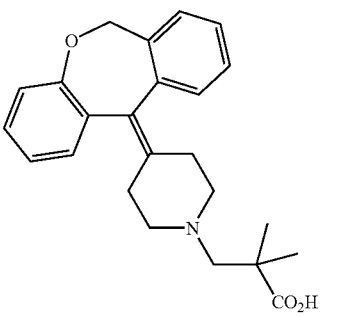 | 74a |
| 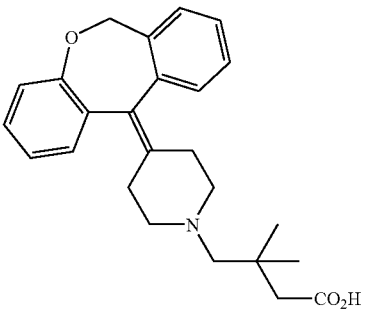 | N/A |
| 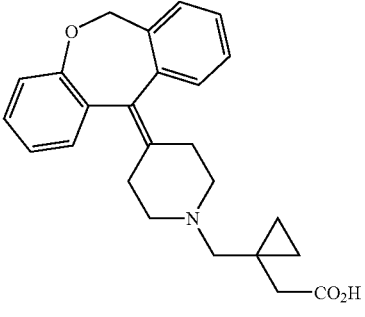 | N/A |
| 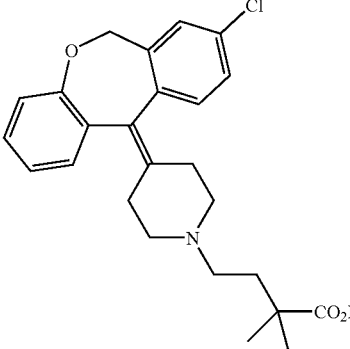 | D015a |

TABLE 2-continued

| Structure | Series # |
|---|---|
| (structure) | D034a |
| (structure) | 204a |
| (structure) | D102a |
| (structure) | N/A |

TABLE 2-continued

| Structure | Series # |
|---|---|
| [structure] | N/A |
| [structure] | dox7a |
| [structure] | 6i-oxalate |
| [structure] | 5e-oxalate |

TABLE 2-continued
| Structure | Series # |
|---|---|
| 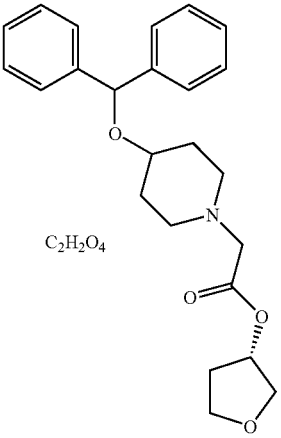 | 5h-oxalate |
| 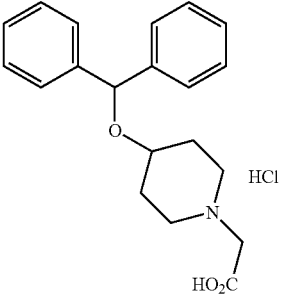 | 5a-HCl |
| 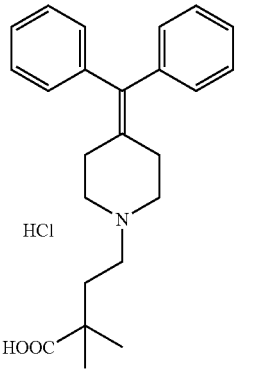 | 115a-HCl |
| 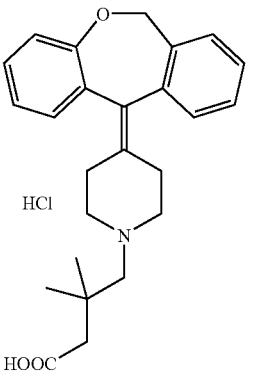 | D006a-HCl |

TABLE 2-continued
| Structure | Series # |
|---|---|
| 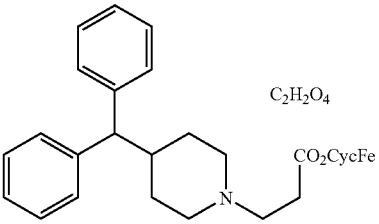 | 13-f-oxalate |
| 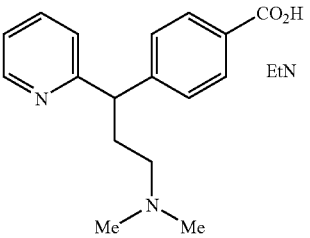 | 18a-Et3N |
| 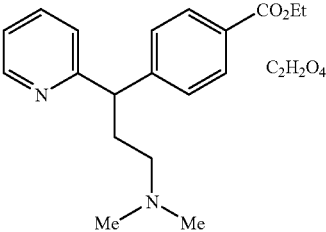 | 18c-oxalate |
| 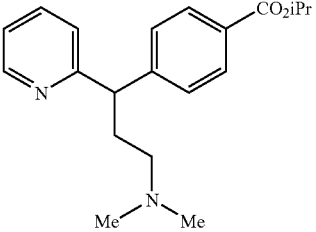 | 18d |
| 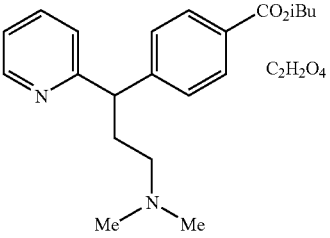 | 18e-oxalate |
| 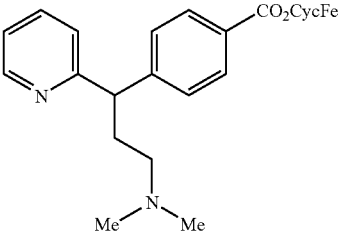 | 18f |

TABLE 2-continued

| Structure | Series # |
|---|---|
| 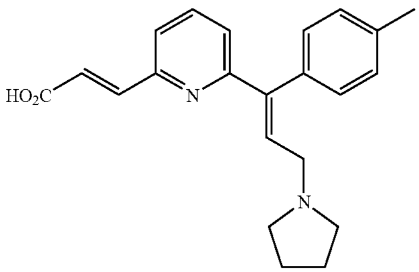 | E,E-7a |
| 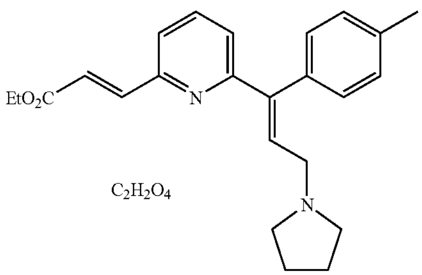 | E,E-7c-oxalate |
| 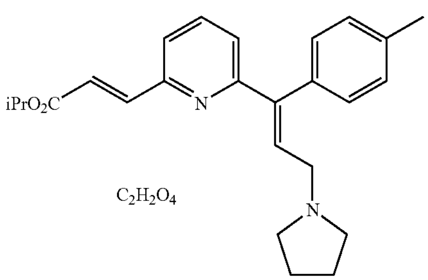 | E,E-7d-oxalate |
| 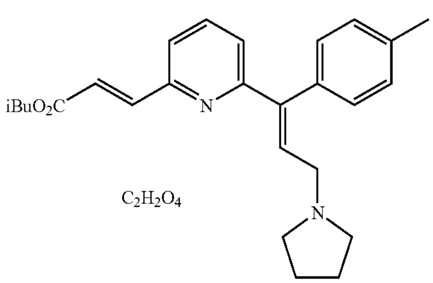 | E,E-7e-oxalate |
| 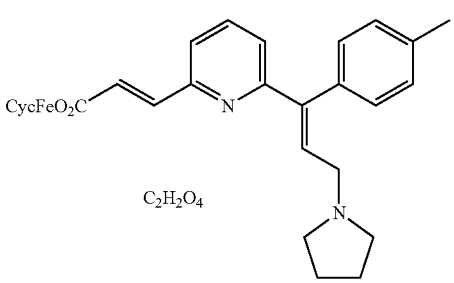 | E,E-7f-oxalate |

TABLE 2-continued

| Structure | Series # |
|---|---|
| 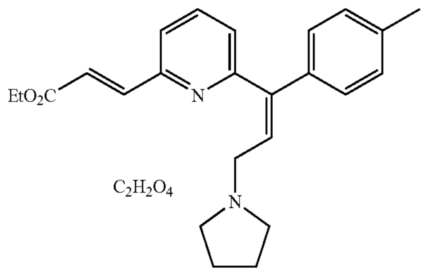 | E,Z-7c-oxalate |
| 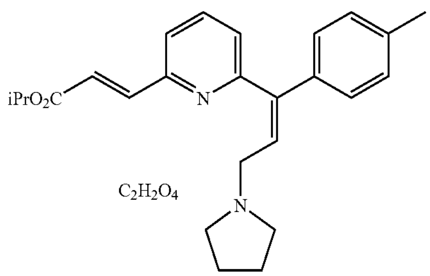 | E,Z-7e-oxalate |
| 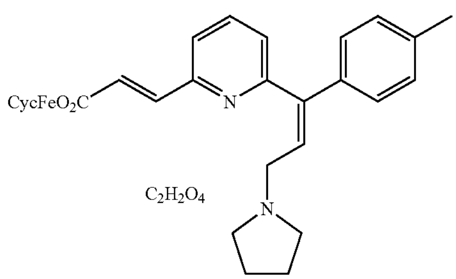 | E,Z-7f-oxalate |
| 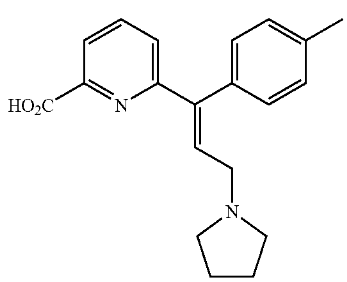 | E-16a |
| 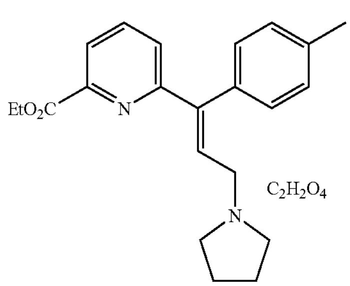 | E-16c-oxalate |

TABLE 2-continued

| Structure | Series # |
|---|---|
| (iPrO2C-pyridine-C(p-tolyl)=CH-CH2-N(pyrrolidine)) · C2H2O4 | E-16d-oxalate |
| (iBuO2C-pyridine-C(p-tolyl)=CH-CH2-N(pyrrolidine)) · C2H2O4 | E-16e-oxalate |
| (CycFeO2C-pyridine-C(p-tolyl)=CH-CH2-N(pyrrolidine)) · C2H2O4 | E-16f-oxalate |
| (dibenzoxepine=piperidine-N-CH2-CO2Et) · C2H2O4 | dox7c-oxalate |
| (dibenzoxepine=piperidine-N-CH2-CO2iPr) · C2H2O4 | dox7d-oxalate |

TABLE 2-continued

| Structure | Series # |
|---|---|
| [structure: dibenzoxepine-piperidinylidene with N-CH2-CO2iBu, C2H2O4] | dox7e-oxalate |
| [structure: dibenzoxepine-piperidinylidene with N-CH2-CO2CycFe, C2H2O4] | dox7f-oxalate |
| [structure: dibenzoxepine-piperidinylidene with N-(CH2)3-C(CH3)2-CO2H] | 75a |
| [structure: pyrido-benzoxepine-piperidinylidene with N-cyclopropyl-CH2-CO2H] | N/A |

TABLE 2-continued

| Structure | Series # |
|---|---|
| (dibenzoxepine-piperidinylidene with ethyl-cyclopropanecarboxylic acid) | N/A |
| (7-CF₃ dibenzoxepine-piperidinylidene with 3,3-dimethyl-propanoic acid chain) | D035a |
| (7-CH₃ dibenzoxepine-piperidinylidene with 2,2-dimethyl-acetic acid chain) | D024a |
| (pyrido-benzoxepine-piperidinylidene with hydroxyethyl and propanoic acid substituents) | 202a |

TABLE 2-continued
| Structure | Series # |
|---|---|
| 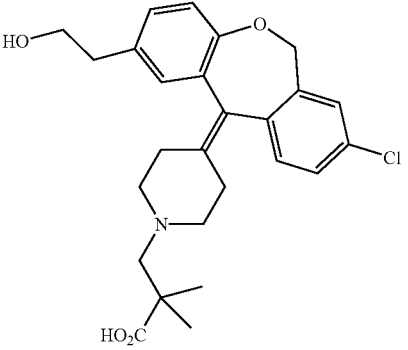 | D214a |
| 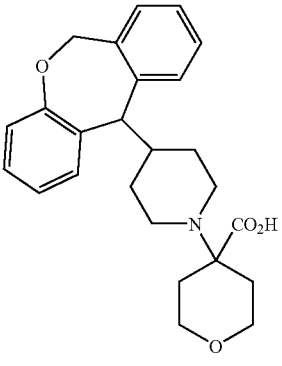 | N/A |
| 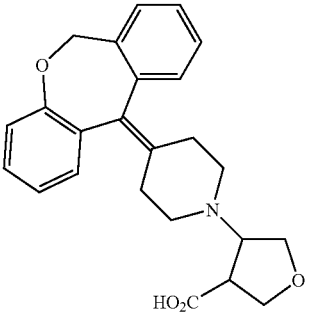 | N/A |
| 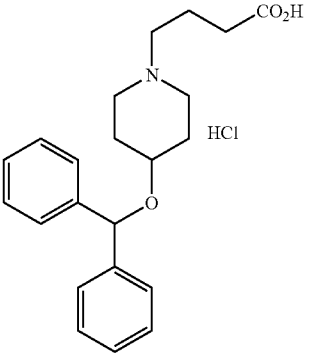 | 53a |

TABLE 2-continued

| Structure | Series # |
|---|---|
| 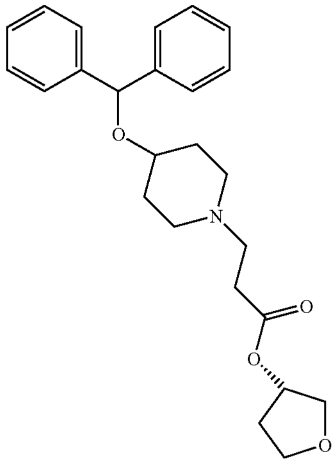 | 6h-oxalate |
| 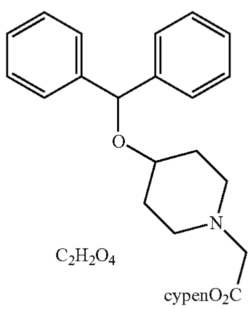 | 5f-oxalate |
| 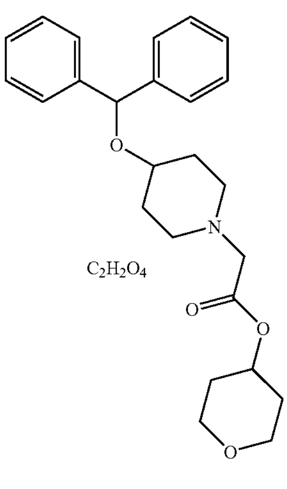 | 5i-oxalate |

TABLE 2-continued

| Structure | Series # |
|---|---|
| 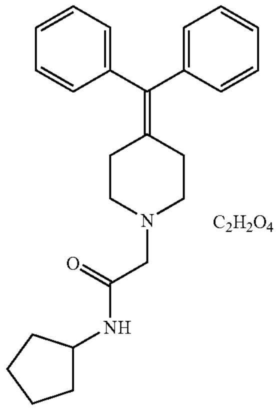 | 15k-oxalate |
| 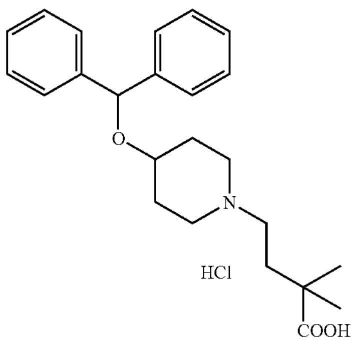 | 55a-HCl |
| 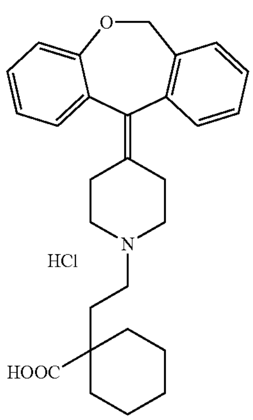 | D007a-HCl |
| 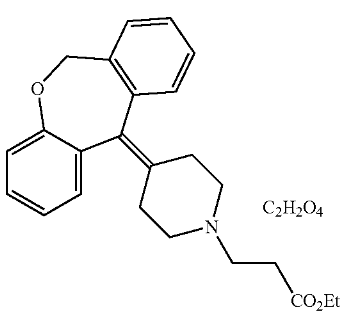 | 8c-oxalate |

TABLE 2-continued

| Structure | Series # |
|---|---|
| 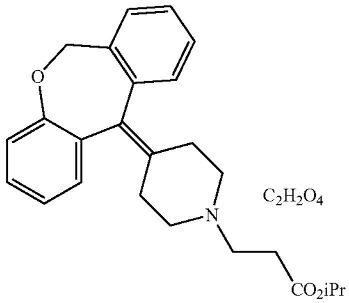 | 8d-oxalate |
| 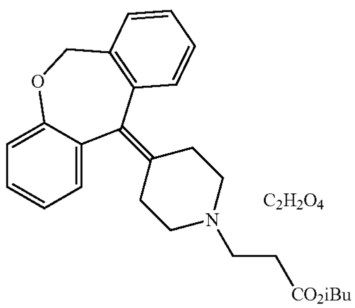 | 8e-oxalate |
| 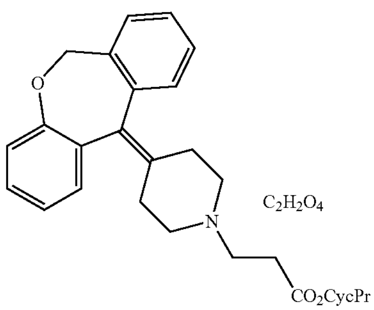 | 8f-oxalate |
| 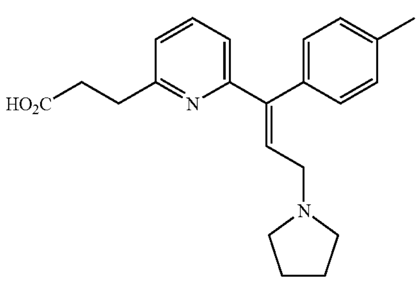 | E,E-10a |
| 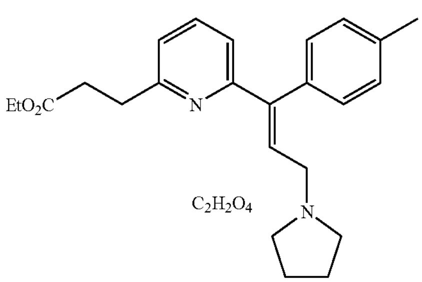 | E,E-10c-oxalate |

TABLE 2-continued
| Structure | Series # |
|---|---|
| 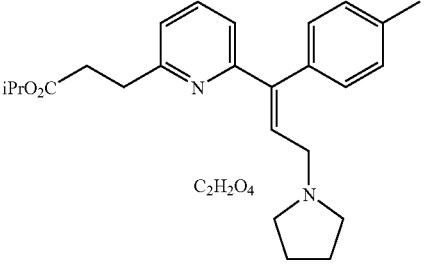 | E,E-10d-oxalate |
| 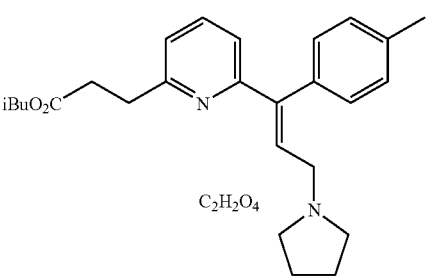 | E,E-10e-oxalate |
| 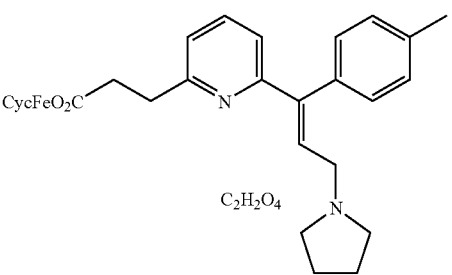 | E,E-10f-oxalate |
| 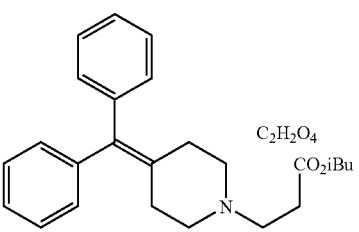 | 11e-oxalate |
| 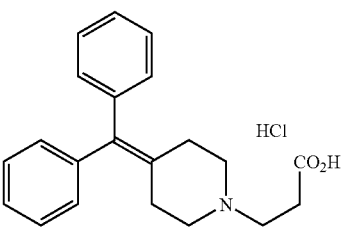 | 15a-HCl |

TABLE 2-continued
| Structure | Series # |
|---|---|
| 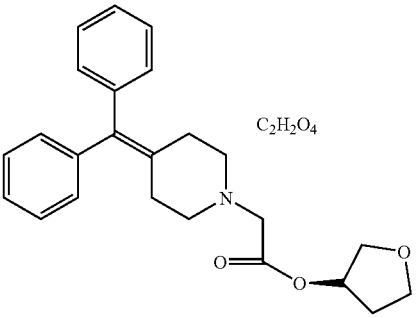 | 15g-oxalate |
| 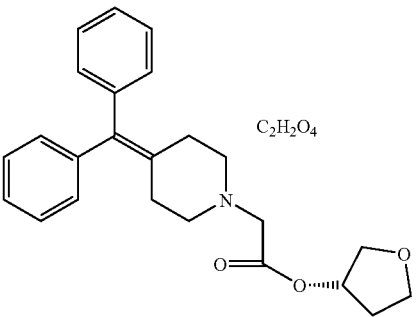 | 15h-oxalate |
| 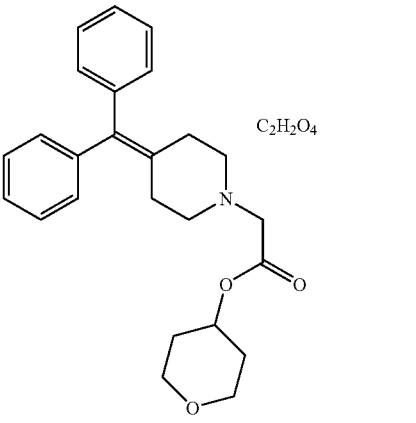 | 15i-oxalate |
| 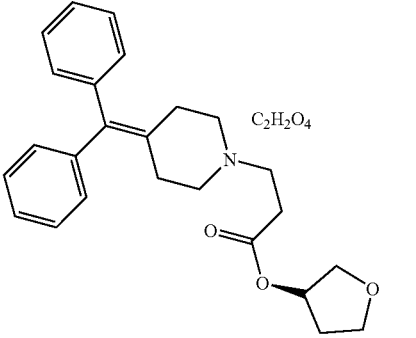 | 11g-oxalate |

TABLE 2-continued

| Structure | Series # |
|---|---|
| 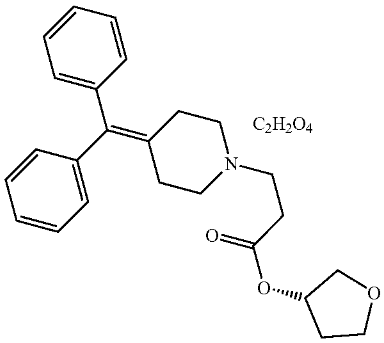 | 11h-oxalate |
| 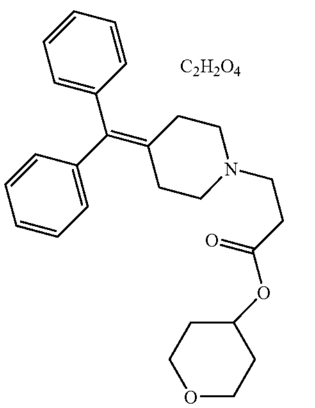 | 11i-oxalate |
| 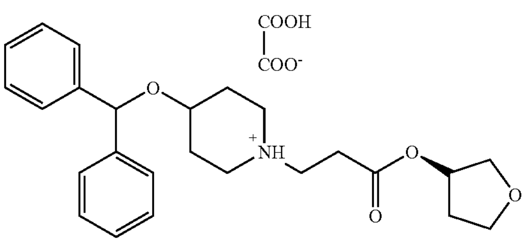 | 6g-oxalate |
| 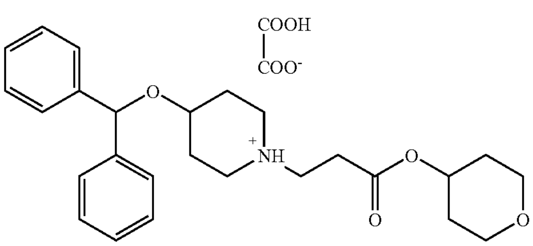 | 6i-oxalate |
| 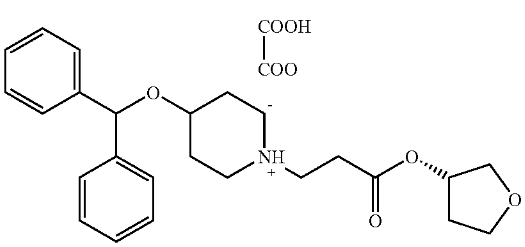 | 6h-oxalate |

TABLE 2-continued
| Structure | Series # |
|---|---|
| 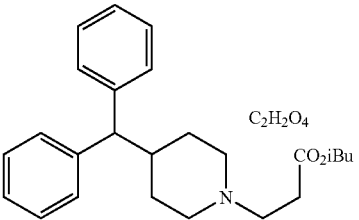 | 13e-oxalate |
| 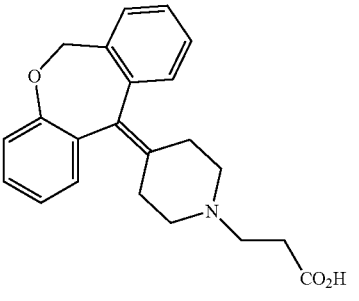 | 8a |
| 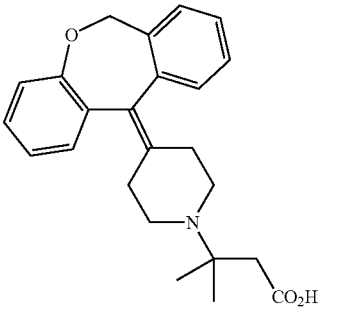 | N/A |
| 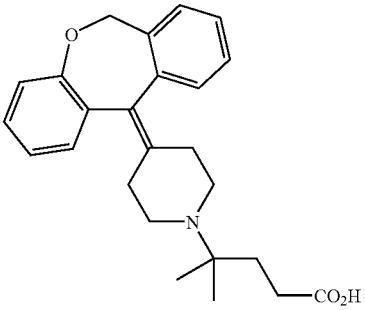 | N/A |
| 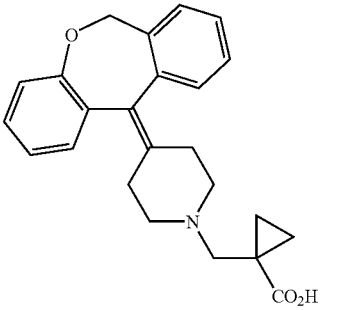 | D003a-HCl |

TABLE 2-continued

| Structure | Series # |
|---|---|
| (structure) | N/A |
| (structure) | D014a |
| (structure) | D025a |
| (structure) | D104a |

TABLE 2-continued

| Structure | Series # |
|---|---|
| | N/A |
| | N/A |
| 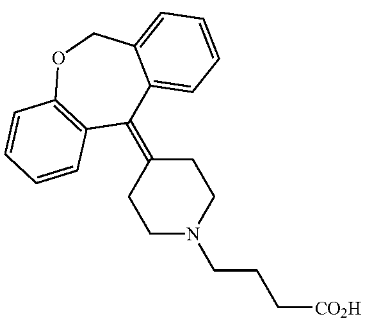 | 73a |
| 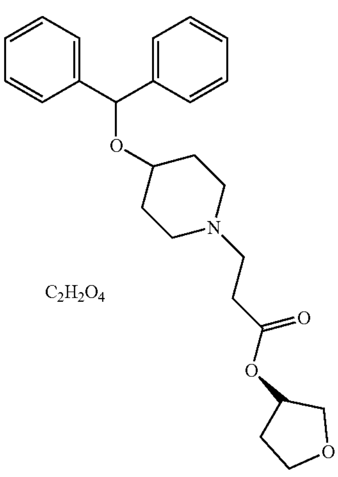 | 6g-oxalate |

TABLE 2-continued

| Structure | Series # |
|---|---|
| 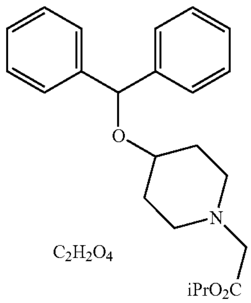 | 5d-oxalate |
| 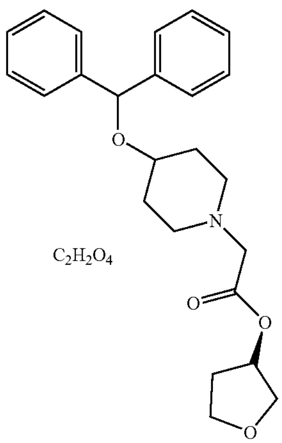 | 5g-oxalate |
| 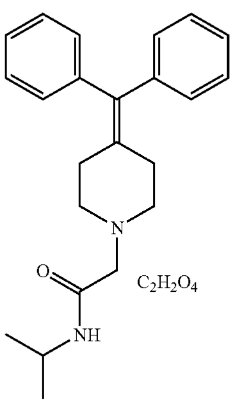 | 15j-oxalate |
| 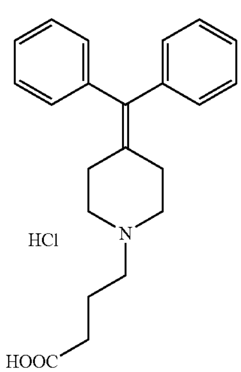 | 113a-HCl |

TABLE 2-continued
| Structure | Series # |
|---|---|
| 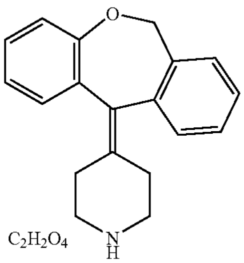 | N/A |
TABLE 3
| Structure | Series # |
|---|---|
| (diphenylmethoxy piperidine with N-CH2CH2CO2H, HCl) | 6a-HCl |
| (diphenylmethoxy piperidine with N-CH2CH2CO2Et, C2H2O4) | 6c-oxalate |
| (diphenylmethoxy piperidine with N-CH2CH2CO2iPr, C2H2O4) | 6d-oxalate |

TABLE 3-continued

| Structure | Series # |
|---|---|
| (diphenylmethoxy-piperidine with N-CH2CH2-CO2iBu; C2H2O4) | 6e-oxalate |
| (diphenylmethoxy-piperidine with N-CH2CH2-CO2CycPe; C2H2O4) | 6f-oxalate |
| (diphenylmethylene-piperidine with N-CH2-CO2H; HOAc) | 15a-HOAc |
| (diphenylmethylene-piperidine with N-CH2-CO2Et; HCl) | 15c-HCl |
| (diphenylmethylene-piperidine with N-CH2-CO2iPr; C2H2O4) | 15d-oxalate |

TABLE 3-continued

| Structure | Series # |
|---|---|
| (diphenylmethylene-piperidine with N-CH2-CO2iBu), C2H2O4 | 15e-oxalate |
| (diphenylmethylene-piperidine with N-CH2CH2-CO2iBu), C2H2O4 | 11e-oxalate |
| (diphenylmethylene-piperidine with N-CH2CH2-CO2H), HCl | 15a-HCl |
| (diphenylmethylene-piperidine with N-CH2-C(=O)-O-(S)-tetrahydrofuran-3-yl), C2H2O4 | 15g-oxalate |
| (diphenylmethylene-piperidine with N-CH2-C(=O)-O-(R)-tetrahydrofuran-3-yl), C2H2O4 | 15h-oxalate |

TABLE 3-continued

| Structure | Series # |
|---|---|
| 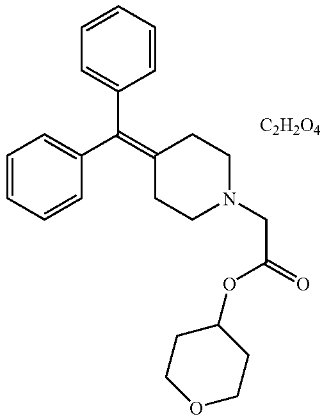 | 15i-oxalate |
| 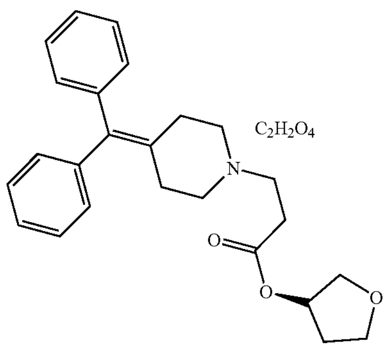 | 11g-oxalate |
| 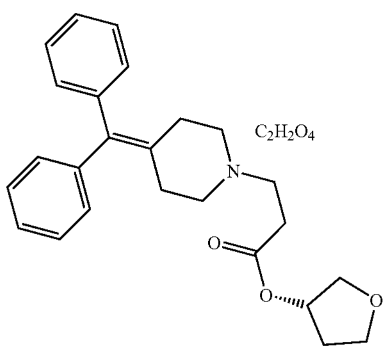 | 11h-oxalate |
| 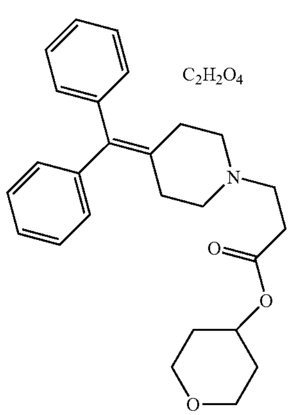 | 11i-oxalate |

TABLE 3-continued

| Structure | Series # |
|---|---|
| (diphenylmethoxy-piperidinium with N-CH2CH2C(O)O-(S)-tetrahydrofuran-3-yl, oxalate counterion) | 6g-oxalate |
| (4-(diphenylmethylene)piperidine, N-CH2CH2CO2Et, HCl) | 11c-HCl |
| (4-(diphenylmethylene)piperidine, N-CH2CH2CO2iPr, C2H2O4) | 11d-oxalate |
| (4-(diphenylmethylene)piperidine, N-CH2CH2CO2iBu, HCl) | 11e-HCl |
| (4-(diphenylmethylene)piperidine, N-CH2CH2CO2CycFe, C2H2O4) | 11f-oxalate |
| (4-(diphenylmethylene)piperidine, N-CH2CH2CO2H, HCl) | 11a-HCl |

TABLE 3-continued

| Structure | Series # |
|---|---|
| [structure: diphenylmethyl-O-piperidine-NH+-CH2CH2-C(=O)-O-(tetrahydrofuran-3-yl); oxalate counterion COOH/COO-] | 6h-oxalate |
| [structure: diphenylmethylene-piperidine-N-CH2-CO2CycPe; C2H2O4] | 15f-oxalate |
| [structure: diphenylmethyl-O-piperidine-NH+-CH2CH2-C(=O)-O-(tetrahydropyran-4-yl); oxalate counterion COOH/COO-] | 6i-oxalate |

In another embodiment, the invention is intended to include any novel compounds, including compounds prepared as intermediates, described herein. The scope of the present invention is also intended to include the existence of stereocenters within the compounds of the invention, including compounds in both their racemic and stereoisomer enriched forms. Additionally, the compounds described above are intended to include analogs containing art-recognized substituents that do not significantly effect the analog's ability to perform its intended function. Furthermore, any novel synthesis of the compounds of the invention described herein, is also intended to be included within the scope of the present invention.

Assays can be used to design and/or select compounds useful within the present invention. The SCORE method, described in Example 9, would be an example of such an assay. Multiple assay components, such as total sleep time, cumulative nonREM sleep profile, maximum nonREM sleep bout length, average nonREM sleep bout length, nonREM sleep time, nonREM onset of action profile, sleep latency, REM sleep time, REM sleep bout length, cumulative REM sleep profile, maximum wake bout length, average wake bout length, locomotor activity, locomotor activity intensity, body temperature, and drinking are used to define compounds that would be useful in the present invention. For example, in determining therapeutic compounds that would be useful as sedatives or wake-promoting compounds, all of the components listed above would be used in determining a preferred therapeutic compound. Antidepressant therapeutic compounds would use the components of total sleep time, cumulative nonREM sleep profile, maximum nonREM sleep bout length, REM sleep time, REM sleep bout length, locomotor activity, locomotor activity intensity, and body temperature for determination of preferred therapeutic compounds.

Exemplification of the Invention

The invention is further illustrated by the following examples that should not be construed as limiting.

Synthetic Preparation

Several synthetic protocols for compounds of the invention and intermediates thereto are shown below and are further depicted in the appropriate schemes. The compounds shall be herein referred to as Series in direct reference to the associated compound labeling number.

EXAMPLE 1

Synthesis of Antihistamine Intermediates

Several synthetic protocols for compounds of the invention are shown below and are further depicted in Scheme 2.

4-[diphenyl(hydroxy)methyl]-1-methylpiperidine (9). A solution of benzophenone (60 g, 0.33 mol) in anhydrous THF (200 mL) was added dropwise over a period of 20 min to a Grignard reagent that was prepared from 59 g (0.44 mol) of freshly distilled 4-chloro-1-methylpiperidine, Mg (1.3 mol) in THF (1L). After stirring overnight, the reaction mixture was quenched ($H_2O$, then dilute HCl) and extracted (2×500 mL) with ethyl acetate. The combined organics were dried with $Na_2SO_4$, filtered, and evaporated to dryness to give 89.5 g of alcohol 9. This alcohol was used without further purification. The structure was confirmed by $^1H$ NMR.

4-(Diphenylmethylidene)-1-methylpiperidine (10). Alcohol 9 (27.3 g, 97 mmol) was suspended in concentrated HCl (360 mL) and heated at reflux (oil bath temperature above 96° C.) for 2 h. The mixture was cooled in an ice bath followed by the addition of ethyl acetate (300 mL). A solution of sodium hydroxide (200 g) in water (400 mL), cooled to 10° C., was added dropwise to the acidic mixture until the pH was 14. Ethyl acetate (200 mL) was then added and the organic layer was separated and washed with brine (200 mL). The combined aqueous layers were extracted with ethyl acetate (2×300 mL). The combined organic layers were dried, filtered, and concentrated to give 23 g of the product as a brown oil. $^1$H NMR confirmed the structure of the product.

4-(Diphenylmethyl)-1-methylpiperidine (12). Solid sodium borohydride (6 g, 160 mmol) and solid alcohol 9 (4.5 g, 16 mmol) were mixed to a fairly homogeneous solid mixture using a spatula. With rapid $N_2$ flow through the system, the solid mixture was added intermittently (cautiously and in small portions over a period of 45 min) to stirred trifluoroacetic acid (200 mL) cooled to 0° C. Extra caution was taken during the addition of the $NaBH_4$ mixture to prevent localized heating and rapid build-up of pressure from the evolving and highly flammable $H_2$. After the addition was complete, the reaction mixture was evaporated to dryness. The above procedure was repeated using 5.2 g of 9 and proportional amounts of the other reagents. The combined residues from the two experiments were diluted with $EtOAc/CH_2Cl_2$ followed by the addition of aqueous NaOH and then solid NaOH until the aqueous layer maintained a pH of 11. The organic layer was dried with $Na_2SO_4$, filtered, and evaporated to an oil that solidified. Chromatography over silica gel using 10% MeOH/10% $Et_3N$ in EtOAc gave 6.75 g of 12 as a white crystalline solid.

1-ethoxycarbonyl 4-(diphenylmethylidene)piperidine (19). Alkene-amine 10 (23 g) was suspended in toluene (150 mL), whereupon dry potassium carbonate (13 g) was added. The mixture was then stirred for 15 minutes, filtered, and the filtrate concentrated to yield 18.5 g of purified 1-methyl 4-(diphenylmethylidene)-piperidine. This purified material was dissolved in dry toluene (100 mL), whereupon dry potassium carbonate (38 g, 275 mmol) was added. Ethyl chloroformate (26.7 g, 245 mmol, 3.5 equiv.) was added slowly with stirring and the mixture was heated at reflux overnight. The reaction mixture was cooled to room temperature and the mixture was then filtered. The reaction vessel and filter cake were subsequently washed with toluene (50 mL) and the filtered solid was then partitioned between water (125 mL) and ethyl acetate (100 mL). Stirring was required to dissolve the potassium carbonate within the solid and the layers were subsequently separated. The organic layer was dried with $Na_2SO_4$, filtered, and concentrated to yield 2.9 g of starting amine. The toluene layer obtained from washing the reaction vessel and the filter cake was dried with $Na_2SO_4$, filtered, concentrated, and the residue purified by flash chromatography (5/1 heptane/EtOAc) to yield 11.47 g (51%) of 19. $^1$H NMR confirmed the structure of the product and the starting amine. (Carbamate 21 was similarly prepared.)

4-(diphenylmethylidene)piperidine (20). Sodium hydroxide (15.85 g, 396 mmol) in water (30 mL) was added to the carbamate 1-ethoxycarbonyl 4-(diphenylmethylidene)piperidine 19 (11.47 g, 35.7 mmol) dissolved in ethanol (150 mL). The mixture was heated at reflux overnight. The reaction mixture was cooled to room temperature was then partitioned between water (100 mL) and ethyl acetate (150 mL). The mixture was stirred to dissolve the solid and the layers were separated. The organic layer was washed with brine (100 mL) and the separate aqueous layers were extracted with ethyl acetate (100 mL). The combined organic layers were dried with $Na_2SO_4$, filtered, and concentrated. The yellow oil was dried by high vacuum to give 6.7 g (75%) of 20 as a yellow-white waxy solid. $^1$H NMR was used to confirm the structure of the product. (Amine 22 was similarly prepared.)

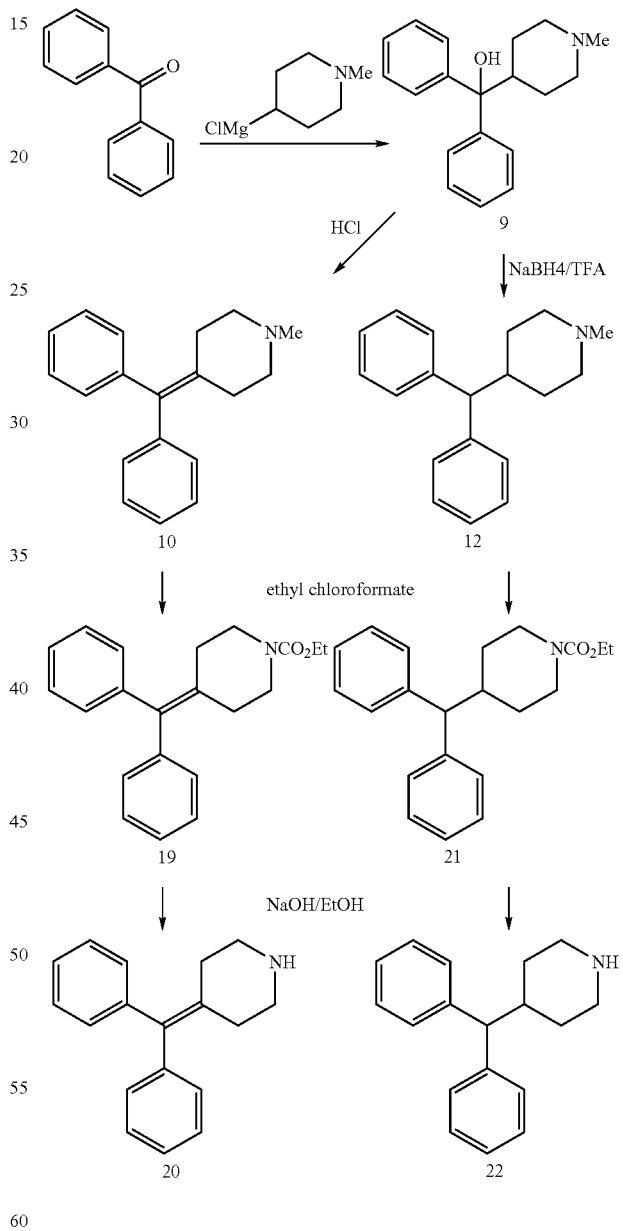

Synthesis of Antihistamines from Intermediates

Several synthetic protocols for the preparation of antihistamines from the synthetic intermediates described in Example 1 are shown below in Examples 2–5 and are further depicted in Scheme 3.

EXAMPLE 2

Pheniramine-like Series 11 Experimental

Isobutyl 3-[4-(diphenylmethylidene)piperidin-1-yl]propanoate (11e). A solution of 20 (0.782 g, 3.14 mmol), isobutyl acrylate (0.56 mL, 3.89 mmol) and ethanol (5 mL) was shaken at 75° C. for 2 h, then evaporated to dryness to give 1.04 g of 11e as a viscous yellow oil that was used without further purification. The structure was confirmed by $^1$H NMR. (Propanoate esters 11b, 11c, and 11f were similarly prepared (see synthesis of cyclopentyl acrylate in the Scheme 6).

Isopropyl 3-[4-(diphenylmethylidene)piperidin-1-yl]propanoate (11d). Sodium hydride (60% dispersion in mineral oil, about 15 mg) was added to a stirred solution of 11b (1.20 g, 3.5 mmol) in 2-propanol (15 mL). Although after 1 h there was no insoluble solid, TLC showed evidence of degradation to the acid 11a, and the mixture was then stirred for an additional 48 h. The mixture was concentrated, suspended in a small amount of 1:1 heptane:ethyl acetate, filtered to remove insoluble solid (323 mg, 11a) and purified by flash chromatography to yield 560 mg (43%) of 11d. The structures were confirmed by $^1$H NMR and LC/MS. (Propanoate ester 11f was similarly prepared (this represents a second method for preparing 11f).)

Cyclopentyl 3-[4-(diphenylmethylidene)piperidin-1-yl]propanoate, oxalic acid salt (11f-Ox). A solution of oxalic acid (190 mg, 2.11 mmol) in ethanol (3 mL) was added in one aliquot to a stirred solution of 11f (885 mg, 2.26 mmol) in warm ethanol (5.5 mL). The mixture became solid after 10 seconds of stirring. The solid mass was broken up and after 1.5 h of stirring, the solid was collected by suction filtration and washed with ethanol. After drying, the oxalate salt 11f-Ox was obtained as white powder (961 mg, 96%). $^1$H NMR, MS, and elemental analyses were consistent with the structure of the product. (The oxalate salt of 11d was similarly prepared.)

Ethyl 3-[4-(diphenylmethylidene)piperidin-1-yl]propanoate, HCl salt (11c-HCl). 2 M HCl/ether (1.45 mL) was added to a stirred solution of 11c (812 mg, 2.32 mmol) in isopropyl ether (40 mL). After stirring for 30 min, the resulting precipitate was filtered, washed with isopropyl ether, and recrystallized from boiling H$_2$O (2 mL) to give 608 mg of the hydrochloride salt of 11c-HCl as a creamy white powder. The structure was confirmed by $^1$H NMR, MS, and elemental analysis. (The HCl salt of 11e was similarly prepared.)

The HCl salt of carboxylic acid 11a was prepared in a manner equivalent to that used to prepare 16a-HCl (see experimental for the 16 series).

EXAMPLE 3

Pheniramine-like Series 13 Experimental

Methyl 3-[4-(Diphenylmethyl)piperidin-1-yl]propanoate (13b). A solution of methyl acrylate (699 mg, 8.12 mmol) in MeOH (3 mL) was added to a solution of 22 (1.99 g, 7.92 mmol) in MeOH (8 mL). After shaking at 75° C. for 3 h, the reaction mixture was evaporated to dryness. Chromatography over silica gel (4:1 heptane/EtOAc) gave 2.54 g of 13b as a colorless viscous oil, which crystallized on standing. The structure was confirmed by $^1$H NMR. (Propanoate esters 13c and 13e were similarly prepared.)

Isopropyl 3-[4-(Diphenylmethyl)piperidin-1-yl]propanoate (13d). A dispersion of NaH (~20 mg of a 60% oil dispersion) was added to a solution of 13b (799 mg, 2.37 mmol) in isopropyl alcohol (10 mL). The resulting mixture was immediately stoppered tightly and stirred at RT for 2 h. The reaction mixture was evaporated to dryness and chromatographed over silica gel using 3:1 heptane/EtOAc to give 0.75 g of 13d as a colorless viscous oil. The structure was confirmed by $^1$H NMR. (Propanoate esters 13e and 13f were similarly prepared using isobutanol and cyclopentanol, respectively (as mentioned above, 13e was also prepared by the previous method using isobutyl acrylate).)

Isobutyl 3-[4-(Diphenylmethyl)piperidin-1-yl]propanoate, oxalic acid salt (13e-oxalate). A solution of oxalic acid (138 mg, 1.53 mmol) in H$_2$O (3 mL) was added to a stirred solution of 13e (583 mg, 1.54 mmol) in ethyl alcohol (3 mL), whereupon no precipitate was formed. Evaporation to dryness gave a solid which was recrystallized from boiling isopropyl alcohol to give 622 mg of the oxalate salt of 13e (13e-oxalate) as a white crystalline solid. The structure was confirmed by $^1$H NMR, MS, and elemental analysis. (Oxalate salts of 13c, 13d, and 13f were similarly prepared.)

Carboxylic acid 13a was prepared in a manner equivalent to that followed to prepare 16a (see experimental for the 16 series).

EXAMPLE 4

Pheniramine-like Series 15 Experimental

Isopropyl [4-(diphenylmethylidene)piperidin-1-yl]ethanoate (15d). A mixture of amine 20 (779 mg, 3.12 mmol), isopropyl bromoacetate (575 mg, 3.18 mmol), K$_2$CO$_3$ (1.34 g, 3 eq), and acetonitrile (28 mL) was stirred at reflux overnight. The reaction mixture was filtered, evaporated to dryness, and then chromatographed over silica gel using 5:1 heptane/EtOAc to give 0.78 g of 15d as an oil that crystallized on standing. The structure was confirmed by 1H NMR. (Acetate esters 15b and 15c were similarly prepared.)

Cyclopentyl [4-(diphenylmethylidene)piperidin-1-yl]ethanoate (15e). A solution of 15b (1.02 g, 3.17 mmol) in anhydrous THF (10 mL) was added (under N$_2$) to a mixture of isobutyl alcohol (10 mL) and sodium hyride (258 mg of a 60% oil dispersion). After stirring for 1 h, the reaction mixture was partitioned between water and EtOAc, wherein a small amount of brine was added to prevent emulsion formation. The organic layer was then removed, the aqueous layer was extracted further with EtOAc, and the combined organics were dried with Na$_2$SO$_4$, filtered, and evaporated to dryness. Chromatography over silica gel using 5:1 heptane/EtOAc gave 0.8 g of 15e as an oil. (Acetate ester 15f was similarly prepared.)

Isopropyl [4-(diphenylmethylidene)piperidin-1-yl]ethanoate, oxalic acid salt (15d-oxalate). A solution of oxalic acid (234 mg, 2.6 mmol) in ethanol (4 mL) was added dropwise to a stirred solution of 15d (910 mg, 2.6 mmol) in ethanol (12 mL). After cooling the reaction mixture to −15° C. for 15 min, the solid was filtered, washed with cold ethanol, and vacuum dried to give 891 mg of 15d-oxalate as a white crystalline solid. The structure of the product was confirmed by $^1$H NMR, MS, and elemental analysis. (The oxalate salts of 15c, 15e, and 15f were similarly prepared.)

EXAMPLE 5

Pheniramine-like Series 16 Experimental

Methyl [4-(Diphenylmethyl)piperidin-1-yl]ethanoate (16b). A mixture of 22 (2.18 g, 8.68 mmol), methyl bromoacetate (1.44 g, 9.39 mmol), acetonitrile (40 mL), and $K_2CO_3$ (5.54 g, 4.6 eq) was stirred at reflux overnight, evaporated to dryness and chromatographed over silica gel using 4:1 heptane/EtOAc to give 1.3 g of 16b as a white solid. The structure was confirmed by $^1$H NMR. (Acetate esters 16c and 16d were similarly prepared.)

Isobutyl [4-(Diphenylmethyl)piperidin-1-yl]ethanoate (16e. A mixture of 16b (700 mg), isobutyl alcohol (10 mL), anhydrous THF (5 mL), and sodium hydride (15 mg of a 60% oil dispersion) was prepared in a sealed vial and was shaken at 75° C. for 3 h, and subsequently poured over a H2O/EtOAc two-phase mixture. The aqueous layer was removed and extracted once with EtOAc. The combined organics were dried with $Na_2SO_4$, filtered, and evaporated to dryness. Chromatography over silica gel using 5:1 heptane/EtOAc gave 665 mg of 16e as a colorless oil. The structure of the product was confirmed by $^1$H NMR. (Acetate ester 16f was similarly prepared.)

Isobutyl [4-(Diphenylmethyl)piperidin-1-yl]ethanoate, oxalic acid salt (16e-oxalate. A mixture of oxalic acid (160 mg), 16e (650 mg), and isopropyl alcohol was evaporated to dryness. The resulting solid was recrystallized from boiling isopropyl alcohol to give 672 mg of the oxalate salt of 16e (16e-oxalate) as a white crystalline solid. The structure of the product was confirmed by $^1$H NMR, MS, and elemental analysis. (The oxalate salts of 16c, 16d, and 16e were similarly prepared.)

[4-(Diphenylmethyl)piperidin-1-yl]ethanoic acid, HCl salt (16a-HCl). A mixture of sodium hydroxide (6.1 g), water (25 mL), and THF (125 mL) was shaken. One fourth of both the bottom and upper layers of the resulting biphasic mixture was added to 747 mg of 16b (2.21 mmol). After stirring overnight, the reaction mixture was diluted with water and EtOAc and then acidified with concentrated HCl. After removing the organic layer, the aqueous layer was extracted twice with EtOAc. The combined organics were dried $Na_2SO_4$, filtered, evaporated to dryness, and moisture removed with ethanol to give 801 mg of 16a-HCl as a glassy solid which was scraped to a powder. $^1$H NMR spectroscopy indicated that the solid consisted of a 9:1 mixture of HCl and acetic acid salts of 16a.

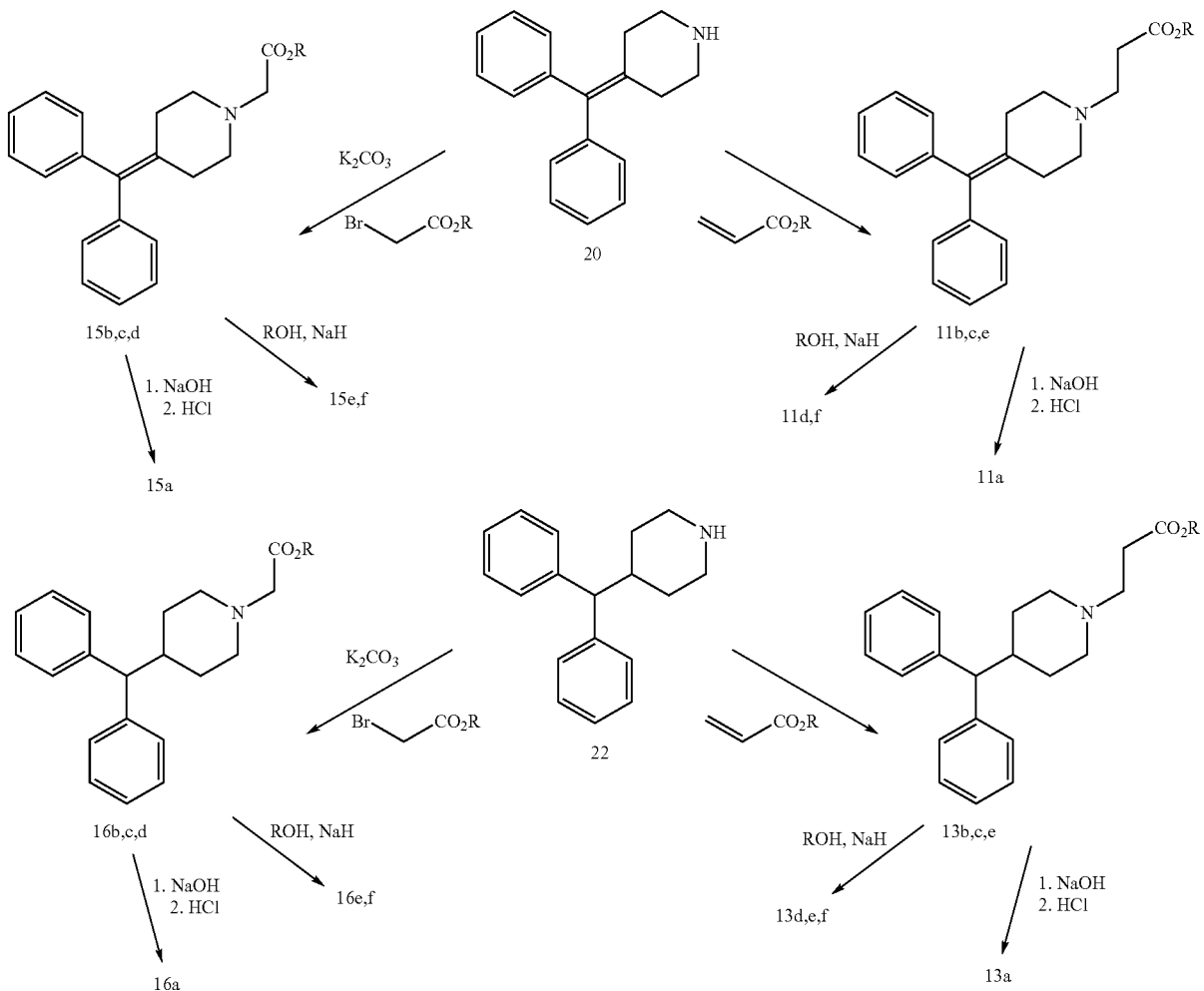

SCHEME 3

Synthesis of Antihistamines

Synthetic protocols for the preparation of antihistamines of Series 6 and 18 are shown below in Examples 6 and 7, respectively, and are further depicted in Schemes 4 and 5, respectively.

EXAMPLE 6

Diphenhydramine-like Series 6 Experimental 4-(diphenylmethoxy)-1-(ethoxycarbonyl)piperidine(4a). 4-(Diphenylmethoxy)-1-(methyl)piperidine (prepared by neutralization of the commercial HCl salt; 4 g, 14.2 mmol, 1 equiv.) in anhydrous toluene (20 mL) was stirred at room temperature under nitrogen. Ethyl chloroformate (4.66 g, 43 mmol, 4.1 mL, 3 equiv.) was added dropwise over 5 minutes, whereupon significant effervescence was noted. The mixture was heated over the course of 1 h to reflux with an oil bath (bath temperature 104° C.). The mixture was then cooled to room temperature, whereupon more ethyl chloroformate (4 mL) was added. The mixture was heated at reflux (bath T=104° C.) for 7 h and again cooled to room temperature. The cooled mixture was concentrated and the residue purified by dry column chromatography (4×8.5 cm silica bed; 2:1 heptane:ethyl acetate) to yield 3.49 g (72%) of 4a as a slightly yellow oil. 1H NMR was consistent with the structure.

4-(diphenylmethoxy)piperidine (5). 4-(Diphenylmethoxy)-1-(ethoxycarbonyl)piperidine (4a) (11.45 g, 33.7 mmol) was dissolved in ethanol (72 mL). A cold solution of sodium hydroxide (8.2 g, 205 mmol) in water (12 mL) was added slowly and a small amount of heat was detected. The mixture was heated at reflux for 17 h and then cooled to room temperature. The mixture was subsequently diluted with water (100 mL) and ethyl acetate (100 mL) and stirred for 0.5 h to dissolve the resultant solid. The organic and aqueous layers were separated and the organic layer was washed with water (100 mL). The separate aqueous layers were extracted with ethyl acetate (100 mL) and the organic layers were combined, dried with Na$_2$SO$_4$, filtered and concentrated to yield 7.88 g (87.5%) of 5 as a viscous yellow oil. The structure was confirmed by $^1$H NMR.

Methyl 3-[4-(diphenylmethoxy)piperidin-1-yl]propanoate (6b). A solution of 4-(diphenylmethoxy)piperidine (5) (1.4 g, 5.2 mmol), methyl acrylate (560 mg, 6.5 mmol) and methanol (9.5 mL) was placed on a preheated orbital shaker at 75° C. for 3 h. The yellow solution was concentrated to yield 1.8 g (98%) of 6b as a yellow oil. The structure was confirmed by $^1$H NMR. (The propanoate esters 6c and 6e were similarly prepared.)

Isopropyl 3-[4-(diphenylmethoxy)piperidin-1-yl]propanoate (6d). Oxalyl chloride (7.27 g, 57.3 mmol, 5 mL) was added in one aliquot, with stirring, to a pre-cooled (ice bath) solution of 6a-HCl (1.14 g, 3.0 mmol) in dry THF. Once the initial effervescence ceased, the flask was sealed under nitrogen and the mixture was stirred for 1.75 h. The magnetic stirring bar was washed with dry THF upon its removal from the solution mixture and the mixture was then concentrated on a rotary evaporator to give a yellow-white solid. The solid was dried under high vacuum for 1 h. The solid was then suspended in 2-propanol (15 mL) and 4-ethylmorpholine (440 mg, 400 µL, 3.8 mmol, 1.28 equiv.) was added. Vapors formed above the suspension and the slurry became an orange-yellow solution after about 2 minutes. After having been stirred for 2.5 days, the reaction mixture was concentrated. The residue was dissolved in dichloromethane (25 mL) and washed with 1 N KOH (15 mL). The layers were separated and the aqueous layer was extracted with dichloromethane (25 mL). Both organic layers were washed with water (25 mL), combined, dried with Na$_2$SO$_4$, filtered and concentrated to yield 976 mg (84%) of a dark orange-yellow oil. This oil was purified by flash chromatography (2:1 heptane:ethyl acetate) to yield 774 mg (67%) of 6d as a yellow oil. $^1$H NMR and LC/MS confirmed the structure. (The propanoate ester 6f was similarly prepared.)

Isopropyl 3-[4-(diphenylmethoxy)piperidin-1-yl]propanoate (6d), Alternate procedure. Sodium hydride (60% dispersion in mineral oil, about 15 mg) was added to a stirred solution of 6b (384 mg, 1.09 mmol) in 2-propanol (8 mL). Although after only 1 h there was no insoluble solid, TLC showed evidence of degradation to the acid 6a. After confirmation by TLC that the reaction was complete, the mixture was concentrated and dissolved in a small amount of 2:1 heptane:ethyl acetate for flash chromatography. The insoluble solid was isolated by filtration (58 mg) and was shown to be 6a. The solution was purified by flash chromatography to yield 300 mg (72%) of 6d as a colorless oil. Purity (LC/MS): 99.6% (m/z=381). (The propanoate ester 6f was also prepared by this alternate procedure.)

3-[4-(diphenylmethoxy)piperidin-1-yl]propanoic acid hydrochloride (6a-HCl). A solution of sodium hydroxide (1.3 g, 32.5 mmol, 1.98 equiv.) in water (16 mL) was slowly added to a stirring solution of 6b (5.8 g, 16.4 mmol) in methanol (58 mL) at room temperature, resulting in a slight increase in temperature. The solution was heated at reflux for 1.25 h, cooled to room temperature, and concentrated. The resulting residue was dissolved in water (75 mL) and the pH was adjusted to 2 with concentrated HCl (about 2.5 mL). The thick mixture was then extracted with chloroform (3×80 mL; 6a-HCl is soluble in chloroform) and the combined organic layers were washed with brine (100 mL). The organic layers were dried with Na$_2$SO$_4$, filtered, and concentrated to give 6a-HCl as white needles (5.3 g, 86%). The structure was confirmed by $^1$H NMR and LC/MS.

Ethyl 3-[4-(diphenylmethoxy)piperidin-1-yl]propanoate, oxalic acid salt (6c-Ox). A solution of oxalic acid (130 mg, 1.44 mmol) in ethanol (3 mL) was added in one aliquot to a stirred solution of ethyl 3-[4-(diphenylmethoxy)piperidin-1-yl]propanoate 6c (530 mg, 1.44 mmol) in ethanol (3 mL). The mixture became solid at the end of the addition, whereupon more ethanol (2 mL) was added to facilitate stirring. After 1 h of stirring, the solid was collected by suction filtration and washed with ethanol (2 mL). After drying, the oxalate salt 6c-Ox was obtained as white powder (595 mg, 90%). $^1$H NMR, LC/MS, and elemental analysis were consistent with the structure. (The oxalate salts of 6d, 16e, and 6f were similarly prepared.)

SCHEME 4

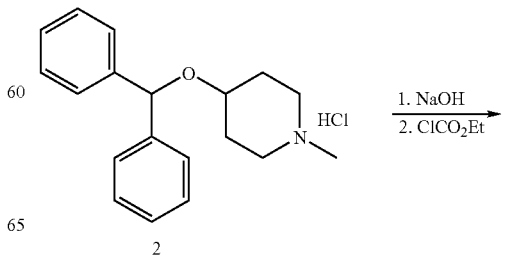

2

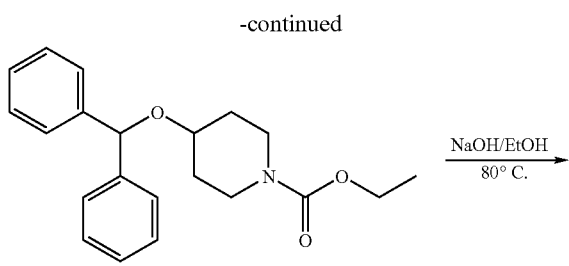

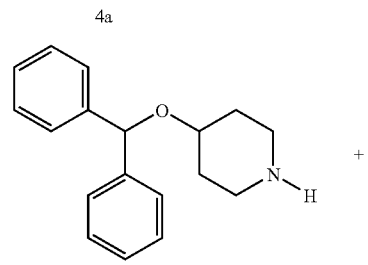

EXAMPLE 7

Pheniramine Analog Series 18 Experimental 4-(3-dimethylamino-1-(2-pyridyl)propyl)benzoic acid (qa). (+/−)-Brompheniramine 17 (obtained by neutralization of the maleate salt; 38 g, 120 mmol) was dissolved in dry THF under nitrogen and the solution was cooled in a dry ice/acetone bath. n-butyllithium (1.6 M, hexanes, 90 mL, 144 mmol) was added dropwise to the reaction mixture to give a red solution. After 2 h of stirring, carbon dioxide was bubbled into the solution as the bath slowly warmed to room temperature. The resulting mixture was stirred overnight and the reaction was quenched with water (500 mL). The aqueous layer was extracted with ethyl acetate (2×500 mL). The organic layer was discarded and the aqueous layer was concentrated to a yellow paste. The paste was digested in sodium hydroxide (1 N, 150 mL) and chloroform (200 mL) and the layers were separated. The aqueous layer was extracted with chloroform (200 mL) and ethyl acetate (2×150 mL). The chloroform layers were concentrated to yield unreacted 17 (17 g, 44%). The ethyl acetate layers were concentrated to 1.4 g of a complex mixture which was discarded. The aqueous layer was concentrated to a thick oil, filtered to remove insoluble solid, and dissolved in ethanol (100 mL) and water (40 mL). The pH was adjusted to 2 by the careful addition of concentrated HCl (about 17 mL). The resulting solution was concentrated, dissolved in 1:1 methanol:ethanol, filtered to remove insoluble NaCl and concentrated to a brown oil (13 g). The oil was purified by column chromatography (8.5/1/0.5 $CH_2Cl_2$/MeOH/triethylamine) to yield 18a as a white solid (3 g, 8%). The structure was confirmed by $^1$H NMR, LC/MS, and elemental analysis.

Ethyl 4-[3-dimethylamino-1-(2-pyridyl)propyl]benzoate (18c). Acid 18a (927 mg, 3.26 mmol) was stirred in oxalyl chloride (5 mL) at room temperature for 2 minutes and dry toluene (4 mL) was added to facilitate stirring. After 1 h, the mixture was concentrated. Ethanol (10 mL) and triethylamine (1.35 mL) were added and the dark yellow mixture was stirred overnight. The mixture was then concentrated and partitioned between ethyl acetate (25 mL) and water (25 mL). The layers were separated and the aqueous layer was extracted with ethyl acetate (10 mL). The combined organic layers were washed with water (20 mL) and the combined aqueous layers were extracted with ethyl acetate (20 mL). The combined organic layers were dried with $Na_2SO_4$, filtered, and concentrated to yield 18c as an oil. Purification by flash chromatography (4/1 CH₂Cl₂/MeOH) yielded 18c (136 mg) as a yellow oil. The structure was confirmed by ¹H NMR and LC/MS. (Esters 18d, 18e, and 18f were similarly prepared.)

Ethyl 4-(3-dimethylamino-1-(2-pyridyl)propyl)benzoate, oxalic acid salt (18c-Ox). A solution of oxalic acid (52 mg, 0.58 mmol) in ethanol (0.5 mL) was added in one aliquot to a stirred solution of 18c (185 mg, 0.59 mmol) in ethanol (0.5 mL). The mixture became solid after 30 seconds of stirring. The solid mass was broken up, ethanol (0.75 mL) was added, and the solid was collected by suction filtration after 1.5 h of stirring and subsequently washed with ethanol. After drying, the oxalate salt 18c-Ox was obtained as white powder (167 mg, 72%). ¹H NMR, LC/MS, and elemental analyses were consistent with the structure of the product. (The oxalate salt of 18e was prepared similarly.)

scheme 5

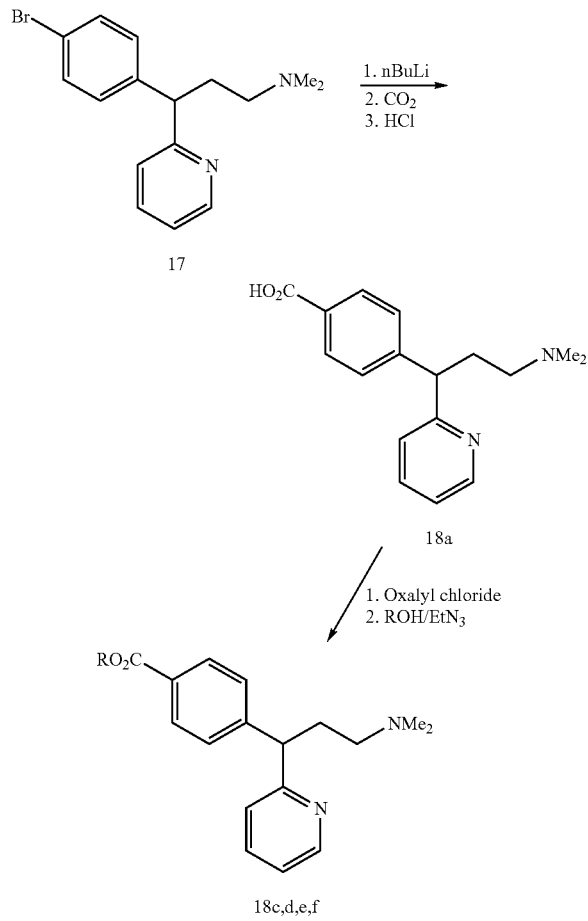

Synthesis of Triprolidine Series

Synthetic protocols for the preparation of the triprolidine series are shown below in Examples 8 and are further depicted in Scheme 6.

EXAMPLE 8

Triprolidine-Like Series 7 Experimental

6-Bromo-2-pyridyl 4-tolyl ketone (3). A solution of 1 (50.02 g, 0.211 mol) was added to a stirred and cooled (−78° C.) solution of 1.6 M n-BuLi/hexanes (132 mL) over a period of 1 h and 20 min. After an additional 15 min at −78° C., a solution of p-tolunitrile (25.64 g, .219 mol) in anhydrous THF (100 mL) was added rapidly (4 min) and the reaction mixture was stirred for another 4.75 h. During this time the temperature was controlled to rise slowly from −78° C. to −20° C. The reaction was stirred at room temperature overnight and then quenched by the addition of 2 N HCl (500 mL). The organic layer was dried with Na₂SO₄, filtered, and evaporated to a solid. Recrystallization from boiling ethanol gave 36.74 g of ketone 3 as an off-white crystalline solid. The structure of the product was confirmed by ¹H NMR.

Cyclopentyl acrylate. Acryloyl chloride (75 mL) was added to a stirred solution of cyclopentanol (88 g, 1 mol) and triethylamine (175 mL) in dry THF (500 mL) at a rate slow enough to prevent overheating of the reaction. The reaction mixture was allowed to stand overnight, filtered through a pad of Celite, evaporated to an oil, and distilled to give cyclopentyl acrylate as a colorless liquid (bp 74–79/~60 mm Hg). The structure of the product was confirmed by ¹H NMR.

Ethyl (E)-3-[6-(4-toluoyl)-2-pyridyl]acrylate (5c). A mixture of ketone 3 (16.90 g, 61.2 mmol), triphenylphosphine (1.64 g, 6.25 mmol), tributylamine (15 mL), and ethyl acrylate (16 mL) was stirred and heated (hot bath at 125–135° C.) for 7 h. Two additional aliquots of ethyl acrylate (7 mL each) were added at 4 h and 6 h. After the reaction was cooled to room temperature, the reaction mixture was poured over water (300 mL) and EtOAc (300 mL). The aqueous layer was extracted further with EtOAc. The combined organics were dried with Na₂SO₄, filtered, and evaporated to dryness. Chromatography over silica gel using heptane/EtOAc (starting at 8:1) gave 15.49 g of 5c as a yellow crystalline solid. The structure was confirmed by ¹H NMR. (Keto-acrylates 5e and 5f were similarly prepared using isobutyl acrylate and cyclopentyl acrylate, respectively.)

(2-pyrrolidinoethyl)triphenylphosphonium bromide. A mixture of 2-phenoxyethyl bromide (90.6 g, 0.45 mol), triphenylphosphine (119.2 g, 0.45 mol), and phenol (854 g) was heated to a melt and then stirred over a hot oil bath (107–114° C.) for ~24 h. The reaction mixture was extracted with 6:1 heptane/EtOAc (3×2 L), 9:1 heptane/EtOAc (3×0.5 L), and heptane (300 mL) to give an oil that solidified. After dissolving the reaction mixture in DMSO, the mixture was warmed, treated with pyrrolidine (150 mL), and stirred over a hot oil bath (50–55° C.) for 1.5 h. The reaction mixture was cooled to room temperature, seeded for crystallization, and treated slowly and intermittently with increasing amounts of t-butyl methyl ether (TBME) until it was evident that crystallization was complete. The solid was filtered, washed with TBME and then with heptane, and vacuum dried to give 90.27 g of the desired product. The structure was confirmed by ¹H NMR.

Triprolidine E,E-7c. A solution of 25 mL of 1.6 M n-BuLi/hexanes was added to a stirred and cooled (0° C.) suspension of (2-pyrrolidinoethyl)triphenylphosphonium bromide (17.24 g, 39.18 mmol) in dry THF (250 mL) over a period of ~4 min. The ylide-forming reaction mixture was stirred an additional 10 min at 0° C., followed by the addition of one aliquot of a solution of 5c (4.52 g, 15.3 mmol) in dry THF (75 mL). After stirring at 0° C. for only 2 min, the reaction mixture was quenched by the addition of water (100 mL). The reaction mixture was then extracted twice with EtOAc and the combined organics were dried with Na₂SO₄, filtered, and evaporated to dryness. Chromatography over silica gel using MeOH/EtOAc (starting at 5% MeOH) gave 1.42 g (25%) of E,E-7c as a yellow crystalline solid and 2.42 g (42%) of E,Z-7c. The structure of the products were confirmed by ¹H NMR and MS. (Triprolidine ester E,E-7e was similarly prepared.)

Triprolidine E,E-7f. Sodium hydride (25 mg of a 60% oil dispersion) was added to a solution of E,E-7c (1.116 g, 2.96 mmol) in cyclopentanol (10 mL) and dry THF (8 mL). After stoppering the reaction flask, the reaction mixture was stirred at room temperature for 1.5 h and quenched by the addition of saturated brine (30 mL). The mixture was extracted twice with EtOAc and the combined organics were dried with Na$_2$SO$_4$, filtered, and evaporated to dryness. Chromatography over silica gel using MeOH/EtOAc (starting at 2% MeOH) gave 1.04 g of the desired product as a viscous oil. The structure of the product was confirmed by ¹H NMR. (Triprolidine esters E,E-7d was similarly prepared.)

Triprolidine E,E-7e-oxalate. A solution of oxalic acid (362 mg, 4 mmol) in ethanol (4 mL) was added to a stirred solution of E,E-7e (1.63 g) in EtOH. After evaporating to dryness, the resulting oil was dissolved in EtOAc and again evaporated to dryness, whereupon a solid was generated. Recrystallization from boiling EtOAc gave 1.59 g of the oxalate salt of as an off-white powder. The structure was confirmed by ¹H NMR, MS, and elemental analysis. (The oxalate salts of the E,E-isomers of 7c, 7d, and 7f were similarly prepared.)

SCHEME 6

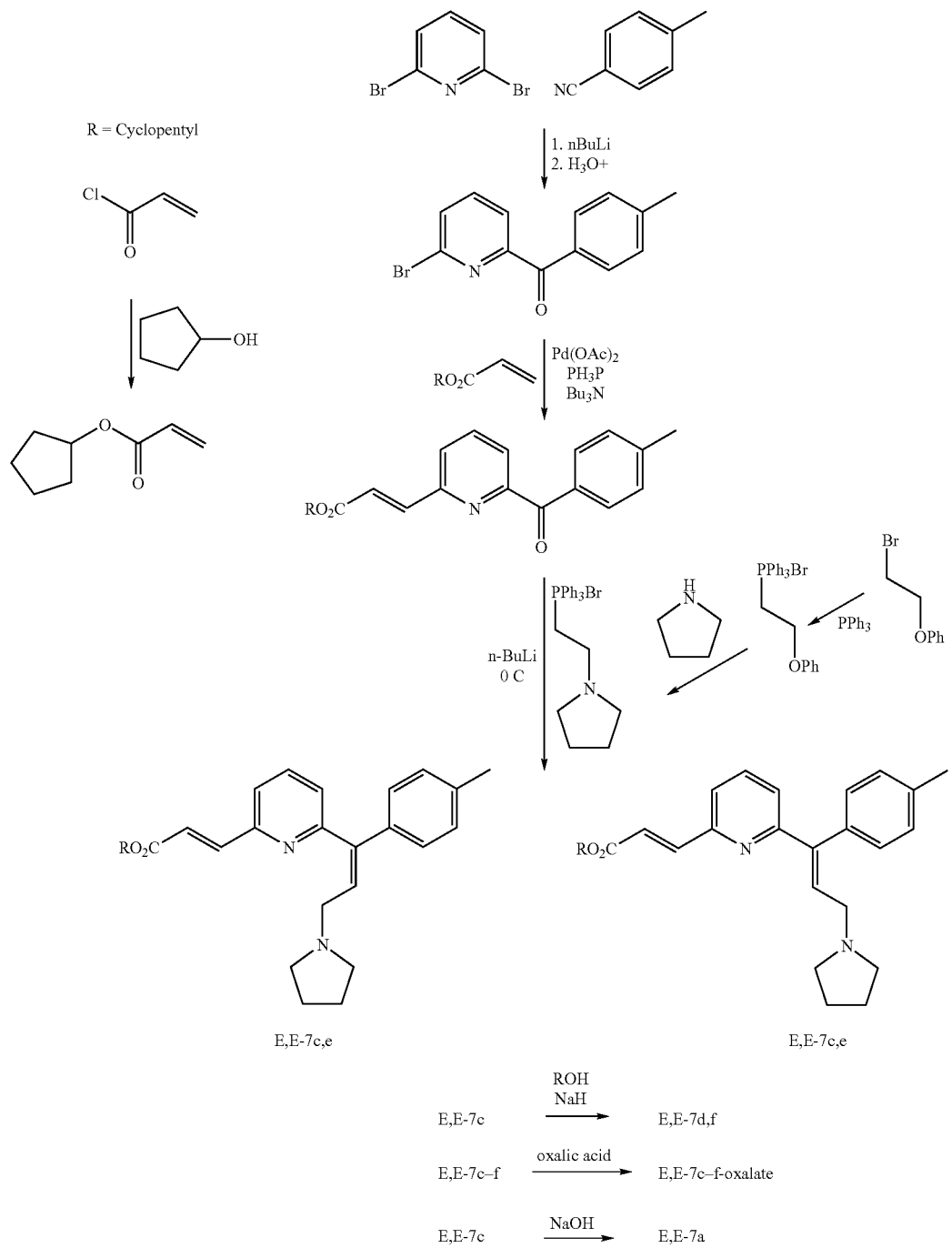

Triprolidine acid E,E-7a was prepared in a manner similar to that used to prepare acids 11a, 13a, 15a, and 16a described above.

EXAMPLE 9

Doxepin-like Series Experimental

Step 1:

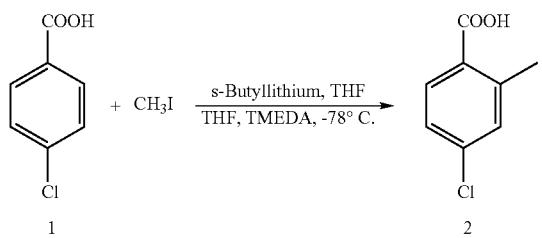

A mixture of THF (150 mL) and N,N,N', N'-tetramethylethylenediamine (27.8 mL, 0.1853 mol, 2.5 eq.) was cooled to −78° C. s-Butyllithium (0.2 mol) was added slowly (40 min) maintaining the temperature between −65 to −78° C. After an additional 20 min stirring, 4-chlorobenzoic acid (11.60 g, 0.0741 mol, 1.0 eq.) dissolved in THF (150 mL) was added over a period of 60 minutes while maintaining the temperature between −65 to −78° C. After 2 h, iodomethane added, and stirring continued for 1 hour, at which time the cooling bath was removed. Water (164 mL) was added slowly and the reaction mixture was allowed to warm to room temperature. The layers were then separated, and the aqueous layer was washed with tert-butyl methyl ether (3×100 mL), and acidified with HCl to pH 1–2. The product was subsequently collected by filtration, washed with water, and dried under vacuum at 60° C. to give compound 2 (10.63 g, 84.0%). $^1$H NMR was consistent with the structure.

Step 2:

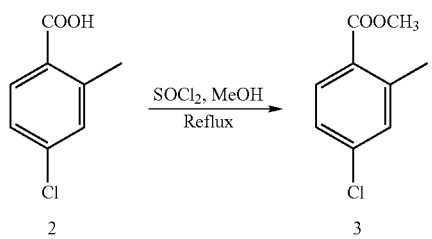

Compound 2 (10.62 g, 62.3 mmol, 1.0 eq.) was dissolved in methanol (200 mL) and thionyl chloride (11.3 mL, 155.25 mmol, 2.5 eq.) was added slowly. The reaction solution was refluxed for 5 h, the solvent was removed, and the oil was taken up in methylene chloride (200 mL). The organic layer was washed with H$_2$O (3×100 mL), dried over MgSO$_4$, filtered, concentrated, and dried to give compound 3 (10.86 g, 94.4%). The structure was confirmed by $^1$H-NMR.

Step 3:

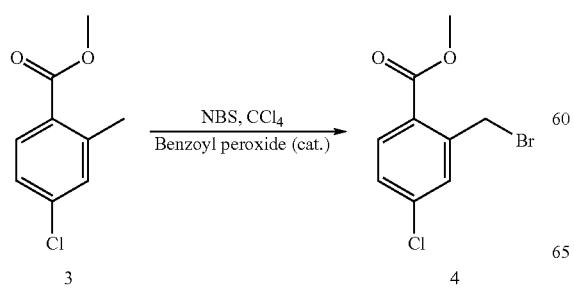

Compound 4 (10.86 g, 58.8 mmol, 1.0 eq.) was dissolved in carbon tetrachloride (100 mL), and N-bromosuccinimide (15.7 g, 88.2 mmol., 1.5 eq.) was added followed by benzoylperoxide (0.05 g). The mixture was refluxed overnight. The reaction mixture was then filtered, and the solids were washed with dichloromethane. The combined organic filtrate was concentrated and dried to give compound 4 (7.1 g, 45.8%). The structure was confirmed by $^1$H NMR.

Step 4:

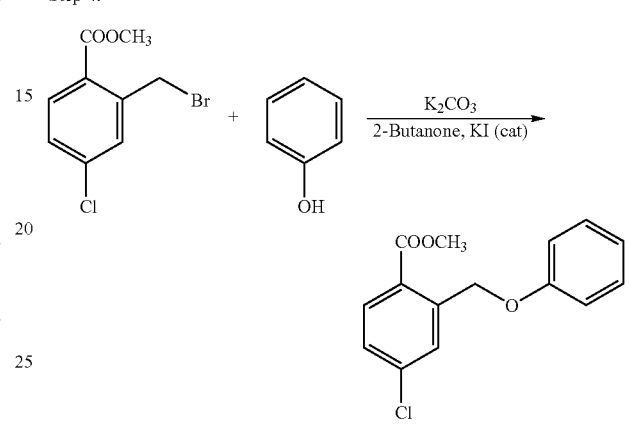

Phenol (2.79 g, 29.63 mmol, 1.1 eq.) was dissolved in 2-butanone (75.0 mL) and potassium carbonate (11.17 g, 80.82 mmol., 3.0 eq.) was added, followed by compound 4 (7.1 g, 26.94 mmol., 1.0 eq.) dissolved in 2-butanone (75.0 mL). A catalytic amount of potassium iodide (0.05 g) was added and the mixture was refluxed overnight. The cooled reaction mixture was filtered and the solids were washed with 2-butanone. The combined filtrate was taken up in ethyl acetate (75 mL) and was washed with 5% aqueous NaOH (2×50 mL), brine (40 mL), and water (50 mL). The organic phase was concentrated and purified on silica gel to give compound 5 (9.32 g). The structure confirmed product by $^1$H NMR Step 5:

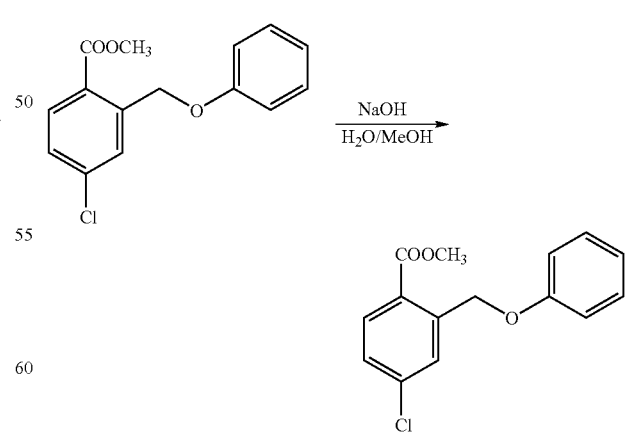

A solution of NaOH (4.0g, 3.0 eq.) in H$_2$O (20 mL) was added to compound 5 (9.32 g, 1.0 eq.) dissolved in MeOH (50 mL), and refluxed for 45 min. After cooling, the solvent was removed, H₂O added (100 mL), and aqueous layer (aq. Extract-1) washed with ethyl acetate. The product was extracted into the ethyl acetate layer. The organic phase was then washed with water/5% NaOH (3×75 mL) (aq. Extract-2). Each of the aqueous extracts 1 and 2 (which were not combined) was acidified to pH 1–2 with HCl. The white precipitate obtained was taken up in dichloromethane (3×75 mL). After removal of the solvent and drying, aq. Extract-1 gave 1.61 g solid containing some product but mostly compound 1, and aq. Extract-2 gave 5.68 g product (compound 6). The structures were confirmed by ¹H NMR.

Step 6:

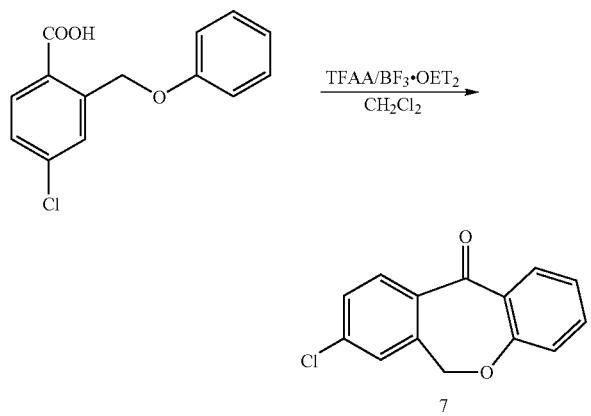

Compound 6 (6.0 g, 22.84 mmol., 1.0 eq.) was dissolved in dichloromethane (75.0 mL) and trifluoroacetic anhydride (7.2 g, 34.26 mmol., 1.5 eq.) was added, followed by a catalytic amount of borontrifluoride etherate (0.4 mL). Reaction mixture was heated to 40° C. for 4 h. The reaction mixture was washed with water (50 mL), saturated NaHCO₃ (2×50 mL), and water (50 mL). The organic phase was dried over MgSO₄, filtered and concentrated. The crude product was purified on 120 g RediSep column using gradient elution, heptane/ethylacetate to give compound 7 (3.69 g, 66.0%). The structure was confirmed by ¹H NMR and LC/MS.

Step 7:

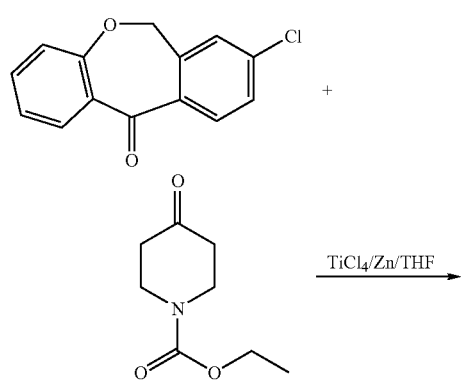

-continued

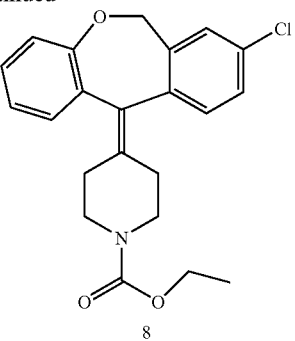

The ketone 7, was subjected to McMurray reaction. Accordingly, titanium chloride (4.05 mL, 36.85 mmol.) was slowly added to a mixture of zinc dust (5.31 g, 81.2 mmol., 5.4 eq.) in anhydrous THF (60 mL) at 0° C. The mixture was then refluxed for 2.5 hours. N-carbethoxy-4-piperidone, (5.5 mL, 36.3 mmol., 2.4 eq.) and ketone 7 (3.69 g, 15.12 mmol., 1.0 eq.) were dissolved in anhydrous THF (40.0 mL) and added to the titanium (0) mixture, and the reaction mixture was refluxed for 6 h. An aq. solution of K₂CO₃ (150 mL of 10% aqueous solution) was then added and stirred for 30 min. The mixture was subsequently filtered over pad of celite, and the solids were washed with ethylacetate. The layers were separated and the organic phase was collected, dried over MgSO₄, and concentrated to give the compound 8 (8.15 g, 80.0% pure by HPLC). The structure was confirmed by ¹H NMR and LC/MS.

Step 8:

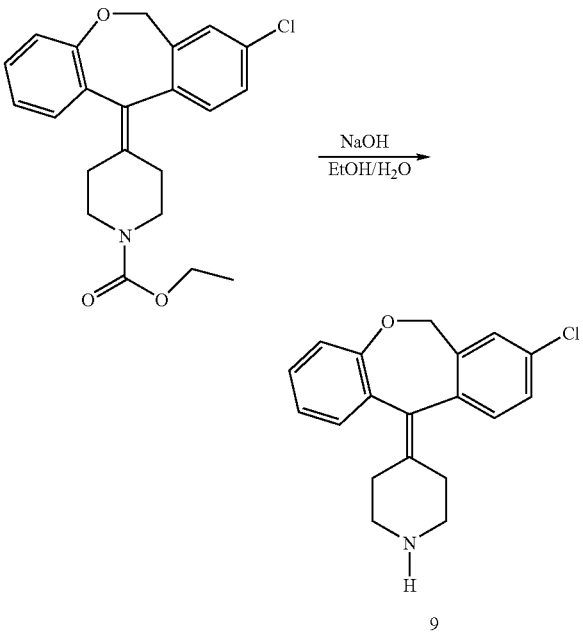

Compound 8 was dissolved in ethanol (60.0 mL), and an aq. solution of sodium hydroxide (10.2 g, 254.76 mmol., 12.0 eq.) in H₂O (15.0 mL) was added and refluxed overnight. The solids were filtered off, and then washed with ethanol. The filtrate was concentrated and the oily residue was taken up in dichloromethane (155 mL) and H₂O (40 mL). The aqueous layer was extracted with CH₂Cl₂ (3×50 mL) and combined with the organic layer. The combined organic phase was washed with brine, dried over NaSO₄, filtered and concentrated to give 3.95 g of crude compound 9. The structure of compound 9 was confirmed by ¹H NMR and LC/MS and the crude material was taken to the next step without purification.

Step 9:

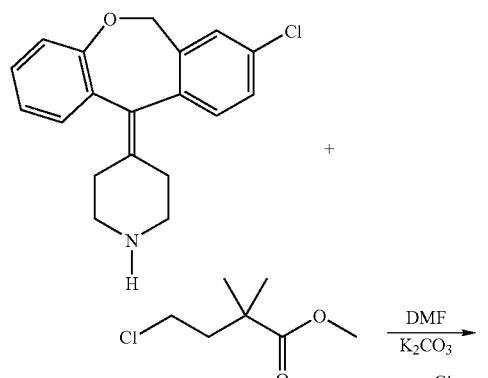

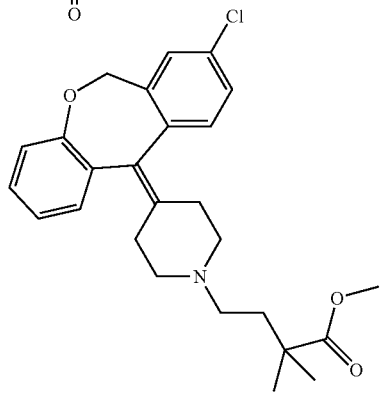

Compound 9 (2.0 g, 6.41 mmol., 1.0 eq.), K₂CO₃ (1.77 g, 12.82 mmol., 2.0 eq.), halide (5.28 g, 32.05 mmol., 5.0 eq.) and DMF (25.0 mL) were combined and heated to 100° C. overnight. The crude reaction mixture was mixed with H₂O (30 mL) and CH₂Cl₂ (35 mL). The organic phase was separated and the aqueous phase was washed with CH₂Cl₂ (2×25 mL). The combined organic phase was washed with brine and concentrated. The crude material was purified on a silica column to give compound 10 (1.2 g). The structure was confirmed by ¹H NMR and LC/MS.

Step 10:

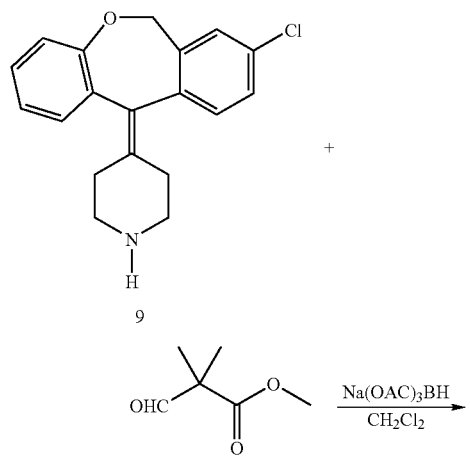

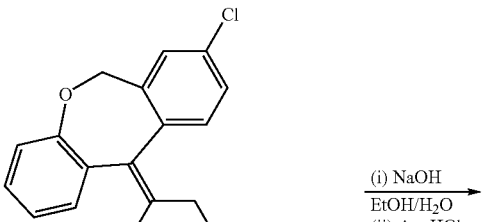

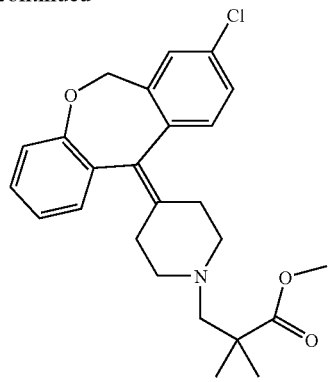

Compound 9 (2.0 g, 6.41 mmol, 1.0 eq.), aldehyde (1.7 g, 13 mmol, 2.0 eq.) and CH₂Cl₂ (20 mL) were taken in a flask under nitrogen and cooled to 0° C. Na(OAc)₃BH (2.6 g, 12.32 mmol, 1.9 eq.) was added in controlled aliquots and stirred at 0° C. for 30 min. the reaction mixture was allowed to reach room temperature and stirred overnight. The mixture was then diluted with CH₂Cl₂ (40 mL), an aq. solution of satd. NaHCO₃ (30 mL) was subsequently added, and the reaction mixture was stirred for 10 min. The organic phase was separated and the aq. phase was extracted with CH₂Cl₂ (2×25 mL). The combined organic layer was dried (NaSO₄), concentrated, and the crude material was purified on a silica column to; give compound 11 (1.72 g). The structure was confirmed by ¹H NMR and LC/MS.

Step 11:

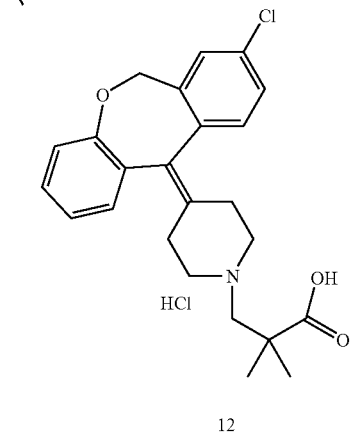

Compound 11 (1.6 g, 3.76 mmol, 1 eq.) was dissolved in ethanol (40.0 mL). An aq. solution of sodium hydroxide (2.0 g, 50 mmol., 13.0 eq.) in $H_2O$ (9.0 mL) was added and refluxed overnight. The solids were filtered off, and the solvents were then distilled off. The residue was taken up in $H_2O$ (40 mL) and acidified with HCl to pH 1 and stirred for 20 min. The resulting solids were filtered, washed with heptane, and dried under high vacuum to give the compound 12 (1.59 g). The structure of the compound 12 was confirmed by $^1H$ NMR, LC/MS and elemental analysis.

Schemes 7 through 15, shown below, depict the synthesis of several doxepin-like compounds of the invention, with various degrees of substitution (i.e., various substituents at the $R_1$ and $R_2$ positions, on the spacer molecule, and combinations thereof)

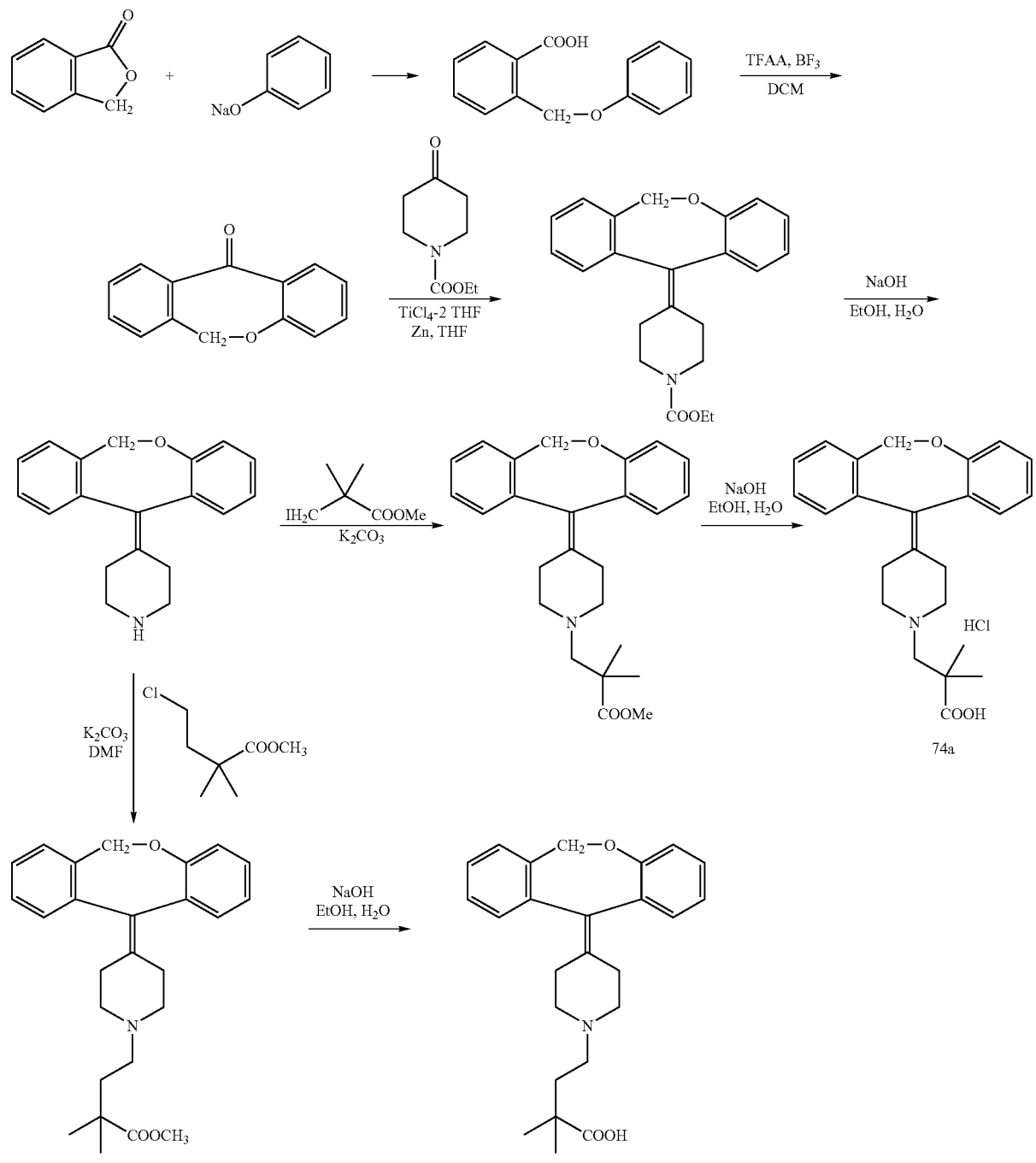

SCHEME 8
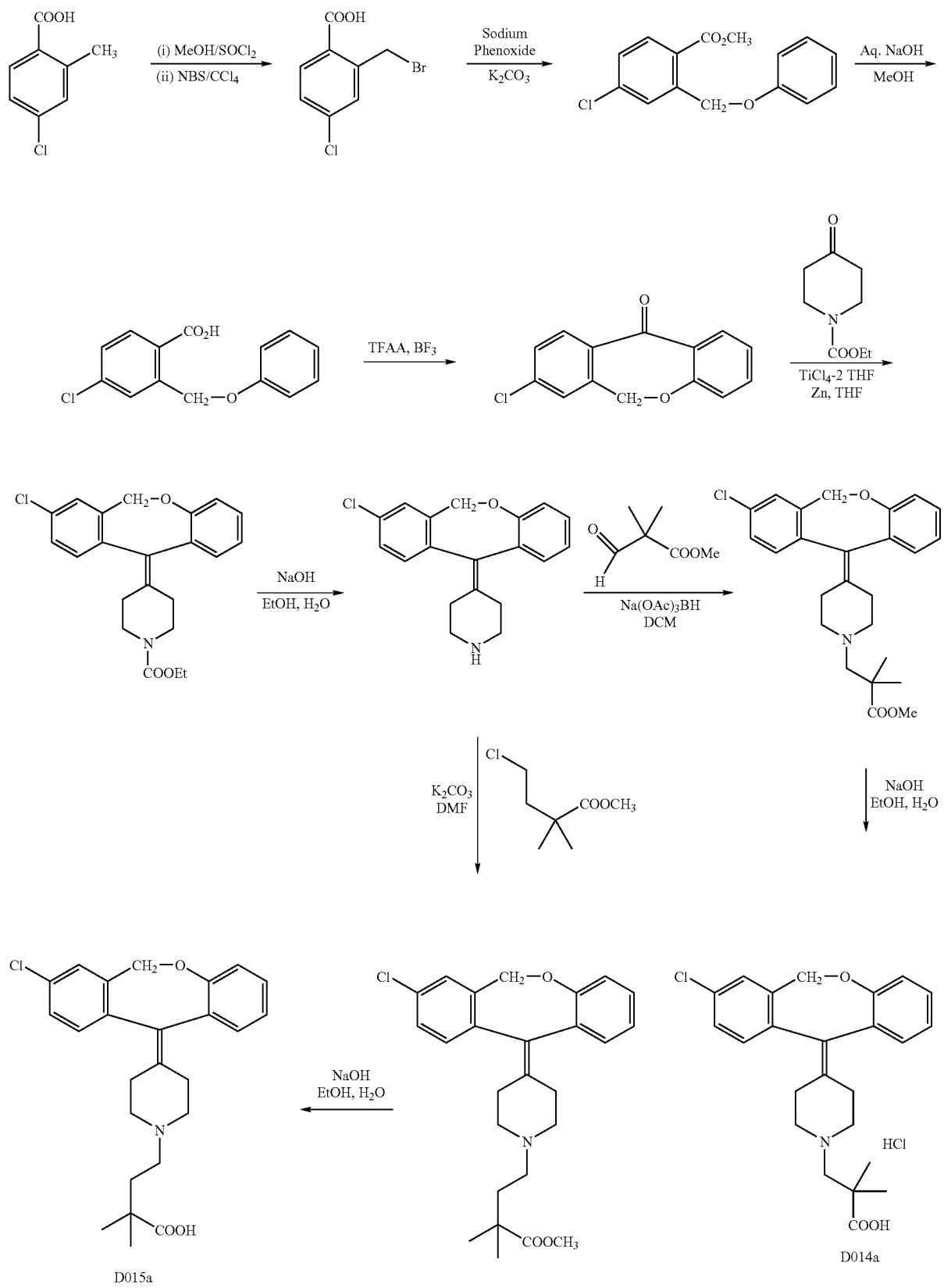

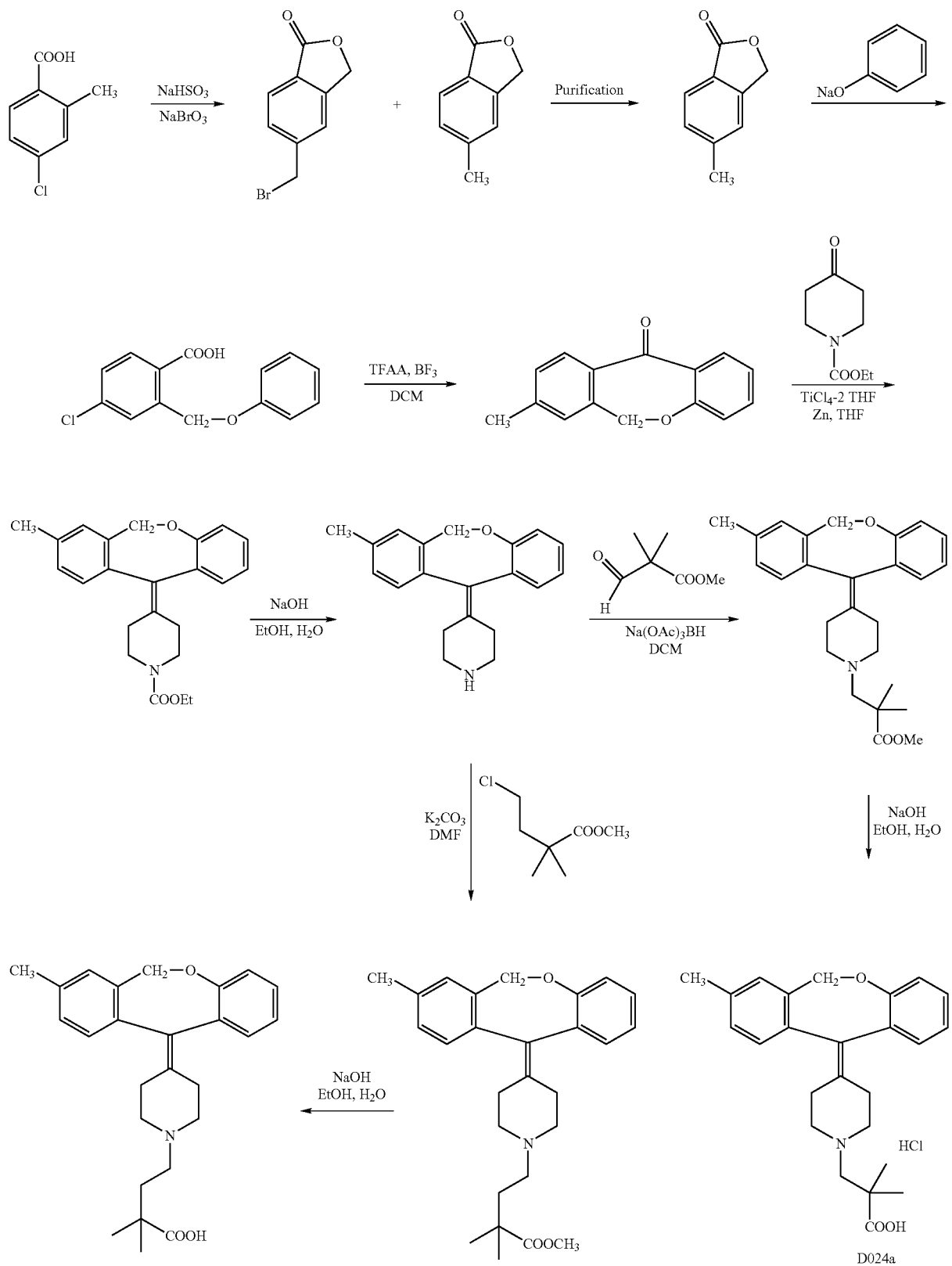

123
SCHEME 10A
124
-continued
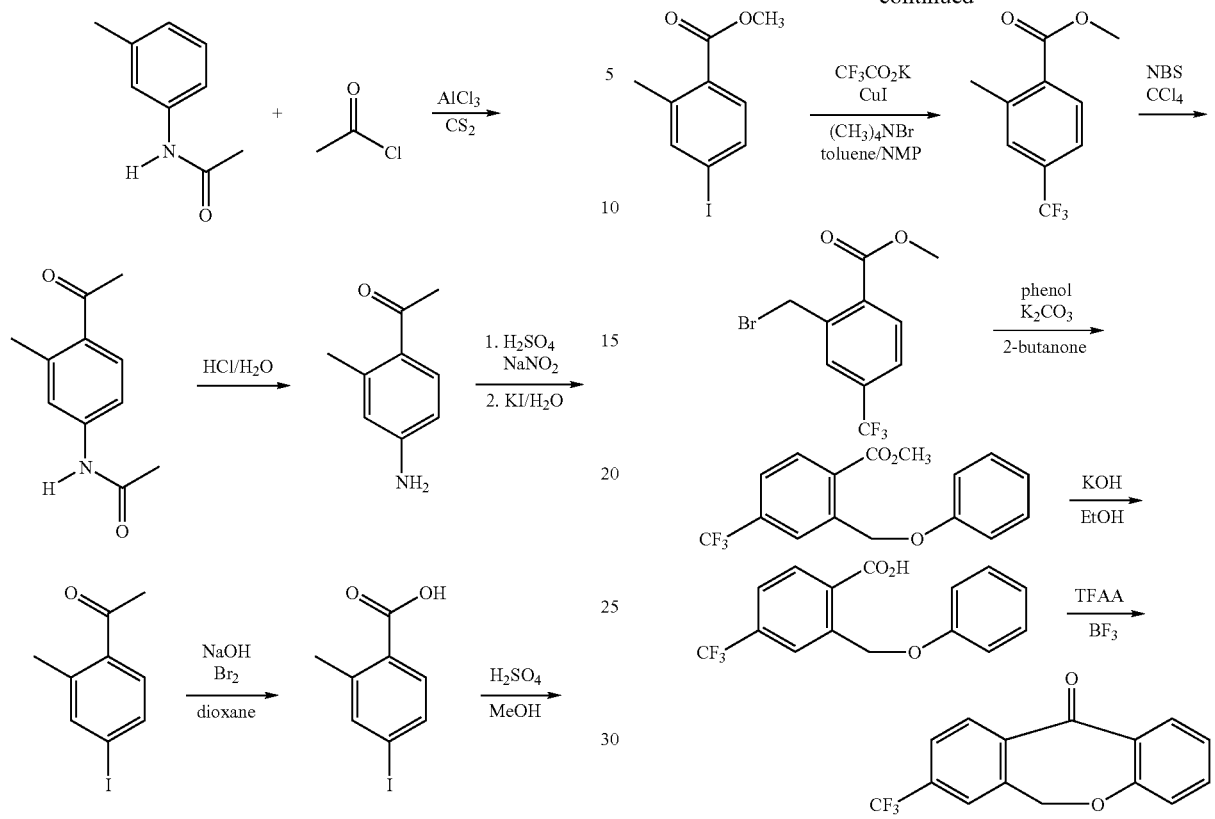
SCHEME 10B
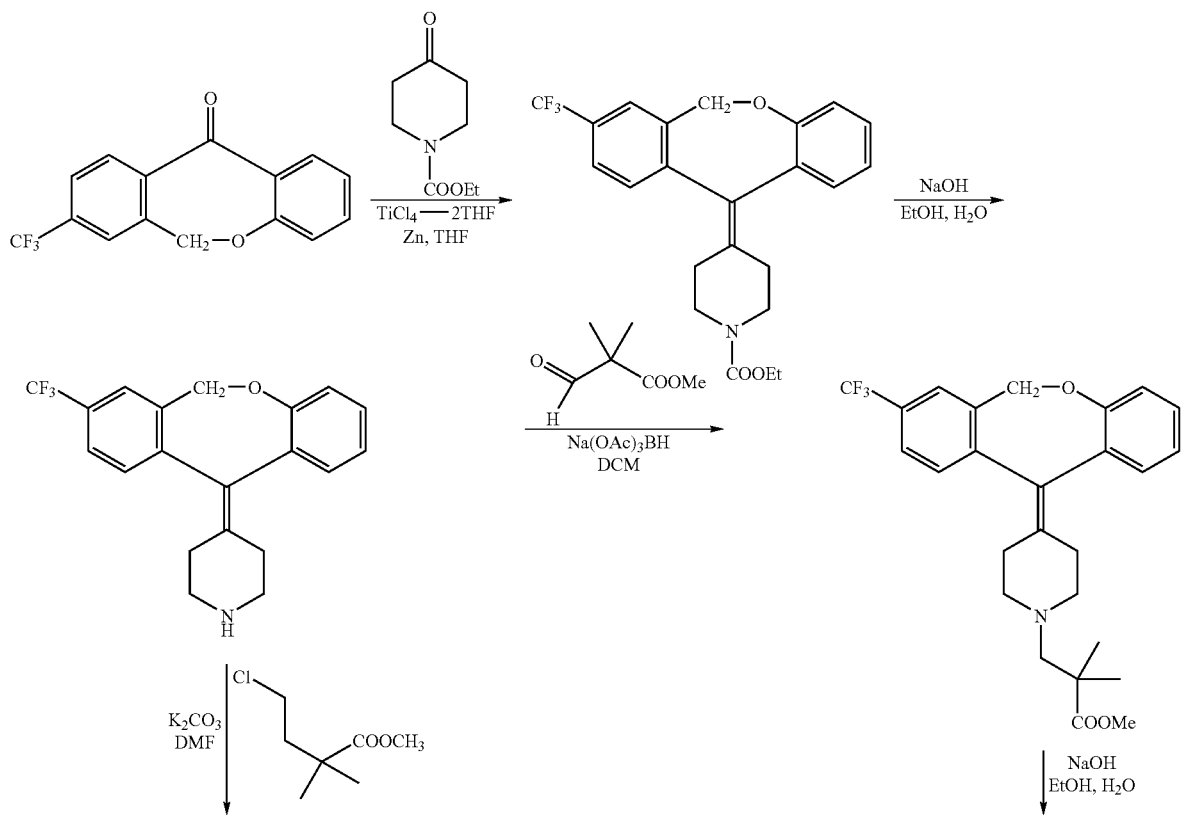

125
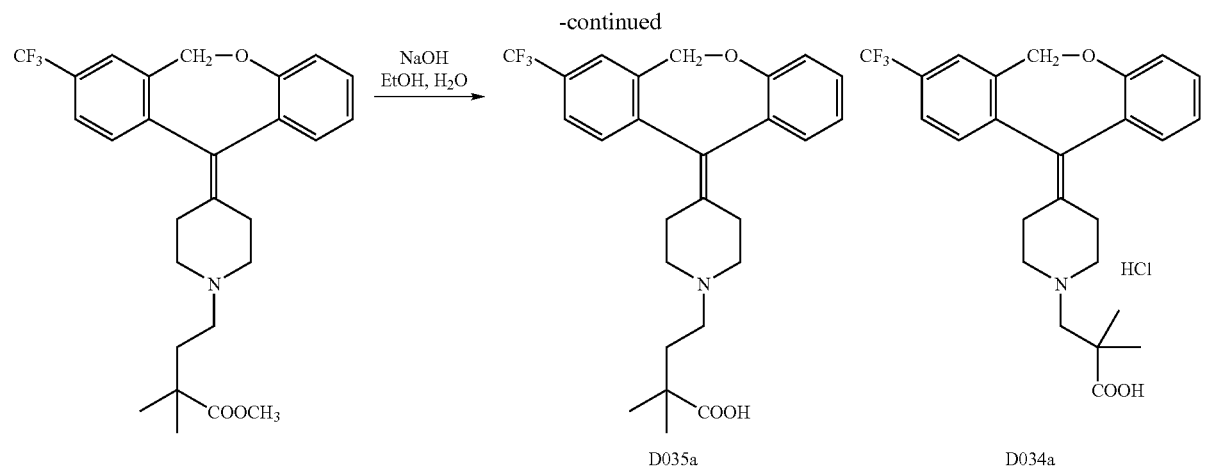
126
SCHEME 11
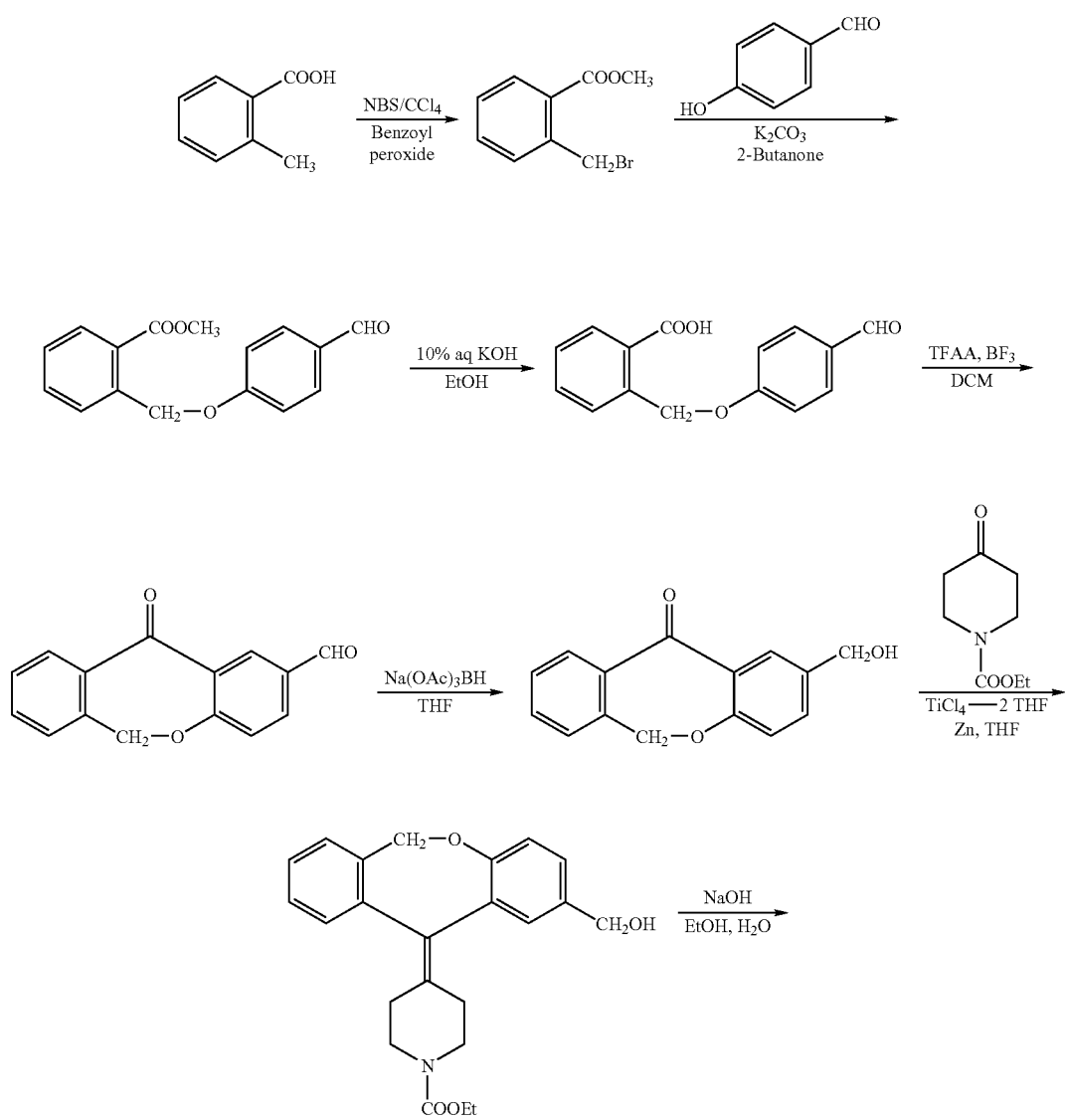

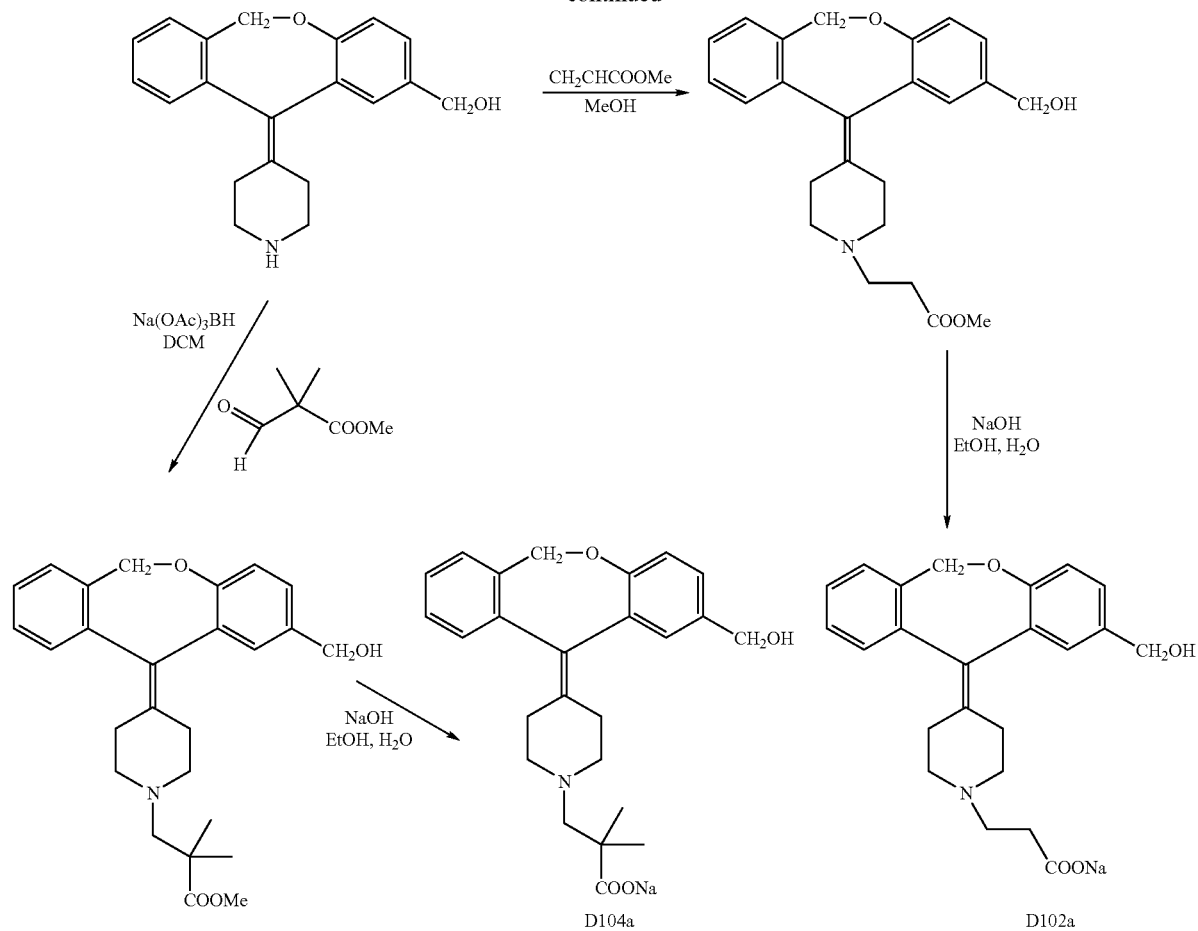
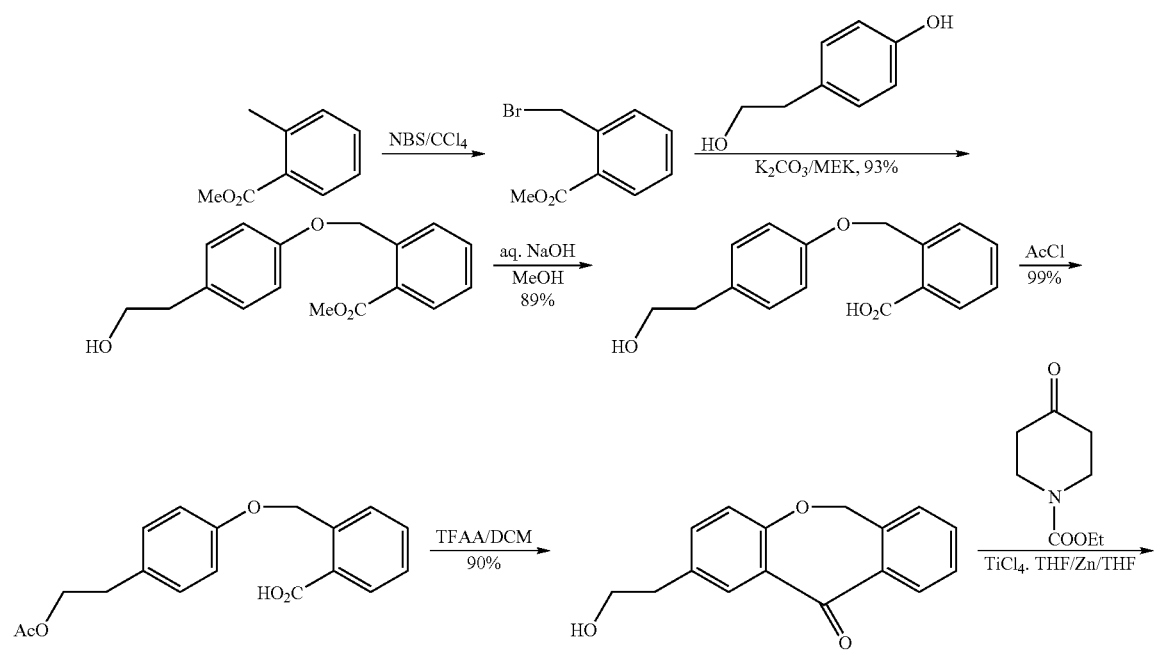
SCHEME 12

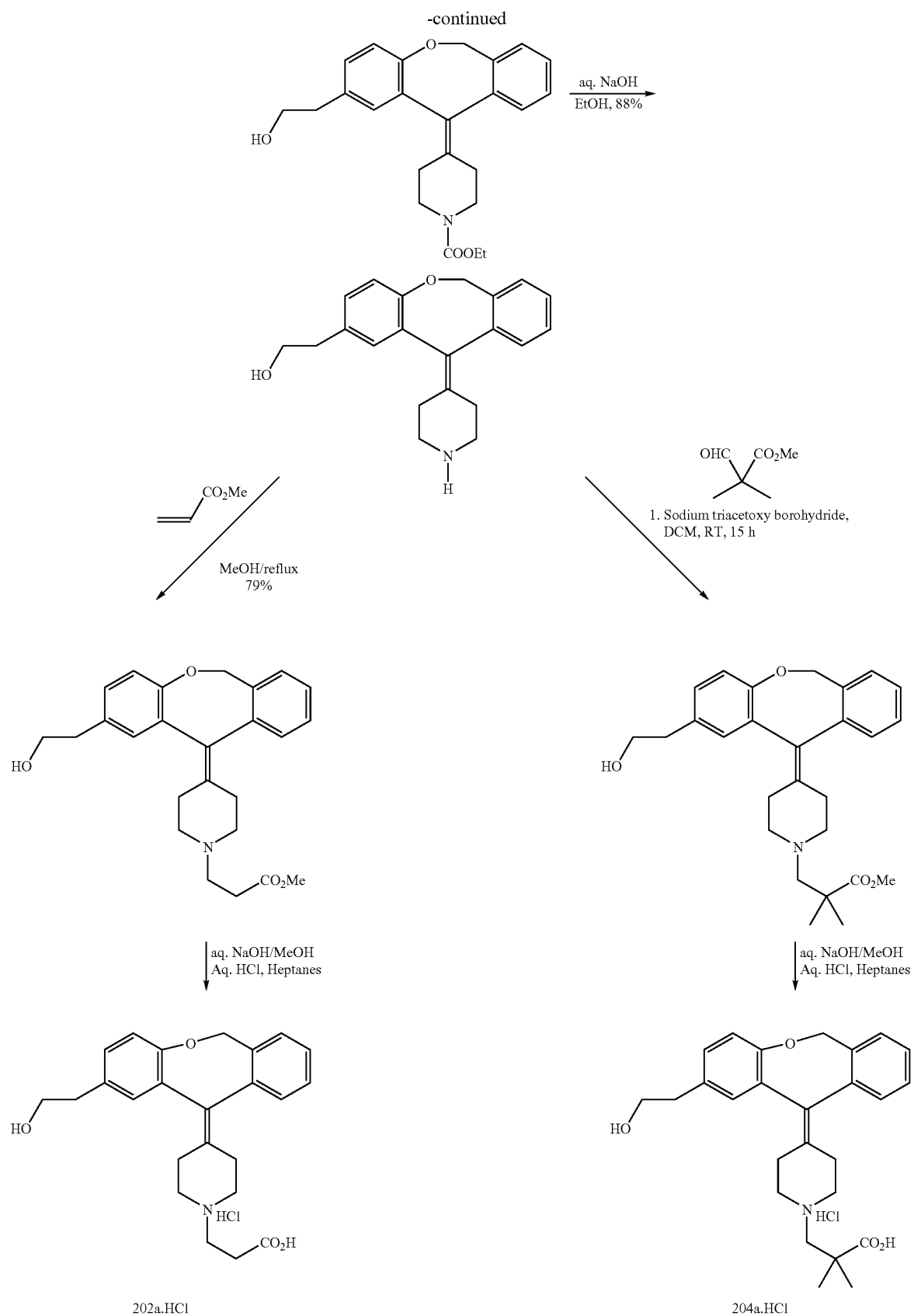

131 132
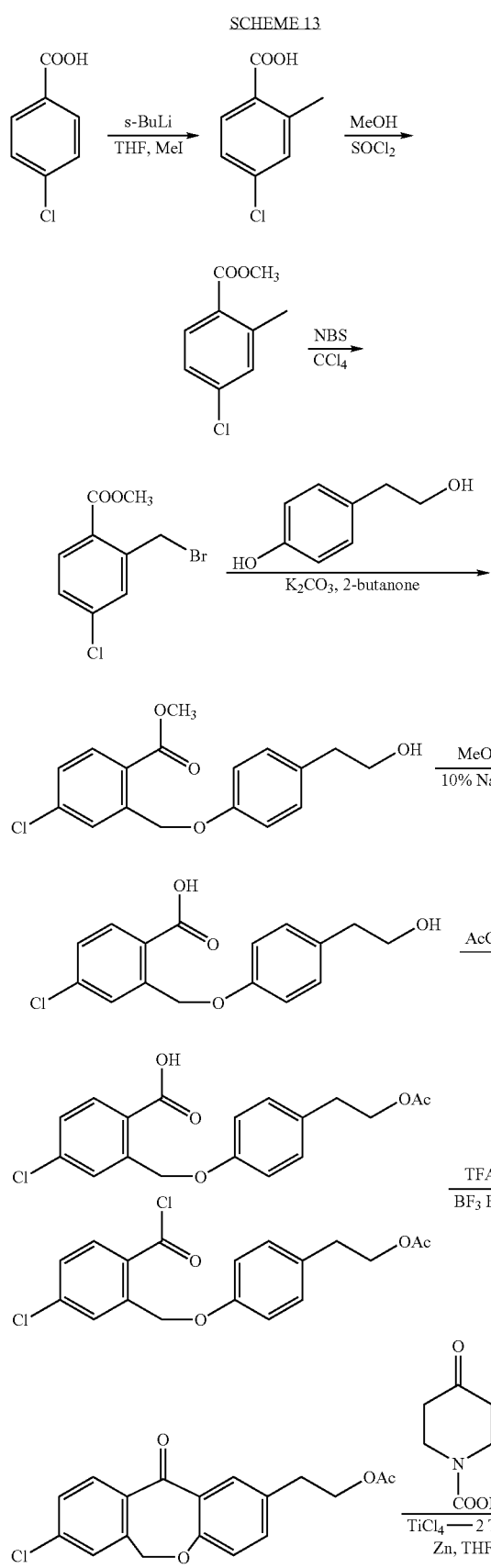
SCHEME 13
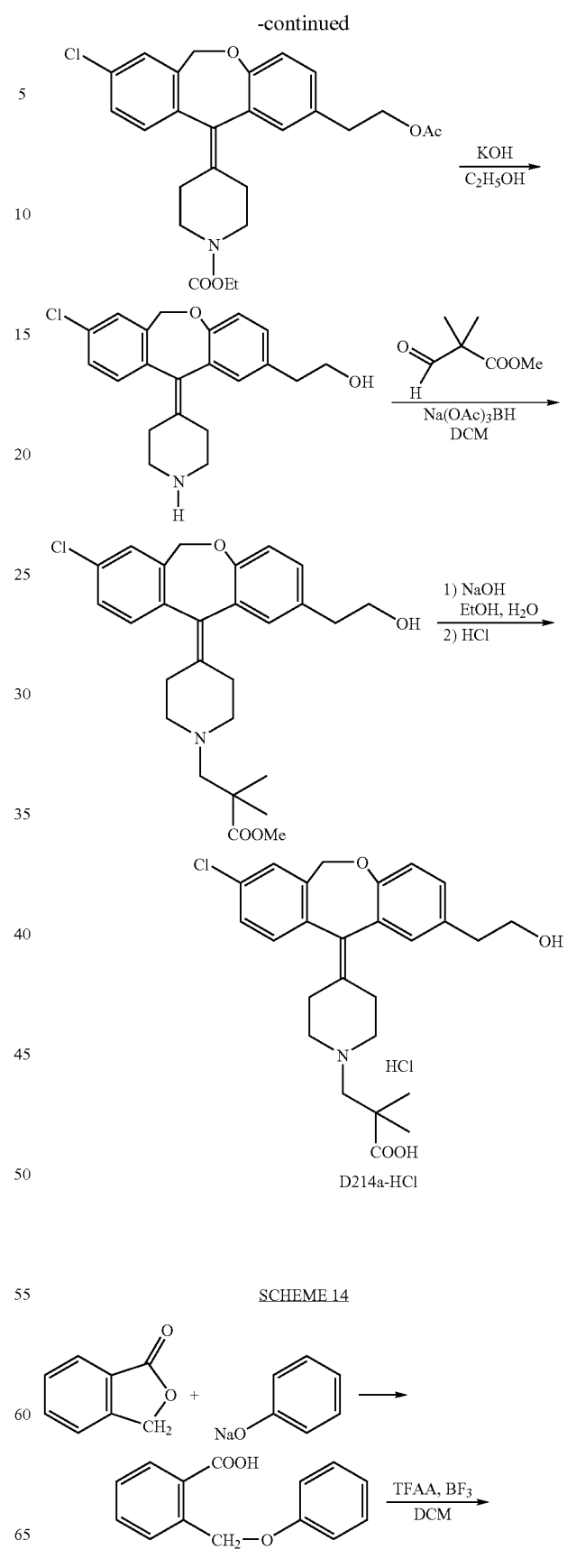
-continued
SCHEME 14

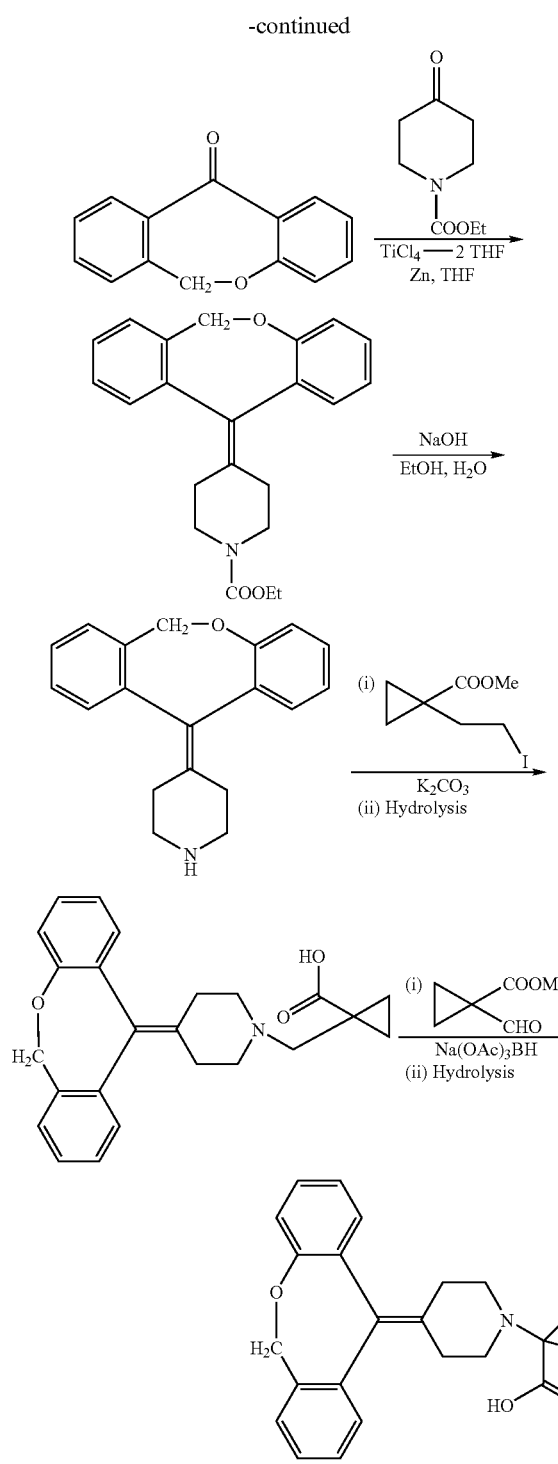
SCHEME 15
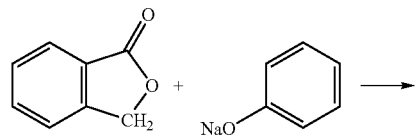
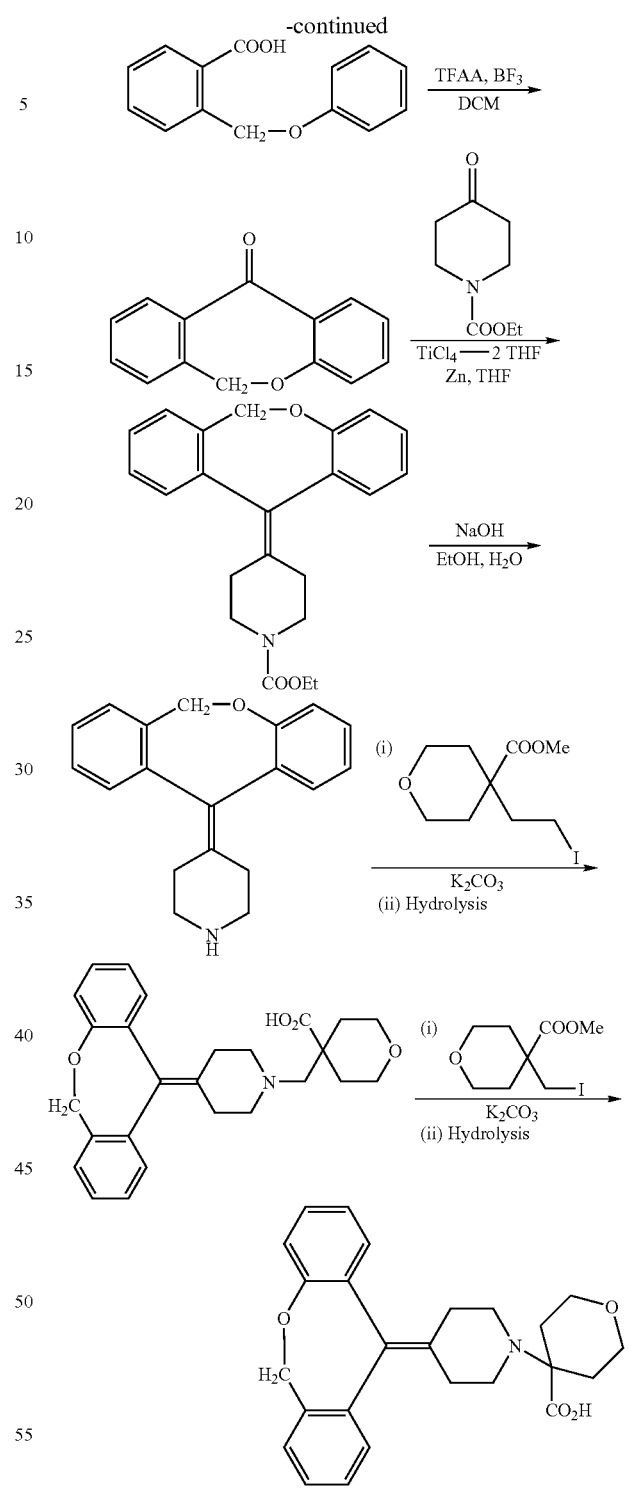
EXAMPLE 10
Sleep-wakefulness, locomotor activity and body temperature were monitored in Male Wistar rats treated with three chemical formulations, individually including three antihistamine-class compounds of the invention, 11f, 15f, and 6f. Treatments were administered at CT-18 (Circadian Time, 6 hours after lights-off) and produced robust soporific effects characterized by increased nonREM sleep time, increased sleep continuity, but without evidence of REM sleep inhibition or rebound insomnia. The general experimental conditions utillized in testing the above listed compounds of the invention are described below.

I. Animals & Surgery. Adult, male Wistar rats (250 g at time of surgery, Charles River Laboratories) were anesthetized (Nembutal, 62 mg/kg) and surgically prepared with a cranial implant to permit chronic electro-encephalogram (EEG) and electromyogram (EMG) recording. Body temperature and locomotor activity were monitored via a miniature transmitter (Minimitter) surgically placed in the abdomen. The cranial implant consisted of stainless steel screws (two frontal [+3.2 AP from bregma, ±2.0 ML] and two occipital [−6.9 AP, ±5.5 ML]) for EEG recording. Two Teflon-coated stainless steel wires were positioned under the nuchal trapezoid muscles for EMG recording. All leads were soldered to a miniature connector prior to surgery, and gas sterilized in ethylene oxide. The implant assembly was affixed to the skull with dental acrylic. A minimum of three weeks was allowed for surgical recovery.

II. Recording environment. Each rat was permanently housed in its own individual recording cage located within separate, ventilated compartments of custom-designed stainless steel cabinets. Each Nalgene microisolator cage was enhanced with a filter-top riser and low-torque swivel-commutator. Food and water were available ad libitum. A 24-hr light-dark cycle (12 hours light, 12 hours dark) was maintained throughout the study using 4-watt fluorescent bulbs 5 cm from the cage. Animals were undisturbed for at least 48 hours before and after treatments.

III. Automated physiological monitoring. Sleep and wakefulness were determined using "SCORE-2000™"—an internet-based sleep-wake and physiological monitoring system. The system monitored amplified EEG (bandpass 1–30 Hz; digitization rate 400 Hz), integrated EMG (bandpass 10–100 Hz), body temperature and non-specific locomotor activity (LMA) via telemetry, and drinking activity, continuously and simultaneously. Arousal states were classified on-line as NREM sleep, REM sleep, wake, or theta-dominated wake every 10 seconds using EEG feature extraction and pattern-matching algorithms. The classification algorithm used individually-taught EEG-arousal-state templates, plus EMG criteria to differentiate REM sleep from theta-dominated wakefulness, plus behavior-dependent contextual rules (e.g., if the animal was drinking, it is awake). Drinking and locomotor activity (LMA) were recorded as discrete events every 10 seconds, while body temperature was recorded each minute. Locomotor activity was detected by a telemetry receiver (Minimitter, Sunriver, Ore.) beneath the cage. Telemetry measures (LMA and body temperature) were not part of the scoring algorithm; thus, sleep-scoring and telemetry data were independent measures.

IV Treatments and study design.

A. Timing of treatment. Compounds were administered at CT-18, the peak of the activity-dominated period, in order to ensure (i) prior wakefulness was sufficient to interact positively with hypnotic-drug effects, and (ii) sufficient time was allowed to view the time course of the treatment effect before lights-on (6 hours post-treatment).

B. Vehicle and route of administration. Compounds were suspended in sterile 0.25% or 0.5% methylcellulose (2 ml/kg). Treatments were administered as an intraperitoneal bolus.

C. Study design and controls. A parallel group study design was employed. Vehicle controls were drawn from a large pool (N>200): a subset of the pooled vehicle controls was selected, based on computerized matching with the 24-hour pre-treatment baseline of the active treatment group.

D. Drugs tested. Three (3) antihistaminergic novel chemical compounds of the current invention were tested for this proof of principle study, 11$f$ (30 and 10 mg/kg), and 6$f$ (30 mg/kg) and 15$f$ (30 mg/kg).

Results of Compounds Tested

Figure 1B:
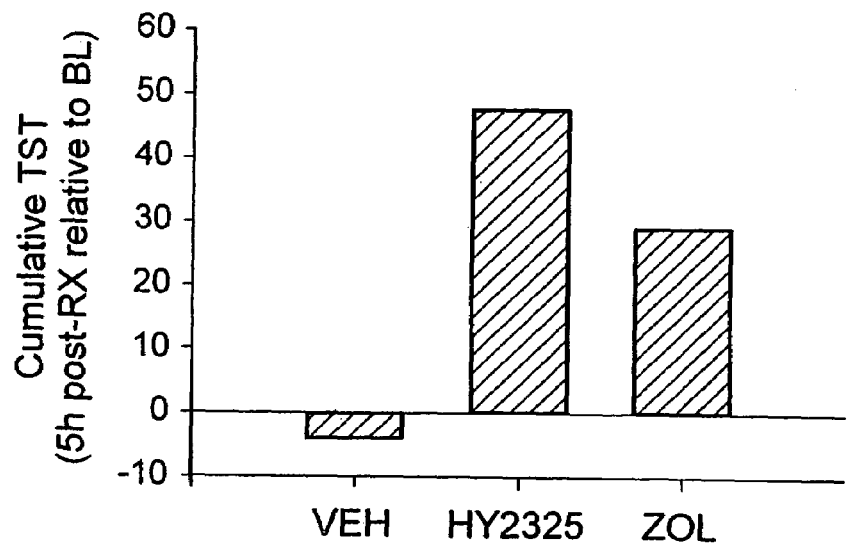
Figure 1C:
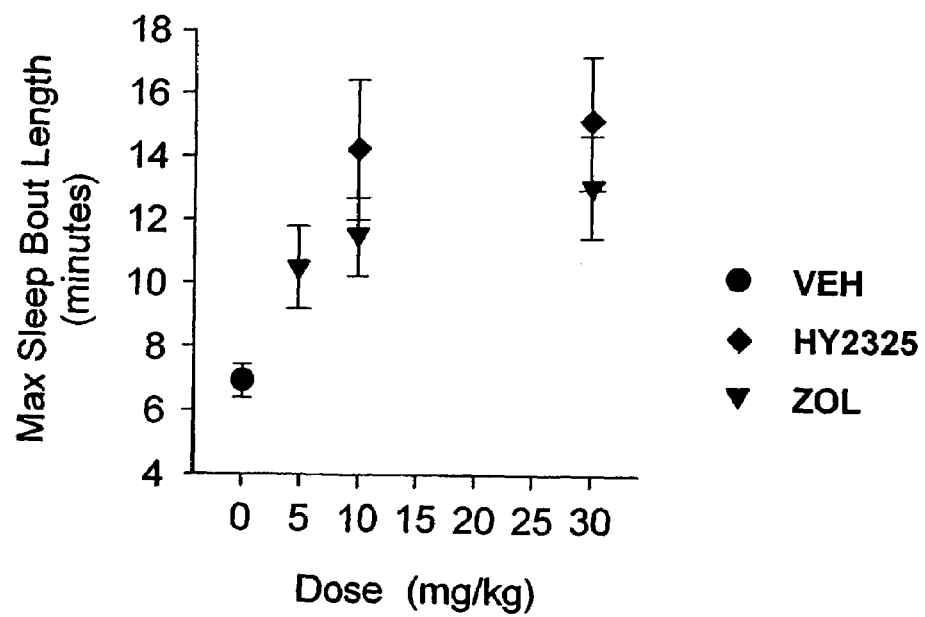

11$f$ significantly increased total sleep time for 3 hours post-treatment after both 30 mg/kg and 10 mg/kg treatments (N=11 and 9, respectively, where N is the number of animals per dose group), and increased sleep continuity, as assessed by sleep bout length. The effect on maximum sleep bout length (a measure of sleep continuity) during the initial 5 hours post-treatment sleep bout versus dose is shown in FIG. 1($c$). 11$f$ increased sleep continuity at both 10 and 30 mg/kg doses relative to vehicle control. The treatment effects of Zolpidem are also shown for comparison.

A concomitant reduction in locomotor activity paralleled the sleep inducing effects of 11$f$. These effects were prototypical for sedative-hypnotic/soporific agents and compared equal or better to therapeutic doses of the sedative hypnotic market leader—Ambien® (Zolpidem). 11$f$ did not, however, produce REM sleep inhibition or rebound insomnia at 10 mg/kg or 30 mg/kg in male Wistar rats. REM sleep inhibition and rebound insomnia are undesirable side effects commonly observed in currently marketed prescription sedative hypnotics. A comparison of the total sleep time resulting from 11$f$ (30 mg/kg), the sedative hypnotic positive control standard (Zolpidem, 10 mg/kg), and the vehicle control as a function of time from the administration of the dose is depicted as a time series plot in FIG. 1($a$). The time series plot shows the sleep patterns before and after treatment, wherein the arrow indicates the primary soporific effect of 11$f$.

The cumulative effect on total sleep time (TST) during the initial 5 hours post-treatment, relative to baseline (BL), for 11$f$ (HY2325), Zolpidem, and the vehicle control is shown in FIG. 1($b$). It is apparent that 11$f$ (30 mg/kg) induced more TST than Zolpidem (10 mg/kg).

6$f$ (N=5) and 15$f$ (N=5), compounds of the invention related to HY2325-01, also produced an increase in non-REM sleep time for 2–3 hours post-treatment relative to the vehicle control animals. In addition, 6$f$ and 15$f$ did not produce REM sleep inhibition or rebound insomnia under the conditions studied.

11$f$, 6$f$ and 15$f$, are representative novel antihistaminergic soporific chemical compounds of the invention. 11$f$ increased sleep, e.g., sleep time and sleep continuity (sleep bout lengths), in laboratory rats in a dose-dependent fashion. Single doses of 6$f$ and 15$f$ also increased sleep in laboratory rats.

Additional compounds of the invention were tested using the above methodology, and the results are shown below in Table 4.

TABLE 4

| Compound (at CT-18) | Dose (mg/kg) | Onset (minutes) | Duration (hrs) | Average Bout-Length (minutes) | Maximum Bout Length (minutes) | NREM Peak (%/hr) | NREM Accum. (minutes) | Rebound Insomnia | Motor Inhibition | REM Inhibition |
|---|---|---|---|---|---|---|---|---|---|---|
| Ambien (Zolpidem) | 30 IP | 5 | 3–4 | 5.8 | 13.1 | 58.2 | 58.7 | YES | YES | YES |
| Doxepin-like | 30 PO | 90 | 4–5 | 11 | 25.1 | 72.0 | 44.8 | NO | NO | YES |
| (8a) | 30 PO | 65 | 5–6 | 12.2 | 28.9 | 75.5 | 65.8 | NO | NO | NO |
| (73a) | 30 PO | 45 | 5–6+ | 14.5 | 27.6 | 62.2 | 47.3 | NO | NO | NO |
| (74a) | 30 PO | 70–80 | 5–6 | 9.9 | 22.3 | 64.4 | 43.4 | NO | NO | NO |
| (75a) | 30 PO | 70–85 | 4 | 6.8 | 13.6 | 58.8 | 33.9 | NO | NO | NO |
| (75a) | 45 PO | 70–85 | 5 | 10.8 | 19.4 | 58.2 | 33.9 | NO | NO | NO |
| (7a) | 30 PO | 130 | 5–6 | 7.3 | 16.9 | 56.9 | 29.5 | NO | NO | NO |
| (7d) | 30 PO | 85 | 5 | 12.9 | 25.0 | 76.9 | 54.1 | NO | NO | NO |
| Pheniramine-like | | | | | | | | | | |
| (11a) | 30 PO | 85 | 6 | 11.2 | 18.7 | 67.3 | 41.2 | Minor | NO | NO |
| (11d) | 30 PO | 135 | 6 | 11.0 | 20.1 | 58.5 | 55.5 | NO | NO | NO |
| (11e) | 30 PO | 80 | 6 | 8.3 | 19.1 | 59.6 | 49.6 | NO | NO | NO |
| Diphenhydramine-like | | | | | | | | | | |
| (53a) | 30 PO | 30 | 4 | 4.3 | 9.1 | 49.2 | 17.4 | NO | NO | NO |
| (6a) | 30 PO | 65 | 5 | 7.0 | 12.8 | 56.4 | 26.5 | NO | NO | NO |
| Triprolidine-like | | | | | | | | | | |
| (16a) | 30 PO | 180 | 5 | 5.4 | 11.8 | 57.9 | 20.7 | NO | NO | NO |

Note:
PO is oral administration and IP is intraperitoneal administration.

EXAMPLE 11

H1 Binding Assay for Series 11 Compounds

I. Introduction

The following binding assays were performed on the Series 11 compounds described above by displacement of known standards from the H1, M1, M2, and M3 receptors, wherein H1 is a histamine receptor, and M1, M2, and M3 are muscarinic receptors.

The binding studies against the histamine receptor, H1, indicate binding affinity, and therefore the results of the binding assays are an indication of the activity of the compound.

In addition, the binding studies against the muscarinic receptors indicate the extent to which the compounds bind the muscarinic receptors, responsible for anti-cholinergic activity of the compound. Binding to muscarinic receptors results in several undesired side effects of many known antihistamines, e.g., dry-mouth. A decrease in the binding of the compounds to the M1–3 receptors, relative the binding of the compound to the H1 receptor, is an indication of the greater specificity of the compound for the histamine receptor over the muscarinic receptor. Moreover, a drug with increased specificity for the histamine receptor would possess less anti-cholinergic side effects.

Figures 2A, 2B:
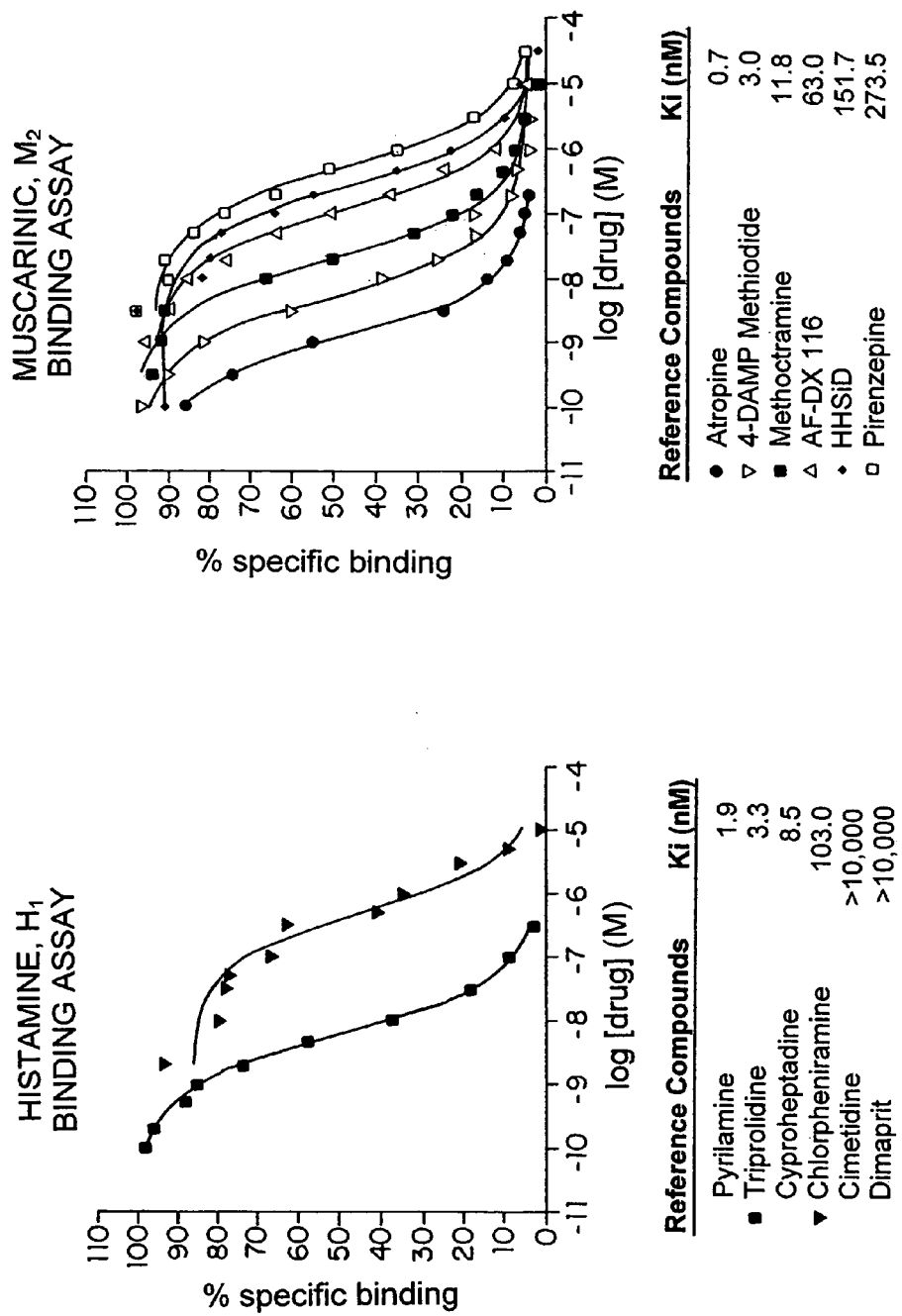
FIGS. 2A–G are graphs depicting the binding of reference compounds to the receptors as indicated.

FIG. 2A depicts a graph of binding of the reference compounds to the receptor.

| Assay Characteristics: | |
|---|---|
| $K_D$ (binding affinity): | 1.3 nM |
| $B_{max}$ (receptor number): | 6.2 fmol/mg tissue (wet weight) |
| Materials and Methods: | |
| Receptor Resource: | Bovine cerebellar membranes |
| Radioligand: | [$^3$H]Pyrilamine (15–25 Ci/mmol) |
| | Final ligand concentration - [2.0 nM] |
| Non-specific Determinant: | Triprolidine - [10 μM] |
| Reference Compound: | Triprolidine |
| Positive Control: | Triprolidine |
| Incubation Conditions: | Reactions are carried out in 50 mM Na—KPO$_4$ (pH 7.5) at 25° C. for 60 minutes. The reaction is terminated by rapid vacuum filtration onto glass fiber filters. Radioactivity trapped onto the filters is determined and compared to control values in order to ascertain any interactions of test compound with the histamine$_1$ binding site. |
| Literature Reference: | Chang, et al. Heterogeneity of Histamine H$_1$-Receptors: Species Variations in [$^3$H]Mepyramine Binding of Brain Membranes. Journal of Neurochemistry. 32: 1653–1663 (1979) with modifications. |
| | Martinez-Mir, M. I., Pollard, H., Moreau, J., et al. Three Histamine Receptors (H$_1$, H$_2$, and H$_3$) Visualized in the Brain of Human and Non-Human Primates. Brain Res. 526: 322–327 (1990). |
| | Haaksma. E. E. J., Leurs, R. and Timmerman, H. Histamine Receptors: Subclasses and Specific Ligands. Pharmac. Ther. 47: 73–104 (1990). |

Figures 2C, 2D:
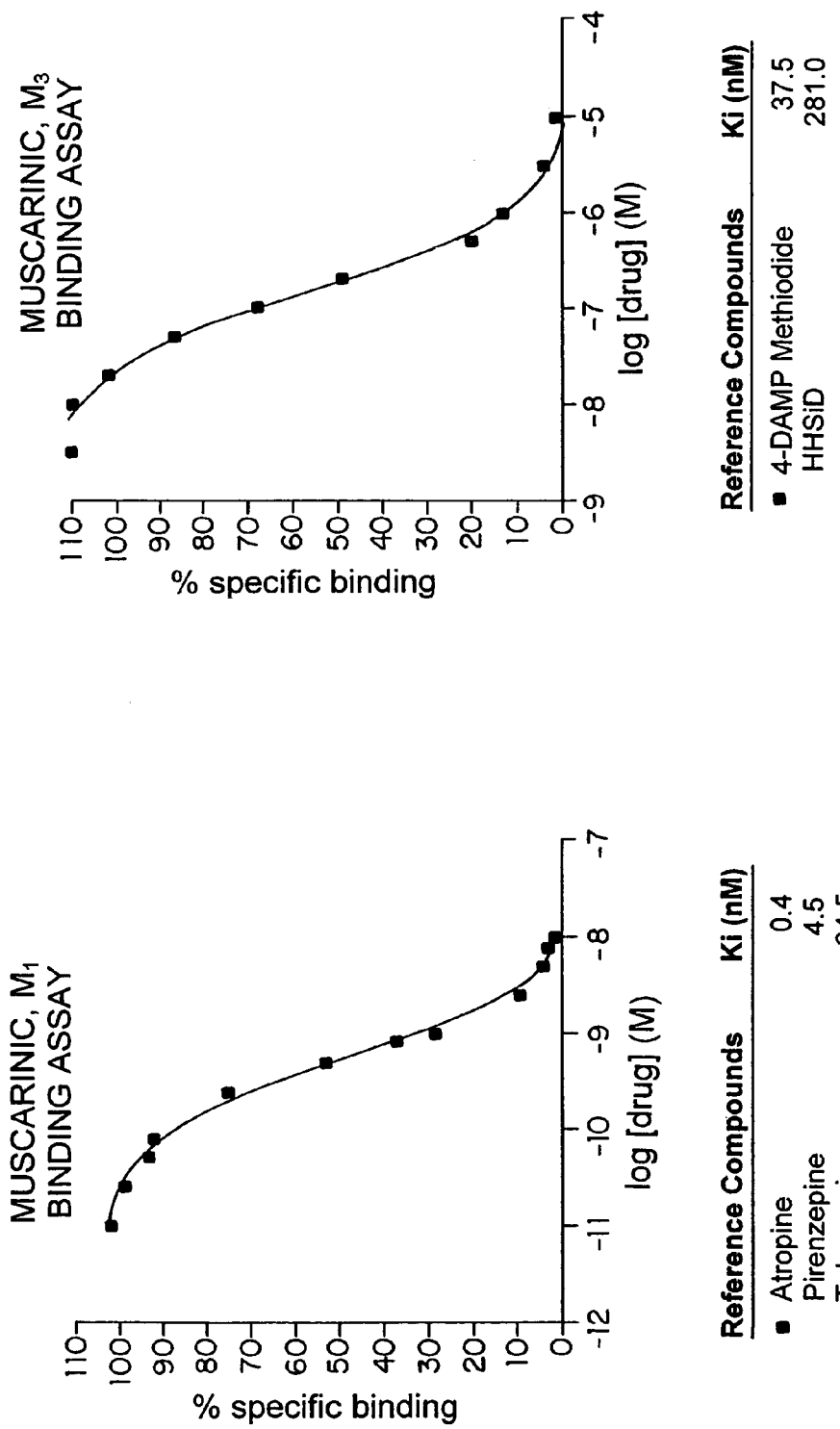
Figure 2F:
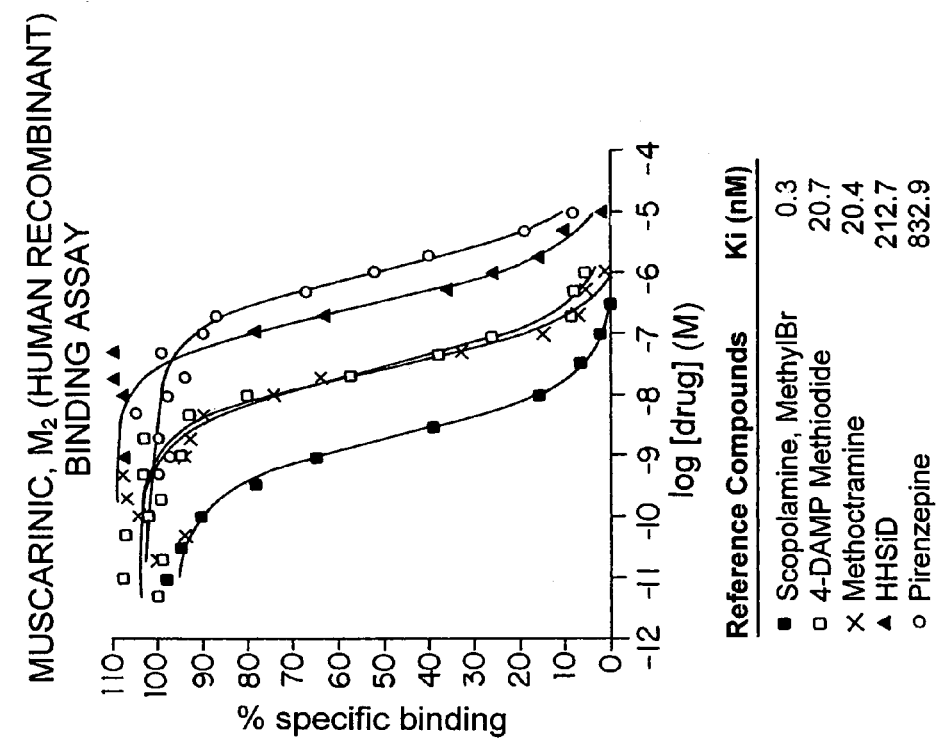
Figure 2E:
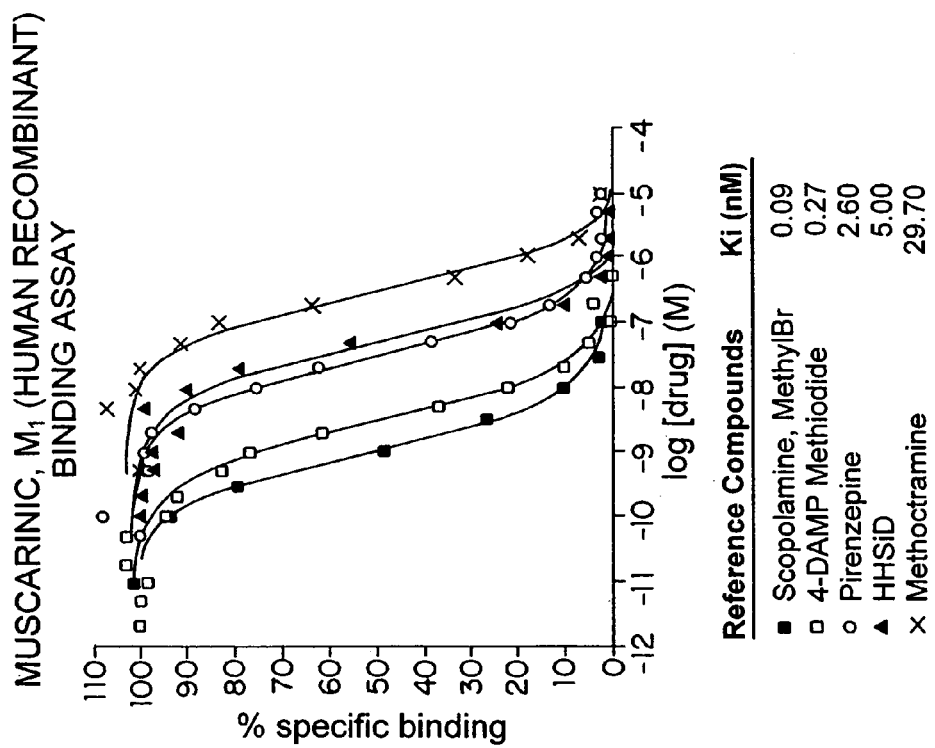

FIG. 2E depicts a graph of binding of the reference compounds to the receptor.

Assay Characteristics:

| | |
|---|---|
| $K_D$ (binding affinity): | 0.05 nM |
| $B_{max}$ (receptor number): | 4.2 pmol/mg protein |
| Materials and Methods: | |
| Receptor Source: | Human recombinant expressed in CHO cells |
| Radioligand: | [$^3$H]-Scopolamine, N-Methyl Chloride (80–100 Ci/mmol) |
| | Final ligand concentration - [0.5 nM] |
| Non-specific Determinant: | (−)-Scopolamine, Methyl-, bromide Methylscopolamine bromide) - [1.0 µM] |
| Reference Compound: | (−)-Scopolamine, Methyl-, bromide (Methylscopolamine bromide) |
| Positive Control: | (−)-Scopolamine, Methyl-, bromide (Methylscopolamine bromide) |
| Incubation Conditions: | Reactions are carried out in 50 mM TRIS-HCl (pH 7.4) containing 10 mM MgCl$_2$, 1 mM EDTA for 60 minutes at 25° C. The reaction is terminated by rapid vacuum filtration onto glass fiber filters. Radioactivity trapped onto the filters is determined and compared to control values in order to ascertain any interactions of test compound(s) with the cloned muscarinic-M$_1$ binding site. |
| Literature Reference: | Buckley, N. J., Bonner, T. I., Buckley, C. M., and Brann, M. R. Antagonist Binding Properties of Five Cloned Muscarinic Receptors Expressed in CHO-K1 Cells. Mol. Pharmacol. 35: 469–476 (1989) with modifications. |

FIG. 2C depicts a graph of binding of the reference compounds to the receptor.

Assay Characteristics:

| | |
|---|---|
| $K_d$ (binding affinity): | 2.2 nM |
| $B_{max}$ (receptor number): | 1.4 pmol/mg protein |
| Materials and Methods: | |
| Receptor Source: | Bovine striatal membranes |
| Radioligand: | [$^3$H]Pirenzepine (70–87 Ci/mmol) |
| | Final ligand concentration - [1.0 nM] |
| Non-specific Determinant: | Atropine sulfate - [0.1 µM] |
| Reference Compound: | Atropine sulfate |
| Positive Control: | Atropine sulfate |
| Incubation Conditions: | Reactions are carried out in 25 mM HEPES (pH 7.4) at 25° C. for 60 minutes. The reaction is terminated by rapid vacuum filtration onto glass fiber filters. Radioactivity trapped onto the filters is determined and compared to control values in order to ascertain any interactions of test compound with the muscarinic, binding site. |
| Literature Reference: | Watson, M., Yamamura, H. I., and Roeske, W. A Unique Regulatory Profile and Regional Distribution of [$^3$H]Pirenzepine Binding in the Rat Provide Evidence for Distinct M$_1$ and M$_2$ Muscarinic Receptor Subtypes. Life Sciences. 32: 3001–3011 (1983) with modifications. |
| | Luthin, G. R. and Wolfe, B. B. [$^3$H]Pirenzepine and [$^3$H]QNB Binding to Brain Muscarinic Cholinergic Receptors. Molec. Pharmac. 26: 164–169 (1984). |

FIG. 2F depicts a graph of binding of the reference compounds to the receptor.

Assay Characteristics:

| | |
|---|---|
| $K_D$ (binding affinity): | 0.29 nM |
| $B_{max}$ (receptor number): | 2.1 pmol/mg protein |
| Materials and Methods: | |
| Receptor Source: | Human recombinant expressed in CHO cells |
| Radioligand: | [$^3$H]-Scopolamine, N-Methyl Chloride (80–100 Ci/mmol) |
| | Final ligand concentration - [0.5 nM] |

-continued

| | |
|---|---|
| Non-specific Determinant: | Methylscopolamine bromide - [1.0 µM] |
| Reference Compound: | (−)-Scopolamine, Methyl-, bromide (Methylscopolamine bromide) |
| Positive Control: | (−)-Scopolamine, Methyl-, bromide (Methylscopolamine bromide) |
| Incubation Conditions: | Reactions are carried out in 50 mM TRIS-HCl (pH-7.4) containing 10 mM $MgCl_2$, 1 mM EDTA for 60 minutes at 25° C. The reaction is terminated by rapid vacuum filtration onto glass fiber filters. Radioactivity trapped onto the filters is determined and compared to control values in order to ascertain any interactions of test compound(s) with the cloned muscarinic - $M_2$ binding site. |
| Literature Reference: | Buckley, N. J., Bonner, T. I., Buckley, C. M. and Brann, M. R. Antagonist Binding Properties of Five Cloned Muscarinic Receptors Expressed in CHO-K1 Cells. Mol. Pharmacol 35: 469–476 (1989) with modifications. |

FIG. 2B depicts a graph of binding of the reference compounds to the receptor.

Assay Characteristics:

| | |
|---|---|
| $K_d$ (binding affinity): | 6.4 nM |
| $B_{max}$ (receptor number): | 2.1 pmol/mg protein |

Materials and Methods:

| | |
|---|---|
| Receptor Source: | Rat cardiac membranes |
| Radioligand: | [$^3$H]AF-DX 384 (70–120 Ci/mmol) Final ligand concentration - [3.0 nM] |
| Non-specific Determinant: | Methoctramine - [10 µM] |
| Reference Compound: | Methoctramine |
| Positive Control: | Methoctramine |
| Incubation Conditions: | Reactions are carried out in 10 mM Na—$KPO_4$ (pH 7.4) at 25° C. for 60 minutes. The reaction is terminated by rapid vacuum filtration onto glass fiber filters. Radioactivity trapped onto the filters is determined and compared to control values in order to ascertain any interactions of test compound with the muscarinic$_2$ binding site. |
| Literature Reference: | Hammer, R., Giraldo, E. et al. Binding Profile of a Novel Cardioselective Muscarine Receptor Antagonist, AF-DX 116, to Membranes of Peripheral Tissues and Brain in the Rat. Life Sciences. 38: 1653–1662 (1986) with modifications. Wang, J. X., Roeske, W. R. et al. [$^3$H]AF-DX 116 Labels Subsets of Muscarinic Cholinergic Receptors in Rat Brain and Heart. Life Sciences. 41: 1751–1760 (1987). Elberlein, W. G., et al. Supplement: Subtypes Muscarinic Receptors IV. TIPS. 50 (1989). |

FIG. 2D depicts a graph of binding of the reference compounds to the receptor.

Assay Characteristics:

| | |
|---|---|
| $K_d$ (binding affinity): | 1.4 nM |
| $B_{max}$ (receptor number): | 7.7 fmol/mg protein |

Materials and Methods:

| | |
|---|---|
| Receptor Source: | Guinea pig ileum membranes |
| Radioligand: | [3H]Scopolamine, N-Methyl (70–87 Ci/mmol) Final ligand concentration - [1.0 nM] |
| Non-specific Determinant: | 4-DAMP Methiodide - [10 uM] |
| Reference Compound: | 4-DAMP methiodide |
| Positive Control: | 4-DAMP methiodide |
| Incubation Conditions: | Reactions are carried out in 30 mM HEPES (pH 7.4) containing 142 mM NaCl, 5.6 mM KCl, 2.2 mM $CaCl_2$, 3.6 mM $Na_2CO_3$, 1 mM $MgCl_2$ and 5.6 mM glucose al 37° C. for 2 hours. The reaction is terminated by rapid vacuum filtration onto glass fiber filters. Radioactivity trapped onto the filters is determined and compared to control values in order to ascertain any interactions of test compound with the muscarinic$_3$ binding site. |

| | |
|---|---|
| -continued | |
| Literature Reference: | Hanack, C., and Pfeiffer, A. Upper Gastrointestinal Porcine Smooth Muscle Expresses $M_2$ and $M_3$ Receptors. Digestion. 45: 196–201 (1990) with modifications. Vanderheyden, P., Gies, J–P., et al. Human $M_1$, $M_2$, and $M_3$ Muscarinic Cholinergic Receptors: Binding Characteristics of Agonists and Antagonists. Jrnl. Neurolog. Sci. 97: 67-80 (1990). Smith, T. D., Annis, S. J., et al. N-[$^3$H]Methylscopolamine Labeling of Non-$M_1$, Non-$M_2$ Muscarinic Receptor Binding Sites in Rat Brain. Jrnl. Pharmacol. Exp. Ther. 256(3): 1173–1181 (1990). |

Figure 2G:
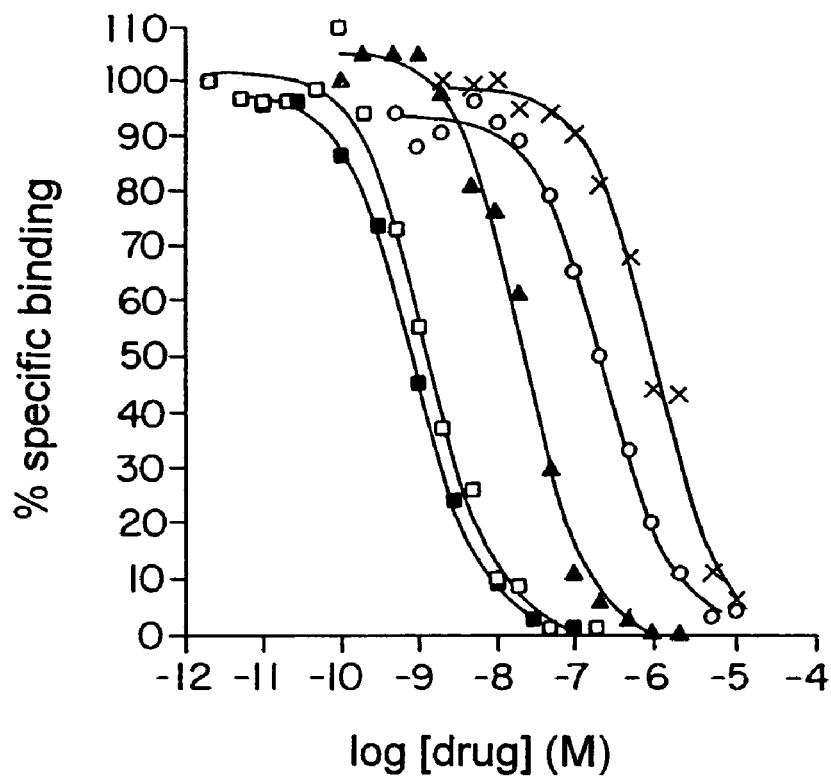

FIG. 2G depicts a graph of binding of the reference compounds to the receptor.

| | |
|---|---|
| Assay Characteristics: | |
| $K_D$ (binding affinity): | 0.14 nM |
| $B_{max}$ (receptor number): | 4.0 pmol/mg protein |
| Materials and Methods: | |
| Receptor Source: | Human recombinant expressed in CHO cells |
| Radioligand: | [$^3$H]-Scopolamine, N-Methyl Chloride (80–100 Ci/mmol) Final ligand concentration - [0.2 nM] |
| Non-specific Determinant: | (−)-Scopolamine, Methyl-, bromide (Methylscopolamine bromide) - [1.0 μM] |
| Reference Compound: | (−)-Scopolamine, Methyl-, bromide (Methylscopolamine bromide) |
| Positive Control: | (−)-Scopolamine, Methyl-, bromide (Methylscopolamine bromide) |
| Incubation Conditions: | Reactions are carried out in 50 mM TRIS-HCl (pH 7.4) containing 10 mM $MgCl_2$, 1 mM EDTA for 60 minutes at 25° C. The reaction is terminated by rapid vacuum filtration onto glass fiber filters. Radioactivity trapped onto the filters is determined and compared to control values in order to ascertain any interactions of test compound(s) with the cloned muscarnic - $M_3$ binding site. |
| Literature Reference: | Buckley, N. J., Bonner, T. I., Buckley, C. M., and Brann, M. R. Antagonist Binding Properties of Five Cloned Muscarinic Receptors Expressed in CHO-K1 Cells. Mol. Pharmacol. 35: 469–476 (1989) with modifications. |

III. Results

The data in Table 5 show the results of the assays, described above, performed on the Series 11 compounds, as indicated.

to the presence of the oxygen. Alternatively, the presence of the oxygen may lend itself to alteration of the physical properties of the molecule in other ways, e.g., the electronic properties help to control ester cleavage, or the presence of the oxygen adds to receptor affinity through increased binding interactions with the receptor.

TABLE 5

| | | H1 | | M1 | | M2 | | M3 | |
|---|---|---|---|---|---|---|---|---|---|
| Compound number | | IC50 | Ki | IC50 | Ki | IC50 | Ki | IC50 | Ki |
| Acid | 11a | 3.08E−7 | 1.19E−7 | >1.0E−5 | >1.0E−5 | >1.0E−5 | >1.0E−5 | >1.0E−5 | >1.0E−5 |
| Isopropyl | 11d | 3.78E−7 | 1.47E−7 | 8.00E−6 | 6.96E−7 | 8.29E−7 | 2.70E−7 | 6.08E−6 | 2.70E−6 |
| Isobutyl | 11e | 7.18E−7 | 2.79E−7 | 3.76E−6 | 2.89E−7 | 3.55−E6 | 1.15E−6 | 2.59E−6 | 7.10E−7 |
| Cyclopentyl | 11f | 1.07E−6 | 4.16E−7 | 2.21E−6 | 1.70E−7 | — | — | — | — |
| S-THF | 11g | 1.96E−7 | 8.61E−8 | 4.68E−6 | 3.60E−7 | 5.70E−6 | 2.08E−6 | 5.71E−6 | 1.56E−6 |
| R-THF | 11h | 2.01E−7 | 8.83E−8 | 2.24E−6 | 1.72E−7 | 2.14−E6 | 6.97E−7 | 2.20E−6 | 6.03E−7 |
| THP | 11i | 2.00E−7 | 8.78E−8 | 2.21E−7 | 1.70E−8 | 2.21E−7 | 7.20E−8 | 2.33E−6 | 1.03E−6 |

IV Conclusions

A. An interesting trend that is exhibited by the data in Table 4, shows that the tetrahydrofuran and tetrahydropyran esters appear to show a greater affinity for the H1 receptor than the non-oxygen substituted esters.

This increased affinity may be an indication of increased water solubility or that the altered ring conformation may have any affect on the steric properties at the carbonyl of the ester, e.g., a beneficial change in the ring conformation due B. In addition the data indicates that the compounds have greater affinity for the H1 receptors as compared with the M1, M2, and M3 receptors, which as described above, indicates that these drugs should result in the reduction of anti-cholinergic side effects.

C. Table 4 also indicates that the binding data for the enantiomeric compounds, 11 h and 11 g, do not result in a substantial difference in binding affinity towards the H1 receptor, but do show a substantial difference in binding affinity towards the muscarinic receptors. This indicates that the muscarinic receptors may have a stereochemical preference, and therefore the selectivity of the receptor may be used to assist in the selection of a therapeutic compound that would provide reduced side effects.

D. In addition, it can be seen in from the data in Table 4 that the corresponding acid of the therapeutic ester compound loses detectable affinity for the muscarinic receptors. This property, as describe above, can be used to reduce anti-cholinergic side-effects of the therapeutic compound.

EXAMPLE 12

H1 Binding Assays for Additional Compound Series

I. Introduction

The following binding assays were performed on additional compounds described above by displacement of known standards from the H1, M1, M2, and M3 receptors, wherein H1 is a histamine receptor, and M1, M2, and M3 are muscarinic receptors.

The binding studies against the histamine receptor, H1, indicate binding affinity, and therefore the results of the binding assays are an indication of the activity of the compound.

In addition, the binding studies against the muscarinic receptors indicate the extent to which the compounds bind the muscarinic receptors, responsible for anti-cholinergic activity of the compound. Binding to muscarinic receptors results in several undesired side effects of many known antihistamines, e.g., dry-mouth. A decrease in the binding of the compounds to the M1–3 receptors, relative the binding of the compound to the H1 receptor, is an indication of the greater specificity of the compound for the histamine receptor over the muscarinic receptor. Moreover, a drug with increased specificity for the histamine receptor would possess less anti-cholinergic side effects.

II. Binding Assays

The binding assays for H1 was the same as described in Example 10 and the M1, M2, and M3 binding assays are the same as those described in Example 10 for human recombinant expressed cells.

III. Results

The data in Table 6 show the results of the assays, described above, performed on various compounds of the invention, as indicated.

TABLE 6

$H_1$ Antagonist Series
Receptor Binding Data ($K_i$ nM)

| | $H_1$ | $M_1$ | $M_2$ | $M_3$ |
|---|---|---|---|---|
| Doxepin-like | | | | |
| (8a) | 62.5 | >10,000 | >10,000 | >10,000 |
| (73a) | 42.8 | >10,000 | >10,000 | >10,000 |
| (74a) | 109 | >10,000 | >10,000 | >10,000 |
| (75a) | 47.9 | >10,000 | 3,331 | >10,000 |
| (7a) | 55.1 | >10,000 | >10,000 | >10,000 |
| (dox7d-oxalate) | 198 | >10,000 | >10,000 | >10,000 |
| Diphenhydramine-like | | | | |
| (53a) | 16.1 | >10,000 | >10,000 | >10,000 |
| (6a) | 56.1 | >10,000 | >10,000 | 8,900 |
| Triprolidine-like | | | | |
| (16a) | 43.9 | >10,000 | >10,000 | >10,000 |

IV Conclusions

The data indicates that the compounds have greater affinity for the H1 receptors as compared with the M1, M2, and M3 receptors, which as described above, indicates that these drugs should result in the reduction of anti-cholinergic side effects.

EXAMPLE 13

Determination of Receptor Selectivity

In one embodiment of the present invention, the selectivity for H1 is increased relative other receptors (i.e., resulting highly soporific compounds with fewer unwanted side effects from binding at adrenergic, muscarinic, serotonergic, and other receptors).

In this regard, a binding assay comparison of (8a), a doxepine-like compound, was performed using a variety of receptor types, shown below in Table 7, to determine receptor selectivity. As is evident from the results shown below the selectivity of (8a) for H1 is dramatically improved over the precursor molecule doxepin.

TABLE 7

| | Percent Inhibition (1.0E−6) | |
|---|---|---|
| Receptor | Doxepin | (8a) |
| Adrenergic, Alpha 1, Non-selective | 92.1 | 1.7 |
| Adrenergic, Alpha 2, Non-selective | 53.5 | −1.8 |
| Histamine, H1 | 100.5 | 89.1 |
| Histamine, H2 | 74.7 | 33.4 |
| Muscarinic, M1 (Human Recombinant) | 88.9 | 3.3 |
| Muscarinic, M2 (Human Recombinant) | 74.0 | 8.2 |
| Muscarinic, Non-selective, Central | 95.2 | 4.4 |
| Muscarinic, Non-selective, Peripheral | 88.4 | 15.0 |
| Norepinephrine Transporter | 97.8 | −3.9 |
| Serotonin Transporter | 75.3 | 9.3 |
| Serotonin, Non-selective | 68.4 | 17.0 |
| Sigma, Non-selective | 52.5 | −2.9 |
| HERG | 23%** | 4% |

**Seldane, etc. = 100%

1. *Chem. Pharm. Bull.* 1994, 42(11), 2276–2284 and 2285–2290.
2. *Synthesis* 1976, 172–176.
3. *J Labeled Compds. and Radiopharmaceuticals* 1995, 36(10), 973–979.
4. *J Pharmaceutical Sci.* 1984, 73(10), 1339–1344.

Incorporation By Reference

The entire contents of all patents, published patent applications and other references cited herein are hereby expressly incorporated herein in their entireties by reference.

Equivalents

Those skilled in the art will recognize, or be able to ascertain, using no more than routine experimentation, many equivalents to specific embodiments of the invention described specifically herein. Such equivalents are intended to be encompassed in the scope of the following claims.

What is claimed is:

1. A method of treating a sleep disorder in a subject, wherein the sleep disorder is selected from insomnia, hypersomnia, narcolepsy, sleep apnea syndrome, parasomnia, restless leg syndrome, and circadian rhythm abnormality sleep disorder, comprising administering to the subject in need of treatment for the sleeping disorder an amount of a compound effective for treating the sleep disorder, wherein said compound is selected from the group consisting of:
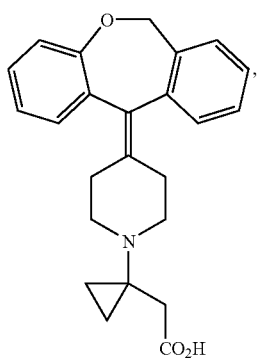
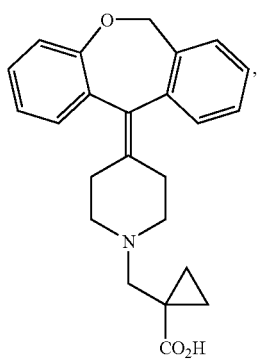
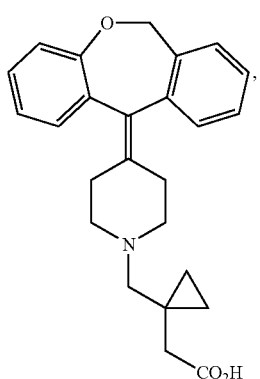
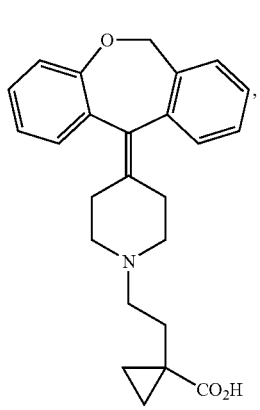
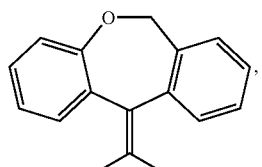
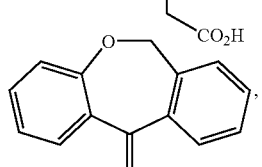
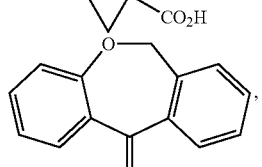
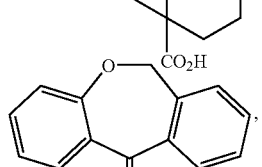
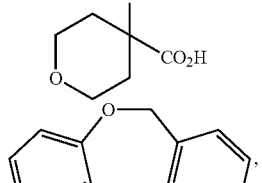
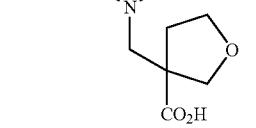

-continued

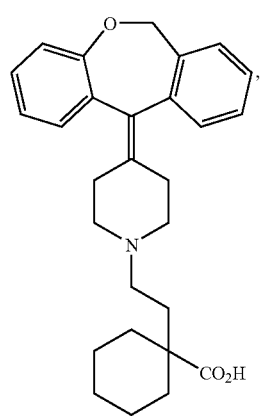

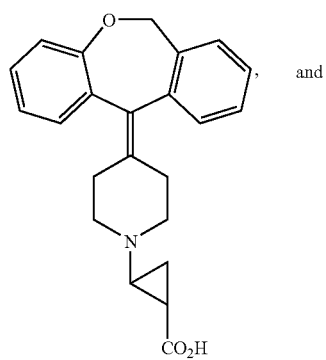 and

-continued

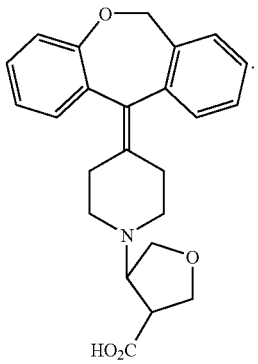

2. The method of claim 1, wherein the subject is a human.

3. The method of claim 1, wherein the sleep disorder is circadian rhythm abnormality sleep disorder.

4. The method of claim 3, wherein the circadian rhythm abnormality sleep disorder is selected from the group consisting of jet lag, shift-work disorders, and delayed or advanced sleep phase syndrome.

5. The method of claim 1, wherein the sleep disorder is insomnia.

6. The method of claim 5, wherein insomnia is treated in the subject by effecting at least one action selected from the group consisting of decreasing the time to sleep onset, increasing the average sleep bout length, and increasing the maximum sleep bout length.

* * * * *